United States Patent
Frisina et al.

(10) Patent No.: US 10,342,806 B2
(45) Date of Patent: Jul. 9, 2019

(54) HORMONE TREATMENT FOR AGE-RELATED HEARING LOSS-PRESBYCUSIS

(71) Applicants: Robert Dana Frisina, Tampa, FL (US); Joseph Paul Walton, Tampa, FL (US); Bo Ding, Tampa, FL (US); Xiaoxia Zhu, Tampa, FL (US)

(72) Inventors: Robert Dana Frisina, Tampa, FL (US); Joseph Paul Walton, Tampa, FL (US); Bo Ding, Tampa, FL (US); Xiaoxia Zhu, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/196,878

(22) Filed: Jun. 29, 2016

(65) Prior Publication Data

US 2016/0375038 A1 Dec. 29, 2016

Related U.S. Application Data

(63) Continuation of application No. PCT/US2015/015216, filed on Feb. 10, 2015.

(60) Provisional application No. 61/937,699, filed on Feb. 10, 2014.

(51) Int. Cl.
| | |
|---|---|
| *A61K 31/573* | (2006.01) |
| *A61K 45/06* | (2006.01) |
| *A61K 31/616* | (2006.01) |
| *A61K 31/192* | (2006.01) |
| *A61K 33/02* | (2006.01) |

(52) U.S. Cl.
CPC .......... *A61K 31/573* (2013.01); *A61K 31/192* (2013.01); *A61K 31/616* (2013.01); *A61K 33/02* (2013.01); *A61K 45/06* (2013.01)

(58) Field of Classification Search
CPC .............. A61K 2300/00; A61K 31/192; A61K 31/573; A61K 31/616; A61K 33/02; A61K 45/06
USPC .......................................................... 424/685
See application file for complete search history.

(56) References Cited

U.S. PATENT DOCUMENTS

| | | | | |
|---|---|---|---|---|
| 6,458,338 B1* | 10/2002 | Adjei | ...................... | A61K 9/008 424/45 |
| 2004/0204471 A1* | 10/2004 | Seibert | ................... | A61K 31/00 514/406 |
| 2007/0021352 A1* | 1/2007 | Anderson | ............ | A61K 31/198 514/379 |
| 2010/0081681 A1 | 4/2010 | Blagosklonny | | |
| 2010/0197800 A1 | 8/2010 | Friedman et al. | | |
| 2011/0166060 A1* | 7/2011 | Simons | ................ | A61K 9/0046 514/2.8 |
| 2012/0277199 A1 | 11/2012 | Ye et al. | | |

OTHER PUBLICATIONS

Rebsamen et al., Direct and Indirect Effects of Aldosterone on Cyclooxygenase-2 and Interleukin-6 Expression in Rat Cardiac Cells in Culture and after Myocardial Infraction, Jul. 2004, Endocrinology 145(7): 3135-3142, (Year: 2004).*
Bauer, Age-related changes in the renin-aldosterone system. Physiological effects and clinical implications. Drugs Aging. 1993;3(3):238-45.
Belmin, et al., Changes in the renin-angiotensin-aldosterone axis in later life. Drugs Aging. 1994;5(5):391-400.
Caspary, et al., Immunocytochemical and neurochemical evidence for age-related loss of GABA in the inferior colliculus: implications for neural presbycusis. J Neurosci. Jul. 1990;10(7):2363-72.
Cohen, et al., Induced differentiation in HT29, a human colon adenocarcinoma cell line. J Cell Sci 112: 2657-2566, 1999.
Cox, et al., Effects of autonomic agonists and immunomodulatory cytokines on polymeric immunoglobulin receptor expression by cultured rat and human salivary and colonic cell lines. Arch Oral Biol 52: 411-416, 2007.

(Continued)

*Primary Examiner* — Johann R Richter
*Assistant Examiner* — Courtney A Brown
(74) *Attorney, Agent, or Firm* — Michele L. Lawson; Robert J. Varkonyi; Smith & Hopen, P.A.

(57) ABSTRACT

Permanent hearing loss or deafness affects about 15% of people worldwide, about 40 million in the US alone. There are currently no FDA-approved drugs on the market in the US, or anywhere in the world that prevent, treat or reverse permanent hearing loss or deafness. Age-related hearing loss (ARHL) is one of the most common forms of permanent hearing loss and deafness. ARHL is the #1 neurodegenerative disorder, #1 communication disorder, and 1 of the top 3 chronic medical conditions (along with arthritis & cardiovascular diseases) of our aged population. The incidence of ARHL is increasing due to the "Baby Boomers" reaching old age, and cumulative effects of lifetime noise exposure, and widespread use of chemotherapeutic and antibiotic drugs, which are ototoxic, or have ototoxic side effects. A new drug is disclosed to prevent or slow the progression of ARHL, based upon natural, existing FDA-approved compounds that are on the market to treat other non-ARHL biomedical problems. When given in the proper dosage the compounds have few, if any side effects, and initial evidence supports the effectiveness of the drug from in vitro experiments, and in vivo studies of aging mice, indicating is usefulness in preventing/treating one of the most pervasive forms of permanent hearing loss.

12 Claims, 35 Drawing Sheets
Specification includes a Sequence Listing.

(56) References Cited

OTHER PUBLICATIONS

Delpire, et al., Deafness and imbalance associated with inactivation of the secretory Na—K—2Cl cotransporter. Nat Genet 22: 192-195, 1999.

Ding, et al. (2014) Simultaneous declines in NKCC1 and Na,K-ATPase, but not Kir4.1 and KCNQ1/KCNE1, are found in the cochlear lateral wall of CBA/CaJ mice with age-related hearing loss. Soc. Neurosci. Abstr. 39.

Eisen et al., Novel membrane receptors for aldosterone in human lymphocytes: a 50 kDa protein on SDS-PAGE. Cell Mol Biol 40: 351-358, 1994.

Epple, et al., Early aldosterone effect in distal colon by transcriptional regulation of ENaC subunits. Am J Physiol Gastrointest Liver Physiol 278: G718-G724, 2000.

Faingold et al., On the role of GABA as an inhibitory neurotransmitter in inferior colliculus neurons: iontophoretic studies. Brain Res. Oct. 23, 1989;500(1-2):302-12.

Garcon et al., K+ and NH4(+) modulate gill (Na+,K+)-ATPase activity in the blue crab, Callinectes omatus: tine tuning of ammonia excretion. Comp Biochem Physiol A Mol Integr Physiol. May 2007;147(1):145-55.

Grossman, et al., Human mineralocorticoid receptor expression renders cells responsive for nongenotropic aldosterone actions. Mol Endocrinol 19: 1697-1710, 2005.

Guimaraes, et al., Progestin Negatively Affects Hearing in Aged Women. Proc. Nat. Acad. Sci.—PNAS. 2006;103: 14246-9.

Guo, et al., Axin and GSK3-b control Smad3 protein stability and modulate TGF-γ signaling. Genes Dev 22: 106-120, 2008.

Hallengren B., et al., 80-year-old men have elevated plasma concentrations of catecholamines but decreased plasma renin activity and aldosterone as compared to young men. Aging (Milano). 1992;4(4):341-5.

Ratner, et al., Pendrin in the mouse kidney is primarily regulated by Cl-excretion but also by systemic metabolic acidosis. Am J Physiol Cell Physiol. Dec. 2008;295(6):C1658-67.

Hegstad, et al., Aging and aldosterone. Am J Med. Mar. 1983;74(3):442-8.

Ikebe et al., Upregulation of the secretory-type Na(+)/K(+)/2Cl(−)-cotransporter in the kidney by metabolic acidosis and lehydration in rats. J Am Soc Nephrol. Mar. 2001;12(3):423-30.

Jayakumar et al., Na—K—Cl cotransporter-1 in the mechanism of ammonia-induced astrocyte swelling. J Biol Chem. Dec. 5, 2008;283(49):33874-82.

Jiang, et al., Aldosterone regulates the Na—K—2Cl cotransporter in vascular smooth muscle. Hypertension 41: 1131-1135, 2003.

Kim, et al., Salt sensitivity of blood pressure in NKCC1-deficient mice. Am J Physiol Renal Physiol 295: F1230-F1238, 2008.

Le Moëllic, et al., Early nongenomic events in aldosterone action in renal collecting duct cells: PKC-alpha activation, mineralocorticoid receptor phosphorylation, and cross-talk with the genomic response. J Am Soc Nephrol 15: 1145-1160, 2004.

Masui et al., Modulation by ammonium ions of gill microsomal (Na+,K+)-ATPase in the swimming crab Callinectes Janae: a possible mechanism for regulation of ammonia excretion. Comp Biochem Physiol C Toxicol Pharmacol. Aug. 2002;132(4):471-82.

Marver, Influence of adrenalectomy and steroid replacement on heart citrate synthase levels. Am J Physiol Endocrinol Metab 246: E452-E457, 1984.

Michea, et al., Eplerenone blocks nongenomic effects of aldosterone on the Na+/H+ exchanger, intracellular Ca2+ levels, and vasoconstriction in mesenteric resistance vessels. Endocrinology 146: 973-980, 200.

Mihallidou, Nongenomic actions of aldosterone: physiological or pathophysiological role? Steroids 71: 277-280, 2006.

Nowik et al., Induction of metabolic acidosis with ammonium chloride (NH4Cl) in mice and rats—species differences and technical considerations. Cell Physiol Biochem. 2010;26(6):1059-72.

Pedersen, et al., Physiology and pathophysiology of Na+/H+ exchange and Na+—K+—2Cl—cotransport in the heart, brain and blood. Am J Physiol Regul Integr Comp Physiol 291: R1-R25, 2006.

Price, et al., Hormone replacement therapy diminishes hearing in perimenopausal mice. Hear. Res. 2009;252: 29-36.

Reisinger et al., Dietary ammonium chloride for the acidification of mouse urine. J AM Assoc Lab Anim Sci. Mar. 2009;48(2):144-6.

Russell, Sodium-potassium-chloride cotransport. Physiol Rev 80: 211-276, 2000.

Salt & Thalmann, New concepts regarding the volume flow of endolymph and perilymph. Adv Otorhinolaryngol 37: 11-17, 1987.

Schmiedt, The physiology of cochlear presbycusis. In: The Aging Auditory System: Perceptual Characterization and Neural Bases of Presbycusis, edited by Gordon-Salant S, Frisina RD, Popper A, Fay RR. New York: Springer-Verlag, chapt 2, 2010, p. 9-38.

Schulte & Schmiedt, Lateral wall Na,K-ATPase and endocochlear potentials decline with age in quiet-reared gerbils. Hear Res 61: 35-46, 1992.

Simard, et al., Homooligomeric and heterooligomeric associations between K—Cl-cotransporter isoforms and between Na+—K+ and Na+—K+—2Cl—cotransporters. J Biol Chem 282: 18083-18093, 2007.

Sinawat et al., Fetal abnormalities produced after preimplantation exposure of mouse embryos to ammonium chloride. Hum Reprod. Oct. 2003;18(10):2157-65.

Smith, et al., COMMD1 interacts with the Cooh terminus of NKCC1 in Calu-3 airway epithelial cells to modulate NKCC1 ubiquitination. Am J Physiol Cell Physiol 305: C133-C146, 2013.

Tadros, et al., High Serum Aldosterone Levels Correlate with Lower Hearing Thresholds in Aged Humans: A Possible Protective Hormone against Presbycusis. Hear. Res. 2005;209:10-18.

Thompson, et al., Estrogen Blockade Reduces Auditory Feedback in CBA Mice. Otolaryngol—Head Neck Surg. 2006;135:100-105.

Tokarz et al., Age-related cochlear cytokine gene expression in the BALB/cJ mouse with systemic versus intratympanic dosing of steroid drugs. Acta Otolaryngol. Jul. 2013;133(7):685-91.

Verschuur et al., Markers of inflammatory status are associated with hearing threshold in older people: findings from the Hertfordshire ageing study. Age Ageing. Jan. 2012;41(1):92-7.

Wall, et al., Hypotension in NKCC1 null mice: role of the kidneys. Am J Physiol Renal Physiol 290: F409-F416, 2006.

Weaver, et al., A thallium-sensitive, fluorescence-based assay for detecting and characterizing potassium channel modulators in mammalian cells. J Biomol Screen 9: 671-677, 2004.

Mulkerrin, et al., Aldosterone responses to hyperkalemia in healthy elderly humans. J. Am. Soc. Nephrol. 1995;6(5):1459-62.

International Search Report and Written Opinion issued by the International Searching Authority dated Jun. 25, 2015 for corresponding International Patent Application No. PCT/US2015/015216.

International Preliminary Report on Patentability issued by the International Bureau dated Aug. 25, 2016 for corresponding International Patent Application No. PCT/US2015/015216.

Frisina, Robert D. Hormones and Hearing: Too Much or Too Little of a Good Thing Can Be Ototoxic. Sem. Hear. vol. 33(3), 2012, pp. 231-241.

Sachse, F. et al. Anti-inflammatory effects of ciprofloxacin in S. aureus Newman induced nasal inflammation in vitro. J. Inflamm (Lond). 2008. vol. 5:11.

Zahnert, Thomas. The Differential Diagnosis of Hearing Loss. Dtsch Arztebl Int 2011: 108(25): pp. 433-444.

Zhang, Jin-thong et al. Anti-Inflammatory Effects of Besifloxacin, a Novel Fluoroquinolone, in Primary Human Corneal Epithelial Cells. Curr Eye Res. 2008, vol. 33(11), pp. 923-932.

Labro, MT. Antibiotics as anti-inflammatory agents. Cuff Opin Investig Drugs. 2002, vol. 3(1), p. 61-8. Abstract [online]. Retrieved on Mar. 16, 2015. Retrieved from the Internet: http://www.ncbi.nlm.nih.gov/pubmed/12054075.

Trune, Dennis R. et al. Corticosteroid Therapy for Hearing and Balance Orders. The Anatomical Record, 2012. 295:1928-1943.

Trune, Dennis R. et al. Aldosterone (Mineralocorticoid) Equivalent to Prednisolone (Glucocorticoid) in Reversing Hearing Loss in MRL/MpJ-Fas1pr Autoimmune Mice. Laryngoscope 110: Nov. 2000, pp. 1902-1906.

(56) References Cited

OTHER PUBLICATIONS

Trune, Dennis R. et al. Aldosterone and prednisolone control of cochlear function in MRL/MpJ-Fas1pr autoimmune mice. Hearing Research 155 (2001) 9-20.
Trune, Dennis R. et al. Mineralocorticoid receptor mediates glucocorticoid treatment effects in the autoimmune mouse ear. Hearing Research 212 (2006) 22-32.
Humes, et al. Central Presbycusis: A Review and Evaluation of the Evidence. J Am Acad Audiol 23:635-666 (2012).
Ratnaparkhi, et al. Sustained Release Oral Drug Delivery System—An Overview. International Journal of Pharma Research & Review, Mar. 2013; 2(3):11-21.
Gupta, et al. A Review on: Sustained Release Technology. International Journal of Therapeutic Applications, vol. 8, 2012, 18-23.
Parashar, et al. Novel Oral Sustained Release Techonolgy: A Concise Review. Int. J. Res. Dev. Pharm. L. Sci. Feb.-Mar. 2013, 2(2), 262-269.
Patil, et al. A Basic Approach on Sustained Release Drug Delivery System. Am. J. PharmTech Rex. 2012; 2(5), 213-231.
Fetoni, et al. Pathogenesis of presbycusis in animal models: A review. Experimental Gerontology 46 (2011) 413-425.
Gates, et al. Presbycusis. Lancet 2005; 366: 1111-1120.
Huang, et al. Age-related hearing loss or presbycusis. Eur Arch Otorhinolaryngol (2010) 267:1179-1191.
Zhang, Ming-Zhi et al. Regulation of cyclooxygenase-2 (COX-2) in rat renal cortex by adrenal glucocorticoids and mineralocorticoids. PNAS, Dec. 21, 1999, vol. 96, No. 26, pp. 15280-15285.
Harris, R.C. et al. Cyclooxygenase-2 and the renal renin-angiotensin system. Acta Physiol Scand 2004, 181, 543-547.
Major Differences. Difference between Glucocorticoids and Mineralocorticoids. http://majordifferences.com/2014/04/difference-between-glucocorticoids-and.html#.Wlfj_vmnGUn. Accessed on Jan. 11, 2018.

\* cited by examiner

SEQUENCE LISTING

```
<160> NUMBER OF SEQ ID NOS: 8

<210> SEQ ID NO 1
<211> LENGTH: 18
<212> TYPE: DNA
<213> ORGANISM: artificial
<220> FEATURE:
<223> OTHER INFORMATION: artificial PCR primer

<400> SEQUENCE: 1
cctggcaccc agcacaat                                                 18

<210> SEQ ID NO 2
<211> LENGTH: 18
<212> TYPE: DNA
<213> ORGANISM: artificial
<220> FEATURE:
<223> OTHER INFORMATION: artificial PCR primer

<400> SEQUENCE: 2
gggccggact cgtcatac                                                 18

<210> SEQ ID NO 3
<211> LENGTH: 23
<212> TYPE: DNA
<213> ORGANISM: artificial
<220> FEATURE:
<223> OTHER INFORMATION: artificial PCR primer

<400> SEQUENCE: 3
accttcggcc acaacaccat gga                                           23

<210> SEQ ID NO 4
<211> LENGTH: 21
<212> TYPE: DNA
<213> ORGANISM: artificial
<220> FEATURE:
<223> OTHER INFORMATION: artificial PCR primer

<400> SEQUENCE: 4
accacagcat ctctggttgg a                                             21

<210> SEQ ID NO 5
<211> LENGTH: 20
<212> TYPE: DNA
<213> ORGANISM: artificial
<220> FEATURE:
<223> OTHER INFORMATION: artificial PCR primer

<400> SEQUENCE: 5
ttggcgttcg tgattactgt                                               20

<210> SEQ ID NO 6
<211> LENGTH: 17
<212> TYPE: DNA
<213> ORGANISM: artificial
<220> FEATURE:
<223> OTHER INFORMATION: artificial PCR primer

<400> SEQUENCE: 6
atcaggctgg tactcaa                                                  17

<210> SEQ ID NO 7
<211> LENGTH: 20
<212> TYPE: DNA
<213> ORGANISM: artificial
```

```
<220> FEATURE:
<223> OTHER INFORMATION: artificial PCR pimer

<400> SEQUENCE: 7
ctgggacagc acagaatgtt                                              20

<210> SEQ ID NO 8
<211> LENGTH: 20
<212> TYPE: DNA
<213> ORGANISM: artificial
<220> FEATURE:
<223> OTHER INFORMATION: artificially generated PCR primer sequence

<400> SEQUENCE: 8
taggcttgtc tctgggtcct                                              20
```

HORMONE TREATMENT FOR AGE-RELATED HEARING LOSS-PRESBYCUSIS

CROSS REFERENCE TO RELATED APPLICATIONS

This application is a continuation of and claims priority to International Patent Application No. PCT/US2015/015216, with the same title, filed Feb. 10, 2015, which claims priority to U.S. Provisional Patent Application No. 61/937,699, with the same title, filed on Feb. 10, 2014, the contents of which are herein incorporated by reference.

STATEMENT OF GOVERNMENT SUPPORT

This invention was made with government support under Grant No. P01 AG009524 awarded by the National Institutes of Health and National Institute on Aging. The government has certain rights in the invention.

FIELD OF INVENTION

This invention relates to treatment of age-related hearing loss and disorders. More specifically, the invention comprises compositions of a hormone and non-steroidal anti-inflammatory drug (NSAID) and use of the compositions in treating age-related hearing loss and disorders.

BACKGROUND OF THE INVENTION

Permanent hearing loss or deafness affects about 15% of people worldwide, and about 40 million in the US alone. Age-related hearing loss (ARHL)—presbycusis—is the number one neurodegenerative condition and top communication disorder of our aged population; and is one of the three most prevalent, major, chronic medical conditions along with arthritis and cardiovascular disease for our elderly. ARHL is the #1 neurodegenerative disorder, #1 communication disorder, and 1 of the top 3 chronic medical conditions (along with arthritis & cardiovascular diseases) of the U.S. aged population. The incidence of ARHL is increasing due to the "Baby Boomers" reaching old age, i.e. over the age of 65, and cumulative effects of lifetime noise exposure, and widespread use of chemotherapeutic and antibiotic drugs, which are ototoxic, or have ototoxic side effects. This results in a significant decline in workplace productivity, quality of life, and ability to communicate in family situations with spouses, siblings, children and grandchildren. The psychological sequelae accompanying ARHL can cause depression, anxiety, social isolation, loneliness and sometimes can be life threatening. In addition, hearing loss has been linked as a precursor to cognitive decline in the elderly (Lin, et al., Hearing Loss and Cognition in the Baltimore Longitudinal Study of Aging. Neuropsychol. 2011; 25(6): 763-770).

Presbycusis is a sensorineural hearing loss that gradually occurs in most individuals as they age, and is generally affects both ears equally. It typically impacts high-pitched sounds more than low-pitched sounds, and has a significant impact on understanding speech in the presence of background noise. While presbycusis has many causes, it most commonly stems from changes in the inner ear during aging, such as a loss of hair cells in the inner ear. However, changes in the blood supply to the ear, such as by heart disease, high blood pressure, vascular effects of diabetes, or other circulatory problems can result in presbycusis, abnormalities of the outer ear and/or middle ear, such as reduced function of the tympanic membrane (the eardrum) or the malleus, incus, or stapes, can result in conductive presbycusis. Additionally, changes along the nerve pathways between the ear and brain, and deficits in the parts of the brain used for hearing, can also result in presbycusis. Alarmingly, it is estimated that the prevalence of tinnitus, increasing with age, peaks between 60-69 yr at over 14% (Shargorodsky et al., 2010) and is likely under-reported. Chronic tinnitus frequently impacts sleep, stress, psychological well-being, quality of life, and in severe cases, the will to live (Dobie, 2003; Hebert and Carrier, 2007; Hebert et al., 2012, 2013; Heller, 2003).

Proper regulation of ionic concentrations is necessary for optimal performance of the body's physiological systems. The $Na^+$—$K^+$-$2Cl^-$ cotransport protein (e.g., NKCC1) is a key membrane molecule that moves $Na^+$, $K^+$, and $Cl^-$ into and out of cells for proper physiological function (Pedersen, et al., Physiology and pathophysiology of $Na^+/H^+$ exchange and $Na^+$—$K^+$-$2Cl^-$ cotransport in the heart, brain and blood. *Am J Physiol Regul Integr Comp Physiol* 291: R1-R25, 2006). Its properties have been studied in the cardiovascular system, including regulation of salt concentration, cell volume, and maintenance of cellular homeostasis in response to osmotic and oxidative stress functions in cardiomyocytes and vascular smooth muscle (Hebert, et al., Molecular physiology of cation-coupled Cl_ cotransport: the SLC12 family *Flügers Arch* 447: 580-593, 2004). NKCC1 is also involved in regulation of blood pressure and left ventricular pressure (Gang, et al., Effect of the Na—K-2Cl cotransporter NKCC1 on systemic blood pressure and smooth muscle tone. *Am J Physiol Heart Circ Physiol* 292: H2100-H2105, 2007, Meyer, et al., Decreased blood pressure and vascular smooth muscle tone in mice lacking basolateral $Na^+$—$K^+$-$2Cl^-$ cotransporter. *Am J Physiol Heart Circ Physiol* 283: H1846-H1855, 2002). In particular, Jiang et al. (Jiang, et al., Aldosterone regulates the Na—K-2Cl cotransporter in vascular smooth muscle. *Hypertension* 41: 1131-1135, 2003) found that aldoterone (ALD) increases NKCC1 activity in conjunction with heart failure, but the mRNA expression levels do not change, suggesting posttranslational modifications. The human gene locus for NKCC1 has been identified as 5q23.3 and is encoded by Slc12a2 in mouse (Delpire & Austin, Kinase regulation of $Na^+$—$K^+$-$2Cl^-$ cotransport in primary afferent neurons. *J Physiol* 588: 3365-3373, 2010).

NKCC1 also plays key roles in renal physiology and fluid ionic regulation. For instance, in response to reductions in intracellular chloride concentrations, Ste20-related proline-alanine-rich kinase (SPAK) phosphorylates NKCC1 to elevate cotransporter activity and raise chloride influx (Dowd & Forbush, PASK (proline-alanine-rich STE20-related kinase), a regulatory kinase of the Na—K—Cl cotransporter (NKCC1). *J Biol Chem* 278: 27347-27353, 2003, Smith, et al., PKC-delta acts upstream of SPAK in the activation of NKCC1 by hyperosmotic stress in human airway epithelial cells. *J Biol Chem* 283: 22147-22156, 2008). Oxidative stress response kinase 1 (OSR1) also phosphorylates and activates NKCC1 in the presence of oxidative stress (Simard, et al., Homooligomeric and heterooligomeric associations between K_-Cl_ cotransporter isoforms and between $Na^+$—$K^+$-$2Cl^-$ cotransporters. *J Biol Chem* 282: 18083-18093, 2007). Therefore, because of its important physiological functions, mis-regulation or deficiencies in the expression or distribution of NKCC1 isoforms in kidney epithelial cells can have negative physiological consequences.

For sensory systems, the cochlea, a specialized organ of the auditory sensory system, critically depends on the presence of NKCC1 transporters in epithelial cells of its lateral wall, particularly in the basolateral plasma membrane of stria marginal cells (Wall, et al., Hypotension in NKCC1 null mice: role of the kidneys. *Am J Physiol Renal Physiol* 290: F409-F416, 2006, Weaver, et al., A thallium-sensitive, fluorescence-based assay for detecting and characterizing potassium channel modulators in mammalian cells. *J Biomol Screen* 9: 671-677, 2004) where endolymph is made, an unusual, $K^+$-rich fluid. The endocochlear potential (EP), of the endolymph is the physiological "battery" providing power to the auditory transduction receptors, or hair cells, epithelial cells of the inner ear that convert sound into the code of the nervous system (Russell, Sodium-potassium-chloride cotransport. *Physiol Rev* 80: 211-276, 2000, Salt & Thalmann, New concepts regarding the volume flow of endolymph and perilymph. *Adv Otorhinolaryngol* 37: 11-17, 1987, Schmiedt, The physiology of cochlear presbycusis. In: *The Aging Auditory System: Perceptual Characterization and Neural Bases of Presbycusis*, edited by Gordon-Salant S, Frisina R D, Popper A, Fay R R. New York: Springer-Verlag, chapt 2, 2010, p. 9-38). The critical physiological role of NKCC is supported by evidence indicating that furosemide blocks NKCC1 function in the cochlea, causing hearing loss or balance deficits, resulting from impaired endolymph production and EP declines (Salt & Thalmann, New concepts regarding the volume flow of endolymph and perilymph. *Adv Otorhinolaryngol* 37: 11-17, 1987, Schmiedt, The physiology of cochlear presbycusis. In: *The Aging Auditory System: Perceptual Characterization and Neural Bases of Presbycusis*, edited by Gordon-Salant S, Frisina R D, Popper A, Fay R R. New York: Springer-Verlag, chapt 2, 2010, p. 9-38, Schulte & Schmiedt, Lateral wall Na,K-ATPase and endocochlear potentials decline with age in quiet-reared gerbils. *Hear Res* 61: 35-46, 1992). Furosemide is a loop diuretic used clinically for the treatment of congestive heart failure and edema by reducing NKCC activity in epithelial cells of the kidney. The findings of Schmiedt et al. (Schmiedt, et al., Effects of furosemide applied chronically to the round window. *J Neurosci* 22: 9643-9650, 2002) suggest that since the EP declines with age in the mammalian cochlea, reductions in the expression or functionality of NKCC1 proteins in epithelial cells of the cochlear lateral wall play a role in age-related hearing loss, presbycusis (Delpire, et al., Deafness and imbalance associated with inactivation of the secretory Na—K-2Cl cotransporter. *Nat Genet* 22: 192-195, 1999).

Initial studies report that NKCC1 proteins are also expressed in the nervous system.

They can be found in the apical membrane of the choroid plexus, in perikarya of certain central nervous system (CNS) neurons, in oligodendrocytes, and in dorsal root ganglion sensory neurons of the peripheral nervous system (Garg, et al., Effect of the Na—K-2Cl cotransporter NKCC1 on systemic blood pressure and smooth muscle tone. *Am J Physiol Heart Circ Physiol* 292: H2100-H2105, 2007, Haas & Forbush, The Na—K—Cl cotransporter of secretory epithelia. *Annu Rev Physiol* 62: 515-534, 2000). It is known, for example, that the relative expression levels of NKCC1 and NKCC2 determine whether neuronal responses to gamma amino butyric acid (GABA), an important neurotransmitter, are excitatory (depolarizing) or inhibitory (hyper-polarizing) in the CNS (Cox, et al., Effects of autonomic agonists and immunomodulatory cytokines on polymeric immunoglobulin receptor expression by cultured rat and human salivary and colonic cell lines. *Arch Oral Biol* 52: 411-416, 2007). The relative protein expression levels and corresponding neurophysiological responses that they determine change during neuronal development, including olfactory bulb neuronal migration (Haas & Forbush, The Na—K—Cl cotransporter of secretory epithelia. *Annu Rev Physiol* 62: 515-534, 2000, Marver, Influence of adrenalectomy and steroid replacement on heart citrate synthase levels. *Am J Physiol Endocrinol Metab* 246: E452-E457, 1984), and during peripheral sensory nerve regeneration following sectioning of the mouse sciatic nerve in vivo (Phakdeekitcharoen, et al., Aldosterone increases $Na^+$—$K^+$-ATPase activity in skeletal muscle of patients with Conn's syndrome. *Clin Endocrinol (Oxf)* 74: 152-159, 2010). Also, since GABA is a prevalent neurotransmitter that modifies neuronal excitability, altered NKCC1 regulation has been implicated in cases of epilepsy (Dowd & Forbush, PASK (proline-alanine-rich STE20-related kinase), a regulatory kinase of the Na—K—Cl cotransporter (NKCC1). *J Biol Chem* 278: 27347-27353, 2003).

A number of serious and prevalent diseases involve disorders and pathologies of epithelial cells. Specifically, in respiratory epithelial cells, NKCC1 resides in the basolateral membrane of salivary gland and epithelial cells lining the airways. In the gastrointestinal tract, NKCC1 is found in the inner medullary collecting duct cells, and rectal gland cells, thus allowing efficient salt and water secretion and reabsorption and volume regulation (Hebert, et al., Molecular physiology of cation-coupled Cl_ cotransport: the SLC12 family. *Pflügers Arch* 447: 580-593, 2004, Russell, Sodium-potassium-chloride cotransport. *Physiol Rev* 80: 211-276, 2000). Disruption of the NKCC1 system can be significant for these physiological systems. For example, cystic fibrosis, a debilitating lung disease that also affects the kidneys, liver, and intestine, is characterized by abnormal transport of $Na^+$ and $Cl^-$ across epithelial cells, leading to thick, viscous secretions and serious respiratory ailments, and its mechanisms have been investigated utilizing HT-29 epithelial cells (Baudouin-Legros et al., Modulation of CFTR gene expression in HT-29 cells by extracellular hyperosmolarity. *Am J Physiol Cell Physiol* 278: C49-C56, 2000; Baudouin-Legro, et al., Cell-specific posttranscriptional regulation of CFTR gene expression via influence of MAPK cascades on 3'-UTR part of transcripts. *Am J Physiol Cell Physiol* 289: C1240-C1250, 2005, Montrose-Rafizadeh, et al., Gene target-ing of a CFTR allele in HT29 human epithelial cells. *J Cell Physiol* 170: C299-C308, 1997).

Precise control of NKCC1 expression and function would have pharmaceutical and biotherapeutic implications, given the important roles that NKCC1 proteins play in key physiological systems, including cardiac, vascular, renal, hepatic, and sensory. Thus an understanding of NKCC1 regulatory pathways is significant, in light of potentially new treatments for the disorders described above.

The central nucleus of the inferior colliculus (CIC) provides for auditory processing of signals received from structures including the cochlear nuclei (CN) and superior olivary complex (SOC), and are responsible for spatial localization of sound (Caspary, et al, Immunocytochemical and neurochemical evidence for age-related loss of GABA in the inferior colliculus: implications for neural presbycusis. J Neurosci. 1990 July; 10(7):2363-72). In vivo and In vitro studies indicate that processing of acoustic information by the CIC requires GABA, an inhibitory neurotransmitter (Faingold et al., On the role of GABA as an inhibitory neurotransmitter in inferior colliculus neurons: iontophoretic studies. Brain Res. 1989 Oct. 23; 500(1-2):302-12) and that loss of CIC inhibition may result, at least in part, in neural presbycusis (Caspary, et al., Immunocytochemical and neurochemical evidence for age-related loss of GABA in the inferior colliculus: implications for neural presbycusis. J Neurosci. 1990 July; 10(7):2363-72). Further, studies show age-related loss of basal and stimulated levels of GABA, and loss of neurons (Caspary, et al., Immunocytochemical and neurochemical evidence for age-related loss of GABA in the inferior colliculus: implications for neural presbycusis. J Neurosci. 1990 July; 10(7):2363-72).

Recent breakthroughs have demonstrated remarkable plasticity in the central auditory nervous system following exposure to various acoustical environments. For treatments that slow, halt, or reverse auditory or neurodegenerative decline to be maximally effective, it is likely that considerable neural plasticity will be required to accommodate new and modified inputs from the cochlea. A widely recognized form of experience-dependent auditory neural plasticity, involves passive sound exposure, such as augmented auditory environments (AAE) in animal models, and hearing aid acclimatization in humans (Willott & Turner, Prolonged exposure to an augmented acoustic environment ameliorates age-related auditory changes in C57BL/6J and DBA/2J mice. Hear. Res. 1999; 135: 78-88; Engineer, et al., Environmental enrichment improves response strength, threshold, selectivity, and latency of auditory cortex neurons. J. Neurophysiol. 2004; 92: 73-82; Bose, et al., Effect of the environment on the dendritic morphology of the rat auditory cortex. Synapse. 2010; 64(2): 97-110).

There is considerable evidence that, over time, chronically altered AAEs can lead to acclimatization that includes changes in loudness growth, loudness tolerance, preferred loudness levels, and performance on tasks that involve loudness perception such as intensity discrimination (Gatehouse, 1992; Robinson & Gatehouse 1995; Hayes 2013; Munro 2008; Munro & Merrett 2013; Norena & Chery-Croze, 2007). Similarly, numerous studies have shown that the prolonged use of ear-level sound generators (sound supplementation) or the use of ear plugs (auditory deprivation) lead to changes in loudness tolerance and growth (Formby et al., 2003, 2007; Munro & Blount, 2009), and acoustic reflex thresholds (ARTs, Munro & Blount, 2009).

Aldosterone (ALD) is a mineralocorticoid secreted by the adrenal cortex that plays a primary role in controlling serum $Na^+$ and $K^+$ levels and kidney regulation. ALD regulates expression of both Na+/K+-ATPase and NKCC. ALD provides a long-term regulatory effect on Na+/K+-ATPase via changes in mRNA/protein synthesis. This regulatory effect is widespread in organ systems of the body, and specifically has been shown in the inner ear (Pitovski et al. 1993a,b), as well as the brain (Grillo et al. 1997). ALD can also upregulate NKCC, but the mechanism by which it acts is unclear as no increase in NKCC1 mRNA has been shown in other (non-sensory) physiological systems (Jiang et al. 2003).

There are currently no approved drugs on the market anywhere in the world to reduce, reverse or cure permanent hearing loss or deafness including presbycusis/ARHL, which is now the most prevalent form of permanent hearing loss. As such, there is an existing need to develop treatments to prevent, treat or reverse permanent hearing loss.

As such, a new drug is disclosed for the prevention or retarded progression of ARHL, based upon compounds that when given in the proper dosages have few, if any side effects.

SUMMARY OF THE INVENTION

Hormone serum levels generally decline with age. Human and animal investigations uncovered interactions between hormones and ARHL (Tadros, et al., High Serum Aldosterone Levels Correlate with Lower Hearing Thresholds in Aged Humans: A Possible Protective Hormone against Presbycusis. Hear. Res. 2005; 209:10-18; Guimaraes, et al., Progestin Negatively Affects Hearing in Aged Women. Proc. Nat. Acad. Sci.—PNAS. 2006; 103: 14246-9; Thompson, et al., Estrogen Blockade Reduces Auditory Feedback in CBA Mice. Otolaryngol—Head Neck Surg. 2006; 135:100-105; Price, et al., Hormone replacement therapy diminishes hearing in perimenopausal mice. Hear. Res. 2009; 252: 29-36). It is likely that, with correct timing and dosage, hormonal intervention will slow down or prevent the progression of ARHL The drug is a composition comprising a hormone with ammonium chloride and/or a nonsteroidal anti-inflammatory drug. The hormone is optionally aldosterone, which maintains homeostasis for potassium and sodium physiologically in the body. Alternatively, the hormone is cortisone (glycocorticoid) or fludrocortison. Other hormones that utilize the SGK1 pathway are anticipated to be useful as well.

Useful non-steroidal drugs include COX inhibitors, such as aspirin (salicylic acid), ibuprofen, naproxen, other non-aspirin salicylates, such as diflurophenyl salicylate derivatives, salicylsalicylic acid, sodium salicylate, salicyclamide, sodium thiosalicylate, choline salicylate, magnesium salicylate, and choline-magnesium salicylate, phenylbutazone, oxyphenylbutazone, antipyrine, aminopyrine, apazone, indomethacin, sulindac, phenacetin, acetaminophen, mefenamic, meclofenamic, flufenamic, mefenomic, ectofenamic, tolmectin, flurbioprofen, fenoprofen, ketoprofen, fenbufen, pirprofen, oxaprozin, indoprofen and celecoxib.

Aldosterone is used at the lowest concentration that is efficacious in the patient. An exemplary dose is 0.004 mg/kg/day to 0.04 mg/kg/day, or 0.05 mg/day. Fludrocortison can be administered at 0.01 mg/day to about 0.2 mg/day. Where aspirin is used with the hormone, it is proposed to be used at the lowest possible concentration, such as about 5 to about 10 mg/kg/day, or 30-60 mg/day or 60 to about 100 mg/day, or 75 mg/day. Where ibuprofen is used, it is useful at about 2.5 mg/kg/day, or about 0.4 g/day to about 1.2 g/day or 100 mg/day. Naproxen can be administered at 5 to 10 mg/kg/day. In embodiments using ammonium chloride, it is administered at around 500 mg/day in a mouse, at about 1% to about 2% in water, or about 8 to about 12 g/day in humans.

Aldosterone treatment reduces ARHL based on animal models. Combining a hormone, such as aldosterone, with the above-mentioned compounds will increase the effectiveness of the hormone, and allow for lower dosing of hormone to achieve significant therapeutic effects.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
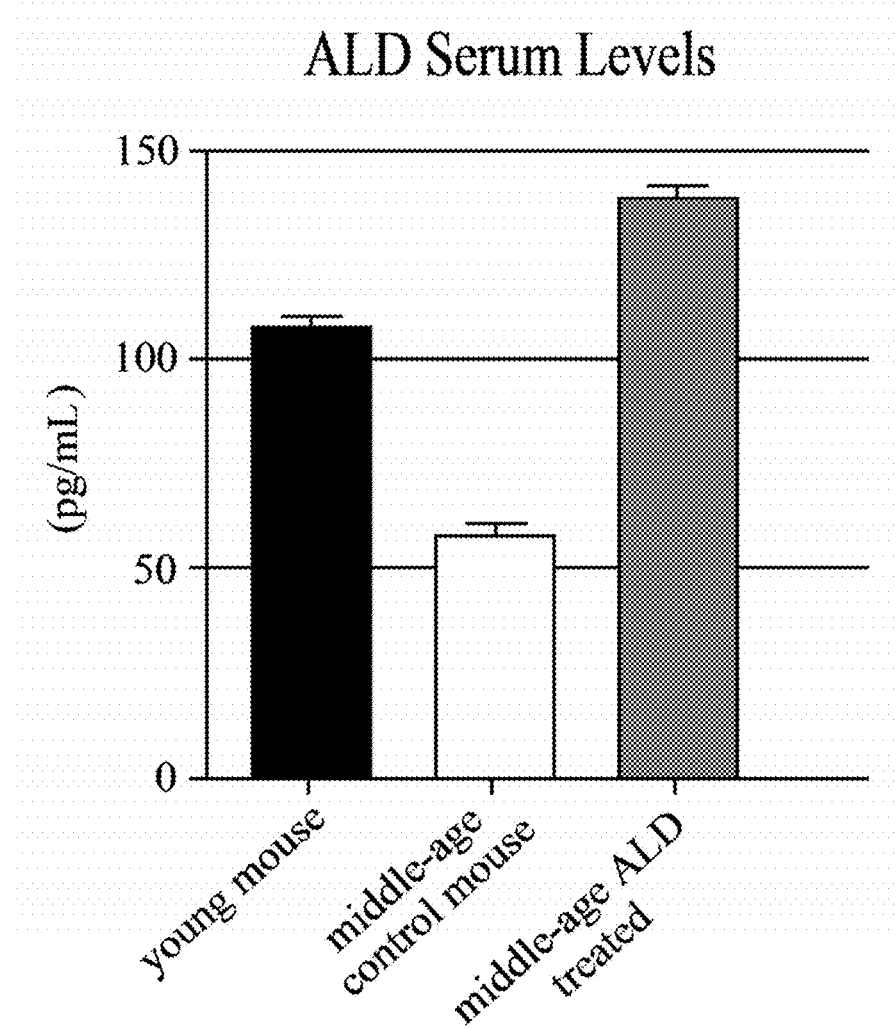
FIG. 1 is a graph showing serum aldosterone levels, as measured by ELISA, were significantly lower in middle aged control CBA/CaJ mice, as compared to Young adult mice and ALD treated middle aged mice (0.0016 mg/day, 120 days release, Innovative Research of America, Sarasota, Fla.). (Normal range for mice: 25-315 pg/ml).

As used herein, the singular forms "a," "an" and "the" include plural referents unless the context clearly dictates otherwise. Thus, for example, reference to "a polypeptide" includes a mixture of two or more polypeptides and the like.

As used herein, "about" means approximately or nearly and in the context of a numerical value or range set forth means±15% of the numerical.

As used herein "animal" means a multicellular, eukaryotic organism classified in the kingdom Animalia or Metazoa. The term includes, but is not limited to, mammals. Non-limiting examples include rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals.

As used herein the term "patient" is understood to include an animal, especially a mammal, and more especially a human that is receiving or intended to receive treatment.

As used herein, the term "therapeutically effective amount" refers to that amount of a therapy (e.g., a drug or chemotherapeutic agent) sufficient to result in the amelioration of age-related hearing loss—presbycusis—or other neurodegenerative disorder or one or more symptoms thereof, prevent advancement of age-related hearing loss or other neurodegenerative disorder, or cause regression of age-related hearing loss or other neurodegenerative disorder.

The CBA/CaJ mouse is an inbred mouse strain developed for longevity, and was therefore used as a model to study age-related hearing loss. A composition comprising aldosterone, which maintains homeostasis for potassium and sodium physiologically in the body is administered by itself, and in combination with ammonium chloride, and/or aspirin salicylic acid, and/or ibuprofen, to treat or delay the onset of key aspects of age-related hearing loss (ARHL)—presbycusis. It has also been found that CBA/CaJ mouse serum ALD levels declined with age. Treatments with ALD were analyzed for its effect on mouse inner ear auditory function, which shows that in mice aldosterone treatment reduces ARHL, and combining aldosterone with the above-mentioned compounds will increase its effectiveness, and allow for lower dosing of aldosterone to achieve significant therapeutic effects.

Example 1

CBA/CaJ mice (The Jackson Laboratory, Bar Harbor, Me.) were treated with aldosterone doses 0.00048 mg/day to 0.00476 mg/day to determine the dose-response curve using slow-release, subcutaneous ALD pellets (Innovative Research of America-IRA, Sarasota, Fla.). After 60 (2 months) or 120 days (4 months) of ALD implantation, mice were anesthetized with a combination of ketamine and xylazine (100 µl i.p. of sterile saline containing 100 mg/ml ketamine and 80 mg/ml xylazine) for ABR measurements. A dose of 0.0016 mg/day was found to be optimal for ABR threshold improvements relative to age-matched control mice.

Example 2

Serum ALD levels decrease with age in humans (Hegstad, et al., Aging and aldosterone. Am J Med. 1983 March; 74(3):442-8; Hallengren B., et al., 80-year-old men have elevated plasma concentrations of catecholamines but decreased plasma renin activity and aldosterone as compared to young men. Aging (Milano). 1992; 4(4):341-5; Bauer, Age-related changes in the renin-aldosterone system. Physiological effects and clinical implications. Drugs Aging. 1993; 3(3):238-45; Belmin, et al., Changes in the renin-angiotensin-aldosterone axis in later life. Drugs Aging. 1994; 5(5):391-400; Mulkerrin, et al., Aldosterone responses to hyperkalemia in healthy elderly humans J Am. Soc. Nephrol. 1995; 6(5):1459-62) and other mammals, including rodents (Brudieux, et al., Age-related decreases in plasma adrenocorticotropic hormone, corticosterone, and aldosterone responses to exogenous corticotropin-releasing hormone in the rat. Gerontol. 1995; 41(6):308-14; Magdich, Age and the effect of adrenocorticotropic hormone on aldosterone secretion in rats. Bull. Eksp. Biol. Med. 1980; 89(7): 19-20; Kau, et al., Age-related impairment of aldosterone secretion in zona glomerulosa cells of ovariectomized rats. J. Investig. Med. 1999; 47(8):425-32).

For example, mean serum ALD levels in mouse pups are in the 1300±150 pg/ml range (McDonald, et al., Disruption of the β subunit of the epithelial Na+ channel in mice: Hyperkalemia and neonatal death associated with a pseudohypoaldosteronism phenotype. Proc. Natl. Acad. Sci. U S A. 1999; 96(4): 1727-1731). In aging mice these mean levels decline, to 900±100 pg/ml (Wang, et al., Chronic hyperaldosteronism in a transgenic mouse model fails to induce cardiac remodeling and fibrosis under a normal-salt diet. Am. J. Physiol. Renal Physiol. 2004; 286:F1178-F1184). A direct role for ALD in ARHL has yet to be demonstrated, however a significant correlation has been identified between low serum ALD and severity of presbycusis in elderly human subjects (Tadros, et al., High Serum Aldosterone Levels Correlate with Lower Hearing Thresholds in Aged Humans: A Possible Protective Hormone against Presbycusis. Hear. Res. 2005; 209:10-18).

CBA/CaJ mice (The Jackson Laboratory, Bar Harbor, Me.) were treated with aldosterone starting at 16-17 months of age. Treatment consisted of a subcutaneous implantation of a 120-day release pellet of D-aldosterone (0.0016 mg/day; Innovative Research of America, Sarasota, Fla.) behind the shoulder in ALD treatment mice (N=5), and same-age control mice (N=5) mice. The mice were kept in their home cages in the USF Vivarium room in the Global Center for Hearing & Speech Research, 12 hour light/dark cycle, 21 degrees C., in a relatively quiet environment with non-invasive auditory testing monthly. After the four month (120 day) course of treatment concluded, the mice were euthanized by injecting a commercial euthanasia solution, Euthasol@, (0.22 ml/kg) intraperitoneally. The depth of narcosis/anesthesia was assessed by using the interdigital pinch reflex. Death was confirmed by terminal phlebotomy/exsanguinations and perfusion.

After the mice were sacrificed, the brachial vessels are exposed after removing the skin over the axilla and the vessels ware cut. Blood was allowed to free-flow from the puncture site and collected with a sterile Pasteur pipette, then transferred to an Eppendorf tube in a 37° C. water bath for 30 min, centrifuged 2000 rpm for 25 min, and then the serum was taken off and stored at −80° C. Also a thoracotomy was performed to gain access to the heart was punctured by an 18G sterile hypodermic needle. Blood collection was done quickly to avoid clotting. Blood was collected in sample containers without any preservatives. The blood was permitted to clot and centrifuged at room temperature at 2000 rpm. Samples were stored at −20° C. until use. The mice were tested for ALD protein levels using an rabbit anti-Aldosterone IgG-based ELISA kit (Cat. No 1875, Alpha Diagnostic Int., San Antonio Tex.) that uses a competitive solid phase.

Briefly, 50 µl of plasma or standard was added to rabbit anti-Aldosterone IgG-coated ELISA strips and 100 µl of an Aldosterone-avadin conjugated solution added to each sample. The samples were mixed for 5-10 seconds, followed by washing 3 times with the supplied wash buffer. A horseradish peroxidase substrate (Aldosterone-HRP conjugate) was added (150 µl) to each well and mixed for 5-10 seconds. The reaction was incubated at room temperature for 1-15 minutes, followed by addition of a reaction cessation solution (50 µl) which was mixed for 5-10 seconds. Solution absorbance was measured at 450 nm. The color is inversely proportional to the concentration of Aldosterone in the sample.

Figure 2:
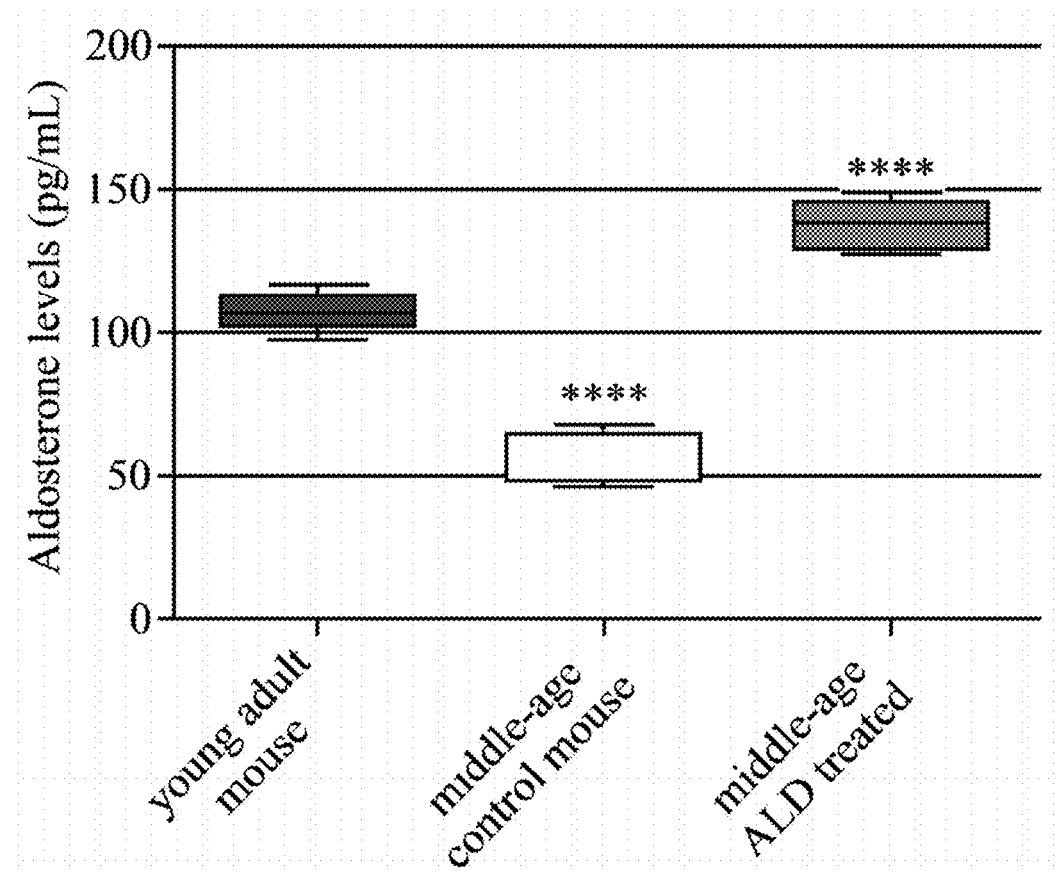
FIG. 2 is a graph showing serum ALD levels from middle age CBA/CaJ mice with or without ALD treatment for 120 days, compared to middle-age control mice. The serum ALD levels were determined in young adult and older (20-21 mon at the end of the treatment period) CBA/CaJ mice with and without ALD treatment (0.0016 mg/day continuous release through 120 days, one pellet for 60 days and subsequently a second pellet for 60 days), each group, n=5. Mean±SD for each group. * p<0.05,  p<0.01, * p<0.001, **** p<0.0001.

Serum aldosterone (ALD) levels declined as the mice aged, to approximately half their original values, which was statistically significant, from around 110 pg/mL in 2-4 month old mice to around 60 pg/mL in 12-18 month old mice, as seen in FIG. 1. Supplementing aging mice with ALD hormone treatments increased ALD levels such that the 120 day-old mice (middle age) showed the highest serum ALD levels, which showed statistically significant differences from the 2-4 month old and aging control mice, as seen in FIG. 2. However, the three subject groups were all within the normal ALD physiological range for mice.

Example 3

Spiral ganglion neuron (SGN) degeneration with age is an important biomarker of presbycusis-age-related hearing loss (ARHL). ARHL represents the top communication deficit and neurodegenerative disorder in aged populations. A relationship between aldosterone (ALD) serum levels and the severity of ARHL in old human subjects suggests that ALD may be involved in the etiology of ARHL (Tadros, et al., High Serum Aldosterone Levels Correlate with Lower Hearing Thresholds in Aged Humans: A Possible Protective Hormone against Presbycusis. Hearing Research. 2005; 209: 10-18). In addition, SGN density declines 30-60%, from apex to base in old CBA/CaJ mice compared to young adults (Tang, et al., Age-related hearing loss: GAB A, nicotinic acetylcholine and NMDA receptor expression changes in spiral ganglion neurons of the mouse. Neuroscience.2014; 259:184-93).

It has been shown that higher serum aldosterone (ALD) levels correlate with lower hearing thresholds in older human subjects (Tadros, et al., High Serum Aldosterone Levels Correlate with Lower Hearing Thresholds in Aged Humans: A Possible Protective Hormone against Presbycusis. Hearing Research. 2005; 209:10-18), and that serum aldosterone (ALD) levels declined between young adult and middle-aged in CBA/CaJ mice. As such, mouse inner ear auditory structure and function was studied with respect to ALD plasma levels.

CBA/CaJ mice (The Jackson Laboratory, Bar Harbor, Me.) were treated with aldosterone starting at 16-17 months of age. Treatment consisted of a subcutaneous implantation of a 120-day release pellet of D-aldosterone (0.0016 mg/day; Innovative Research of America, Sarasota, Fla.) behind the shoulder in ALD treatment mice (N=5), and same-age control mice (N=5) mice. The mice were kept in their home cages in the USF Vivarium room in the Global Center for Hearing & Speech Research, 12 hour light/dark cycle, 21 degrees C., in a relatively quiet environment with non-invasive auditory testing monthly. After the four month (120 day) course of treatment concluded, the mice were euthanized by injecting a commercial euthanasia solution, Euthasol®, (0.22 ml/kg) intraperitoneally. The depth of narcosis/anesthesia was assessed by using the interdigital pinch reflex. Death was confirmed by terminal phlebotomy/exsanguinations and perfusion.

After sacrifice, a cochlear modiolus (CM) was dissected from the temporal bone, & pooled together for measuring NKCC1 protein and mRNA expression. The other CM was prepared for immunohistochemistry as described below. Data was analyzed using one-way ANOVA, and two-way repeated measures ANOVA through GraphPad Prism 5.0 with protein level measurements (Δ Intensity=Background tissue intensity−experimental area intensity) (GraphPad Software, La Jolla, Calif.).

For Western blot and RT-PCR, cells were placed in RIPA buffer and sonicated. Protein concentration was measured using the Bradford method. Proteins were separated by SDS-PAGE. The antibodies used for the western blots were: Na+-K+-ATPase subunits and NKCC1 (Cell Signaling, Cambridge, Mass.). Total cellular RNA was extracted using the RNeasy Plus Mini Kit (74134). For RT-PCR, 10 ng of total cellular RNA was reverse transcribed and complementary DNA was amplified, using the Enhanced Avian HS RT-PCR-100 Kit (Sigma, HSRT20).

NKCC proteins play important roles in determining Na+ and K+ concentrations in key physiological systems, including cardiac, vascular, renal, nervous and sensory systems. NKCC levels and functionality are altered in certain disease states, and tend to decline with age. A sensitive, effective way of regulating NKCC protein expression has significant bio-therapeutic possibilities. ALD supplementation was analyzed for its ability to regulate NKCC1 protein expression. Application of ALD to a human cell line (HT-29) revealed that ALD can regulate NKCC1 activity and protein expression levels, quite sensitively and rapidly, as shown in (data not shown). Utilization of a specific inhibitor of mineralocorticoid receptors, eplerenone, implicated mineralocorticoid receptors as part of the ALD mechanism of action. Further experiments with cycloheximide (protein synthesis inhibitor) and MG132 (proteasome inhibitor) revealed that ALD can upregulate NKCC1 by increasing protein stability, i.e., reducing ubiquitination of NKCC1. Having a procedure for controlling NKCC1 protein expression opens the doors for therapeutic interventions for diseases involving the misregulation or depletion of NKCC proteins, for example in the cochlear lateral wall, during aging.

Figure 3A:
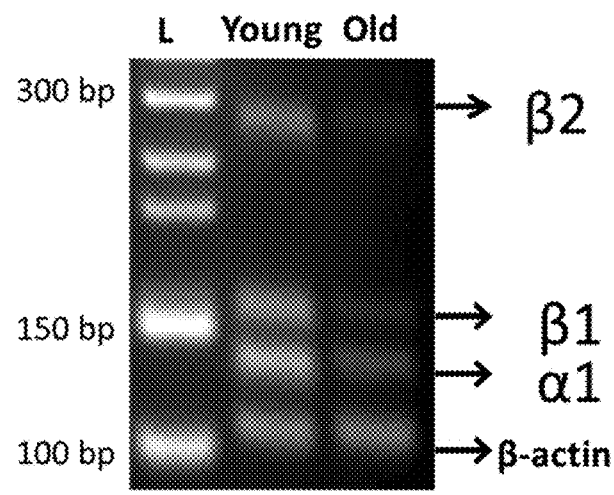
FIG. 3(A) shows the age-related decreases in Na, K-ATPase subunit expression in vivo. Cochleae were microdissected from young adult (3 month old) and old (30-33 month old) CBA/CaJ mice. The protein lysates and mRNA extraction were subjected to RT-PCR analysis. The RT-PCR blot shows lane L, a 100 by ladder. For the α1 subunit, the expected product of 141 by was observed; β1 subunit, 166 bp, and β2 subunit, 276 bp.
Figure 3B:
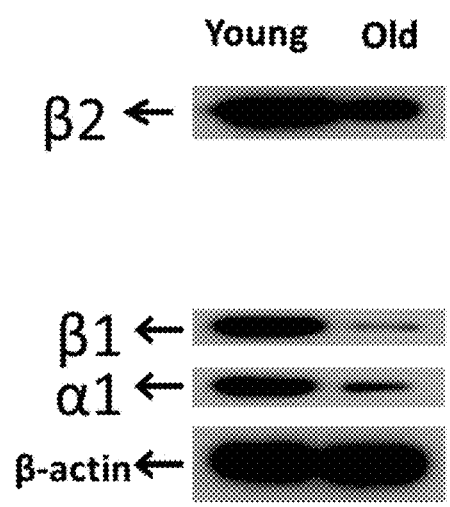
FIG. 3(B) shows the age-related decreases in Na, K-ATPase subunit expression in vivo. Cochleae were microdissected from young adult (3 month old) and old (30-33 month old) CBA/CaJ mice. The protein lysates and mRNA extraction were subjected to western blot. The western blot shows Na, K ATPase subunit protein expression.
Figure 3C:
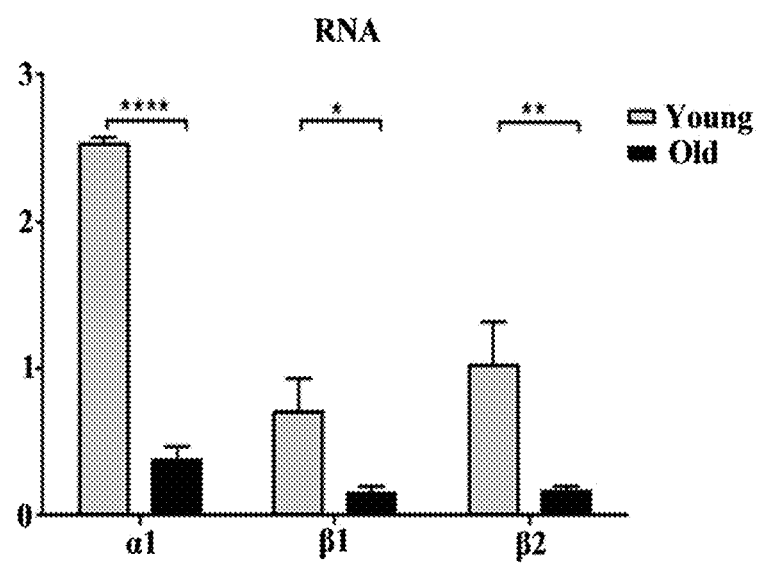
FIG. 3(C) shows the age-related decreases in Na, K-ATPase subunit expression in vivo. Cochleae were microdissected from young adult (3 month old) and old (30-33 month old) CBA/CaJ mice. The protein lysates and mRNA extraction were subjected to RT-PCR analysis (seen in FIG. 3(A)). The relative expression levels are summarized by the histogram from 3 independent experiments, using densitometric quantification. * p<0.05,  p<0.01, * p<0.001, **** p<0.0001.
Figure 3D:
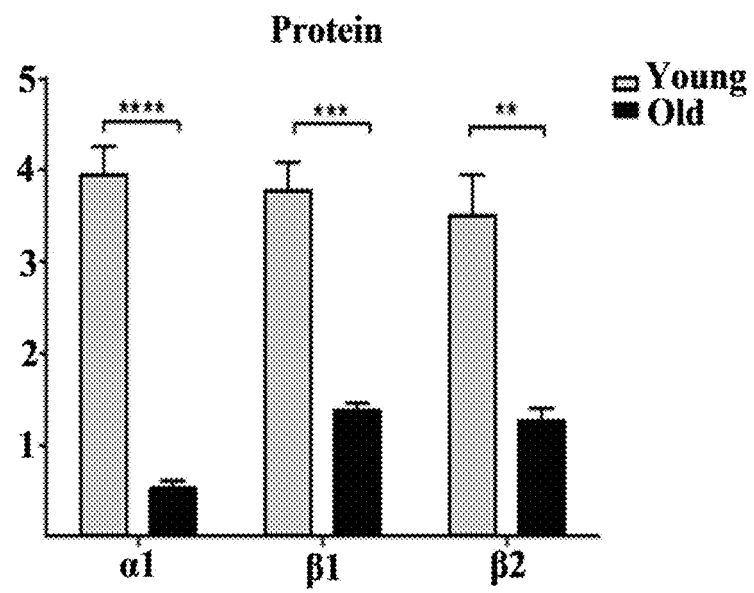
FIGS. 3(D) shows the age-related decreases in Na, K-ATPase subunit expression in vivo. Cochleae were microdissected from young adult (3 month old) and old (30-33 month old) CBA/CaJ mice. The protein lysates and mRNA extraction were subjected to western blot (seen in FIG. 3(A)). The relative expression levels are summarized by the histogram from 3 independent experiments, using densitometric quantification. * p<0.05,  p<0.01, * p<0.001, **** p<0.0001.

Along with declines in serum levels of ALD in aging CBA mice (FIGS. 1 and 2, above; and Zhu, X., et al. (2014). Aldosterone Reduces Spiral Ganglion Neuron Loss in Middle Age CBA/CaJ Mice. Assoc. Res. Otolaryngol. Abstr. 37, 7), NKCC1 and Na,K-ATPase gene and protein expression was found to decline with age in the CBA mouse cochlea, including the stria vascularis of the lateral wall (Ding, B., et al. (2014) Simultaneous declines in NKCC1 and Na, K-ATPase, but not Kir4.1 and KCNQ1/KCNE1, are found in the cochlear lateral wall of CBA/CaJ mice with age-related hearing loss. Soc. Neurosci. Abstr. 39). Both mRNA levels and protein levels of the subunits of Na, K-ATPase showed a clear decline in aged mice, which correlated among all the subunits, as seen in FIGS. 3(A) and (B). An analysis of the data indicated a relative expression patterns were statistically significant, as seen in FIGS. 3(C) and (D).

Figure 4:
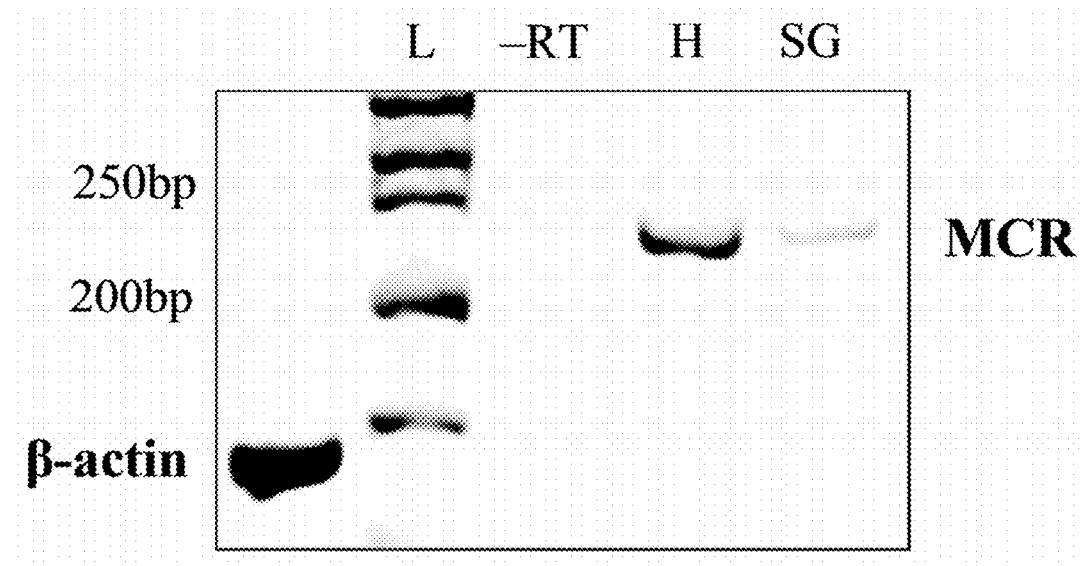
FIG. 4 is a blot showing the mineralocorticoid receptor (MCR) distribution in the cochlea of the young adult (3 mon) CBA/CaJ mouse. Multiplex RT-PCR was performed. The experiment includes the absence of reverse transcription (lane 1); L=Ladder, −RT=Negative Reverse Transcription, H=Heart, MD=Modiolus. The mRNA expression of MCR in tissue from spiral ganglion neurons, where the product of RT-PCR is about 245 bp.
Figure 5:
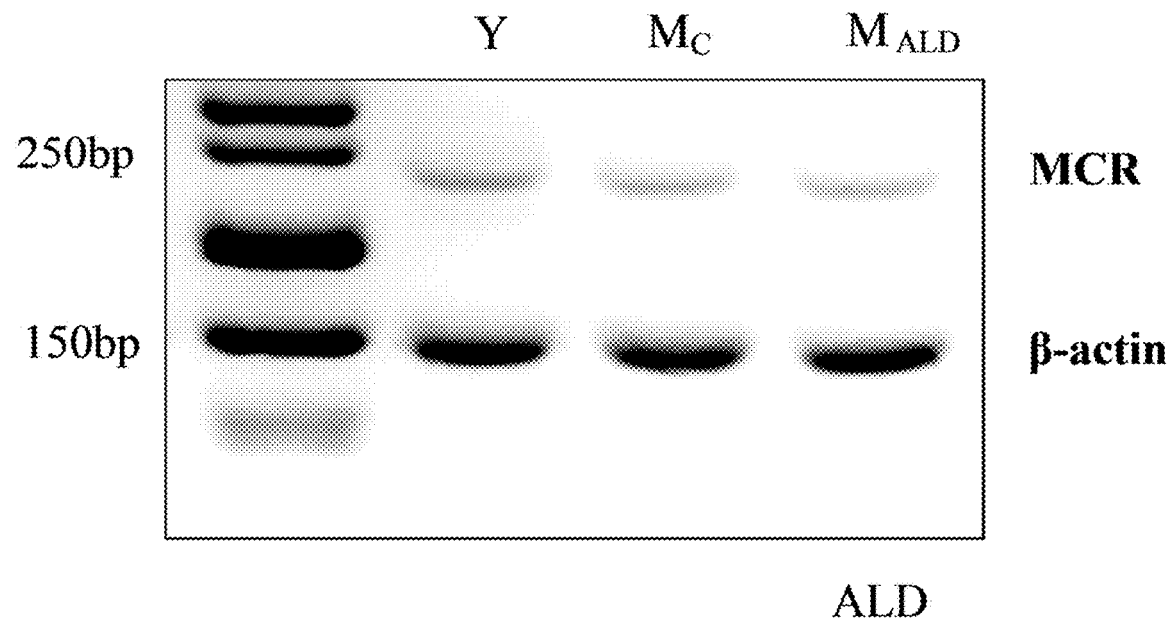
FIG. 5 is a blot showing MCR presence in spiral ganglion neurons from young adult (Y, 2-3 mon), and older (M, 20-21 mon) mice with and without aldosterone (ALD) treatment, demonstrating that ALD treatments upregulate MCR protein expression. mRNA gene expression of MCRs in young adult and older mice are similar. Y: Modiolar samples from young adult mice, M: Modiolar samples from older mice.

Aldosterone (ALD) binds with mineralocorticoid receptors (MCR). MCR distribution in cochlear modiolus (CM) was analyzed in young adult (3 month old) CBA/CaJ mice and multiplex RT-PCR performed to determine MCR mRNA expression in the spiral ganglion neurons, as seen in FIG. 4. Samples of the treatment mice were then compared to detect MCR mRNA in spiral ganglion neurons from the young CBA/CaJ (CBA) mouse (2-3 month old) compared to middle age mouse (20-21 month old) control (saline)-treated mouse and middle age ALD-treated mouse. Modiolar samples from young mouse showed slightly elevated MCR levels compared to Modiolar samples from middle-age control mice and the ALD-treated middle aged mice, as seen in FIG. 5.

Figure 6A:
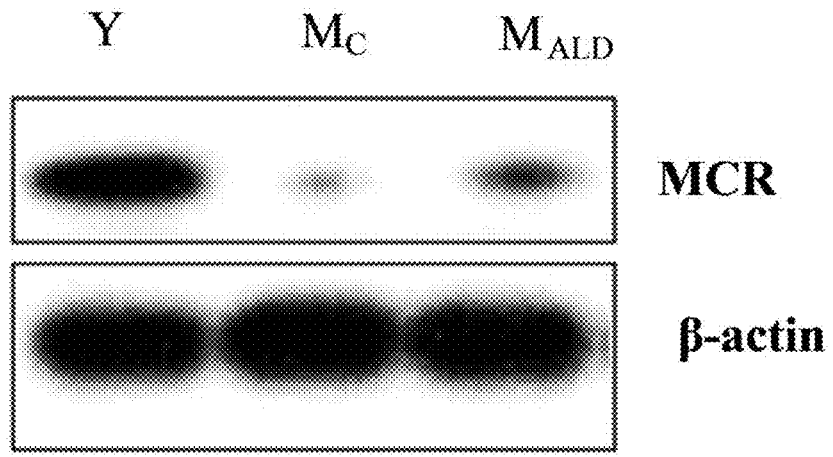
FIG. 6(A) is a blot showing MCR presence in spiral ganglion neurons from young adult (Y, 2-3 mon), and older (M, 20-21 mon) mice with and without aldosterone (ALD) treatment, demonstrating that ALD treatments upregulate MCR protein expression. The MCR protein expression level show representative sections for the MCR antibody staining Expression values from the blot were determined by densitometry analysis (MetaMorph Image Analysis System) of immunocytochemistry sections. The expression level is reported relative to the expression of beta-actin as the loading control.
Figure 6B:
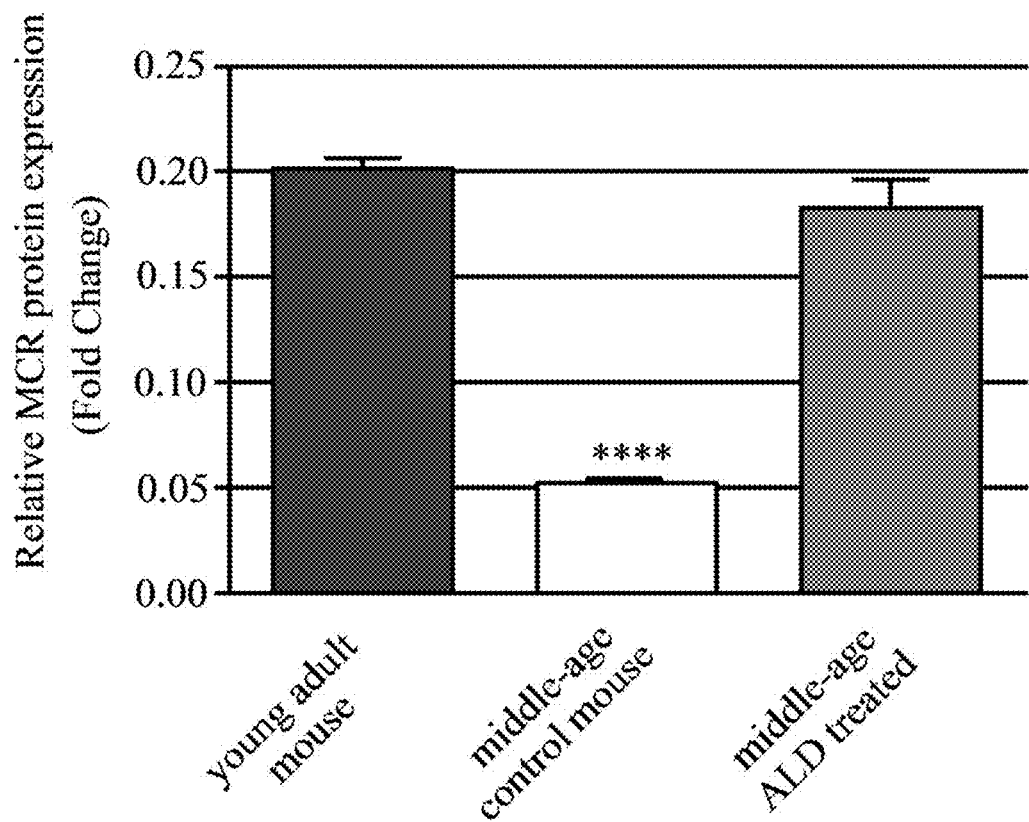
FIG. 6(B) is a densiometric graph of the blot showing MCR presence in spiral ganglion neurons from young adult (Y, 2-3 mon), and older (M, 20-21 mon) mice with and without aldosterone (ALD) treatment, demonstrating that ALD treatments upregulate MCR protein expression. The MCR protein expression level show representative sections for the MCR antibody staining. Expression values from the blot were determined by densitometry analysis (MetaMorph Image Analysis System) of immunocytochemistry sections, which are summarized in a bar graph summarizing the relative densities: Mean±SD for each group. (C) MCR protein expression in spiral ganglion neurons shown by western blots of modiolar tissue samples. The expression level is reported relative to the expression of beta-actin as the loading control.

MCR protein was run on a western blot to determine protein levels in spiral ganglion neurons from young adult (2-3 month old), and middle-aged (20-21 month old) mice, as seen in FIG. 6(A). The expression level of modiolar tissue samples was analyzed as relative to the expression of beta-actin as the loading control, showing ALD-treated middle age mice has similar MCR protein levels to young mice, which were both statistically significantly different from the middle age control mice, as seen in FIG. 6(B). This CM expression suggests that spiral ganglion neurons (SGNs) are possible targets for ALD hormonal influences.

For immunohistochemistry, mice were sacrificed, and one of the cochleae dissected, fixed in 4% paraformaldehyde in PBS overnight at 4° C., decalcification in 10% EDTA in PBS for a week at 4° C., and incubated in cryoprotection solution overnight at 4° C. The cochleae were embedded into degassed OCT overnight at 4° C., orientated into the cryomold with OCT degassed for 1 hour, then frozen at −80° C. Cryosectioning was performed at 5 μm per section. The cochlear cross sections were stained with hematoxylin and eosin (H&E) and MCR (H-300) (sc-11412, Santa Cruz Bio). The spiral ganglion neurons were counted by Metamorph imaging software (Molecular Devices, Center Valley, Pa. 18034-0610) and data analyzed by GraphPad Prism (GraphPad Software, Inc. La Jolla, Calif.).

Figure 7:
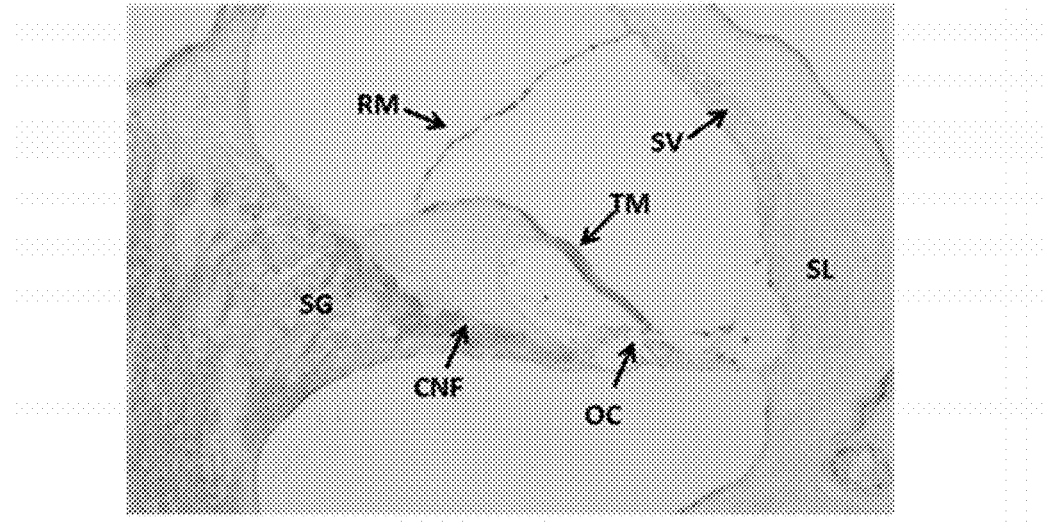
FIG. 7 is an image showing the mineralocorticoid receptor (MCR) distribution in the cochlea of the young adult (3 mon) CBA/CaJ mouse. The relative protein expression of MCRs was detected using immunohistochemistry staining. The regions include spiral ganglion (SG), cochlear nerve fibers (CNF), stria vascularis (SV), spiral ligament (SL), organ of Corti (OC), tectorial membrane (TM) and Reissner's membrane (RM).

Brain slices were obtained from 3 mon old CBA/CaJ mice and stained with an antibody to MCRs, as seen in FIG. 7. The relative protein expression of MCRs from the immunohistochemical staining was subjectively analyzed in regions include spiral ganglion, cochlear nerve fibers, stria vascularis, spiral ligament, organ of Corti, tectorial membrane and Reissner's membrane. Results are summarized in the Table.

TABLE

Immunostaining of the MCR in the CBA/CaJ of young adult mouse cochlea

| Cochlea Region | Intensity |
|---|---|
| Spiral Ganglion (SG) | ++ |
| Cochlear Nerve Fibers (CNF) | +++ |
| Stria Vascularis (SV) | ++ |
| Spiral Ligament (SL) | ++ |
| Organ of Corti (OC) | ++ |
| Tectorial Membrane (TM) | +++ |
| Reissner's Membrane (RM) | +++ |

The immunoreactivity is based on a subjective estimated scale:
+ = weak staining,
++ = moderate staining,
+++ = strong staining.

Figure 8:
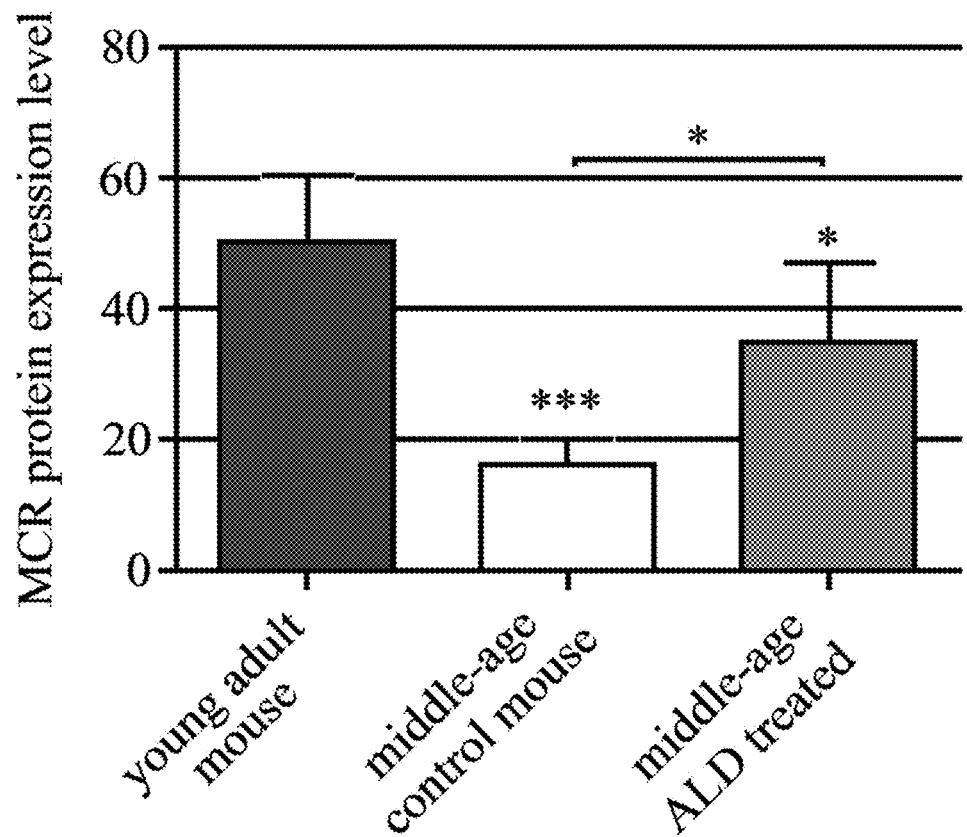
FIG. 8 is a graph showing MCR presence in spiral ganglion neurons from young adult (2-3 mon), and older middle-aged (20-21 mon) mice with and without aldosterone (ALD) treatment, demonstrating that ALD treatments upregulate MCR protein expression. MCR protein expression in spiral ganglion neurons shown by western blots of modiolar tissue samples. The expression level is reported relative to the expression of beta-actin as the loading control. * p<0.05,  p<0.01, *p<0.001, ****p<0.0001.

Levels of staining for MCR presence in young adult and middle-aged mice was determined by densitometry analysis (MetaMorph Image Analysis System) of immunocytochemistry sections. The relative densities from densitometry measurements were determined, as seen in in FIG. 8, showing young mice had the highest level of MCR expression with middle age mouse controls showing approximately ⅓ the expression levels of the young mice. ALD treatment of the middle age partially rescued the expression levels seen in the young adult.

Figure 9:
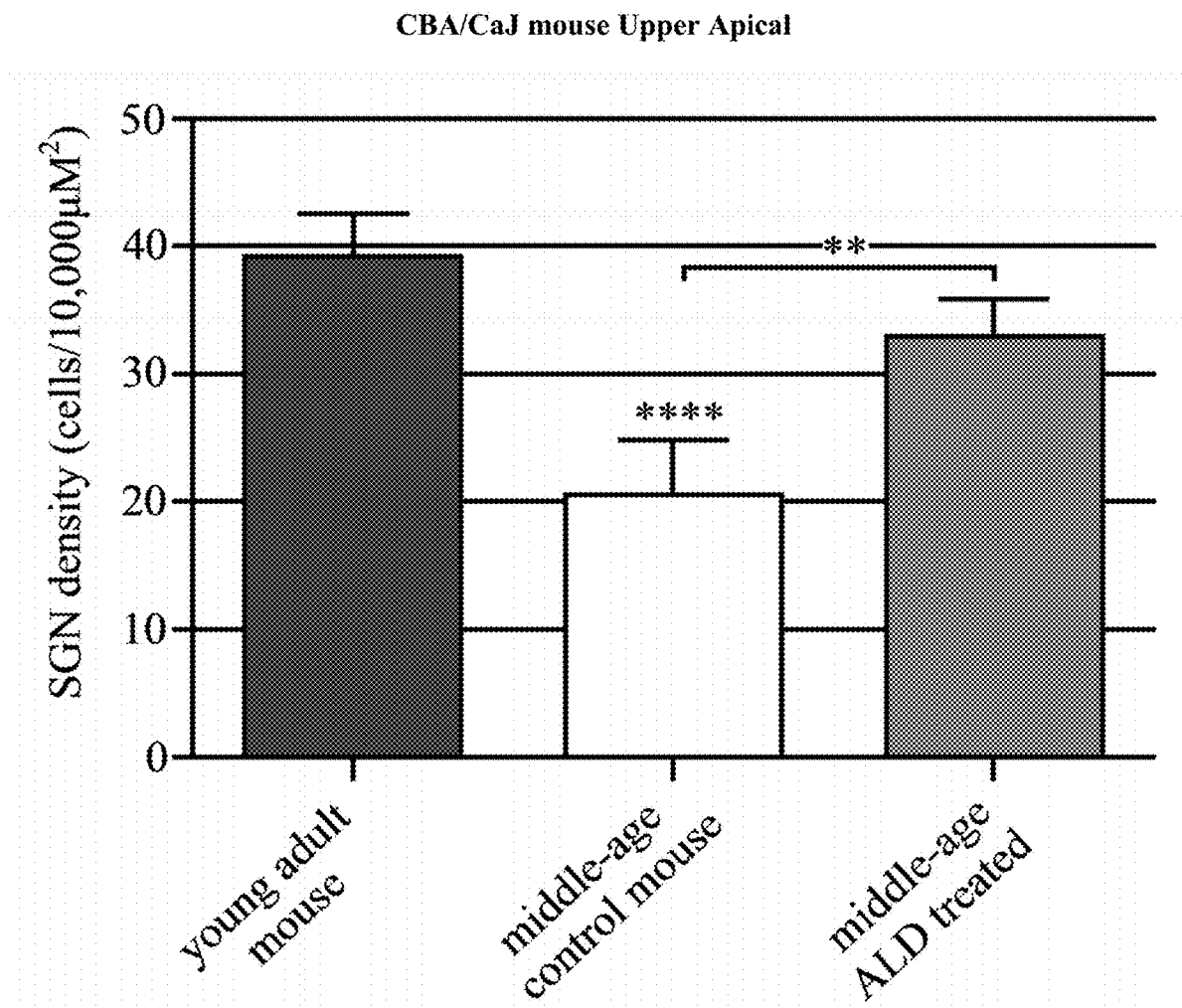
FIG. 9 is a graph showing the SGN cell density as measured at the upper apical section of the cochlea. Cochlea section-thickness was 5 μm. The SGNs were counted using light microscopy at a magnification of 20×1.6. The SGN cell density was lower in each turn in the non-ALD treatment, middle aged CBA/CaJ group compared to the same-age ALD treated group. * p<0.05,  p<0.01, * p<0.001, **** p<0.0001.
Figure 10:
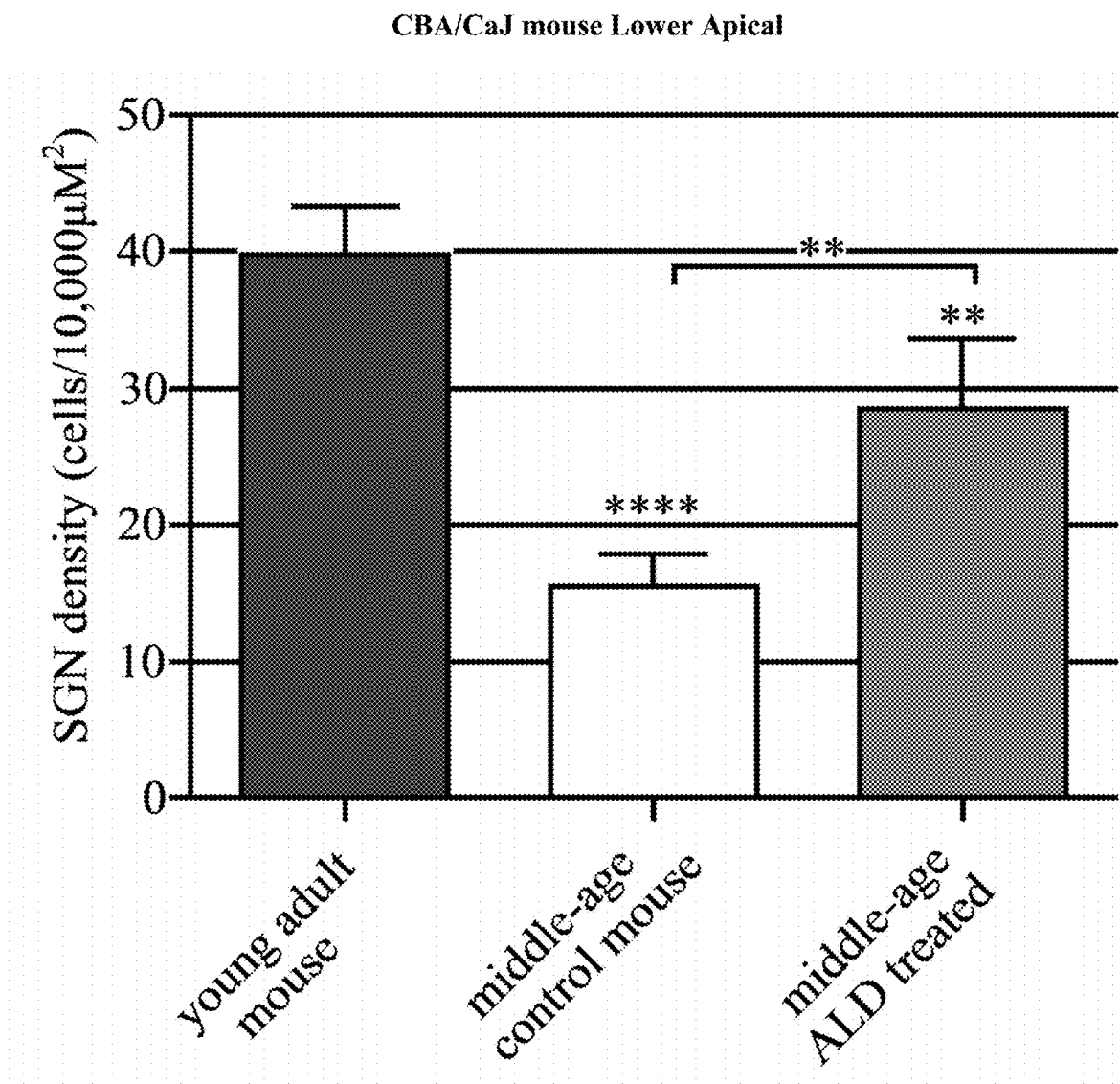
FIG. 10 is a graph showing the SGN cell density as measured at the lower apical section of the cochlea. Cochlea section-thickness was 5 μm. The SGNs were counted using light microscopy at a magnification of 20×1.6. The SGN cell density was lower in each turn in the non-ALD treatment, middle aged CBA/CaJ group compared to the same-age ALD treated group. * p<0.05,  p<0.01, * p<0.001, **** p<0.0001.
Figure 11:
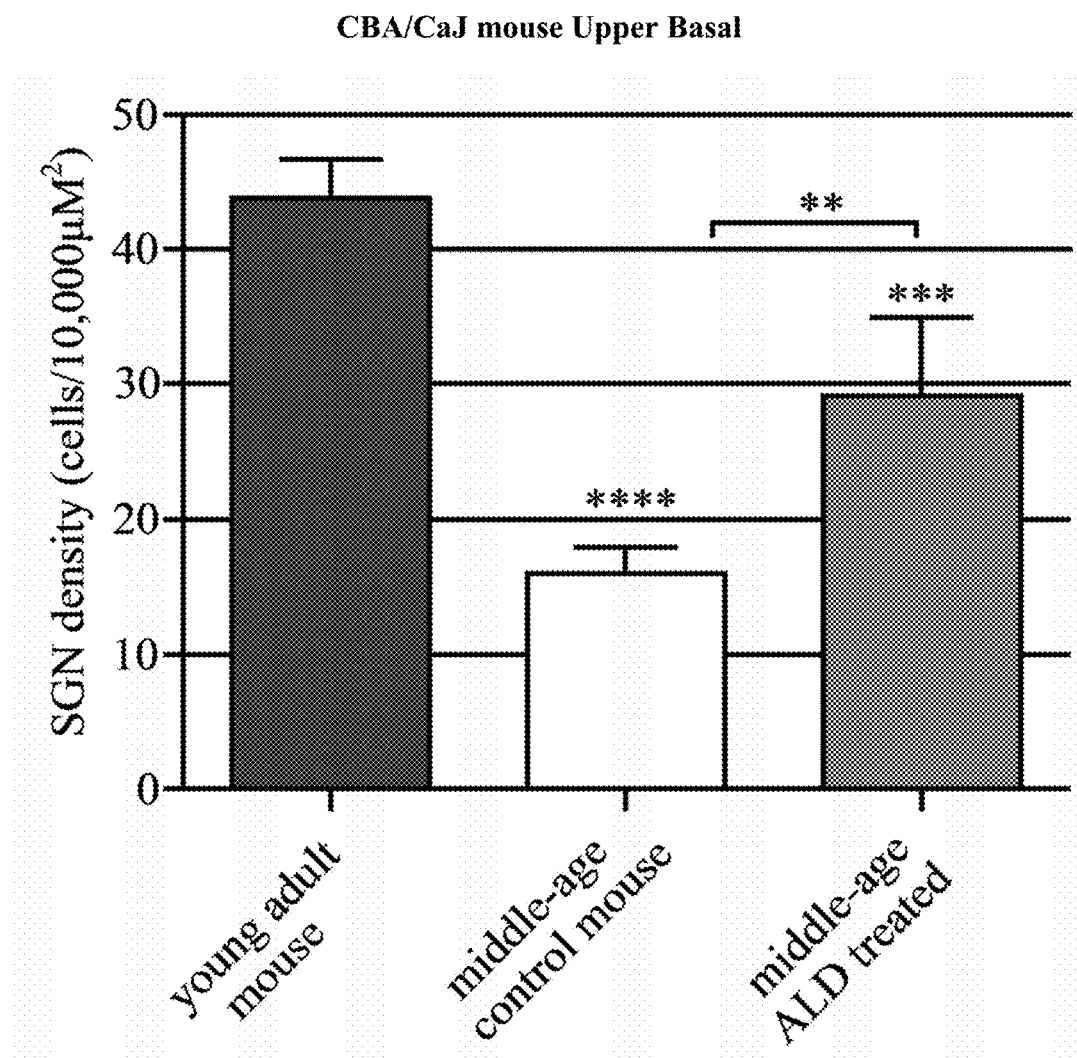
FIG. 11 is a graph showing the SGN cell density as measured at the upper basall section of the cochlea. Cochlea section-thickness was 5 μm. The SGNs were counted using light microscopy at a magnification of 20×1.6. The SGN cell density was lower in each turn in the non-ALD treatment, middle aged CBA/CaJ group compared to the same-age ALD treated group. * p<0.05,  p<0.01, *p<0.001, **** p<0.0001.
Figure 12:
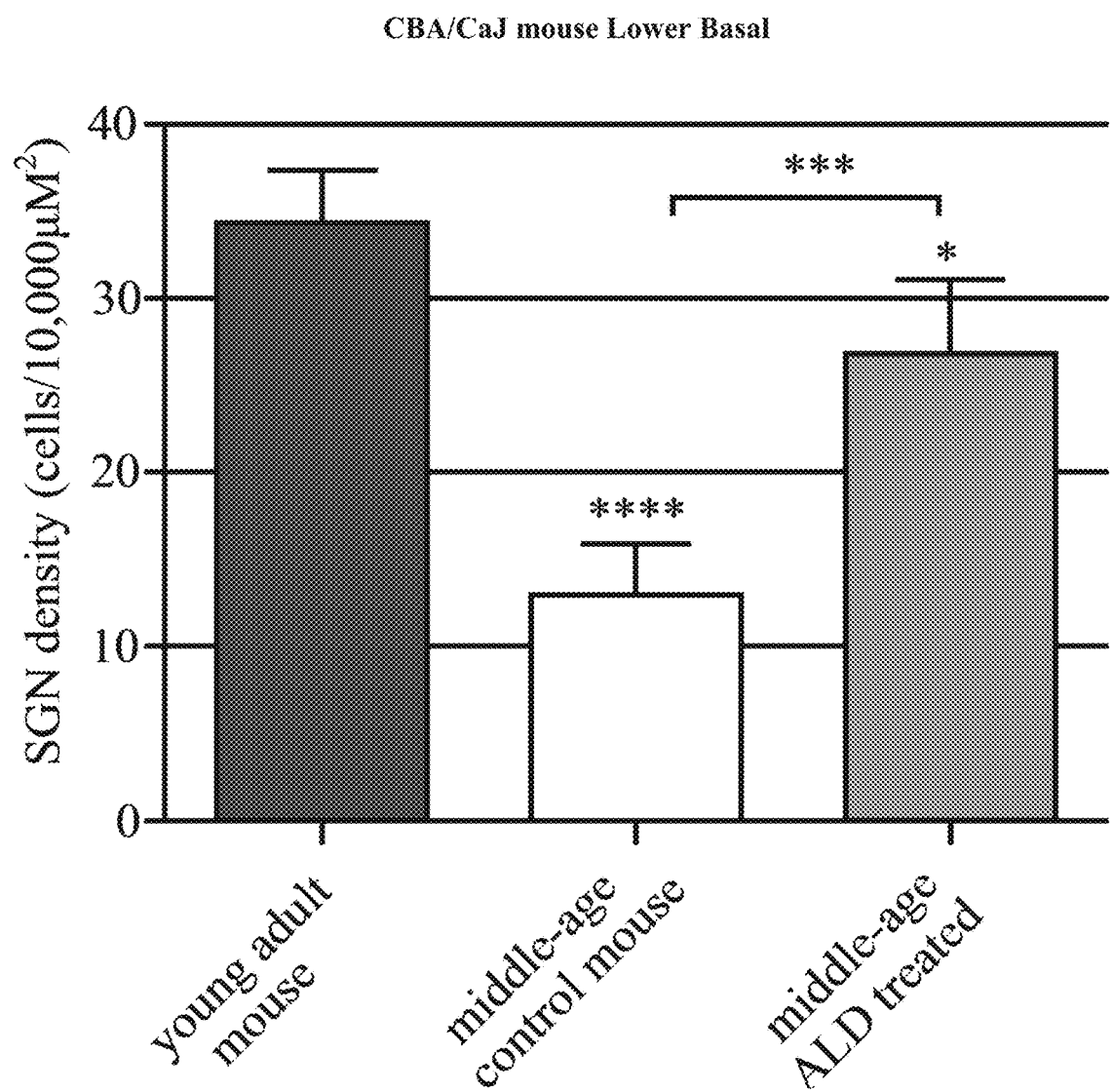
FIG. 12 is a graph showing the SGN cell density as measured at the lower basal section of the cochlea. Cochlea section-thickness was 5 μm. The SGNs were counted using light microscopy at a magnification of 20×1.6. The SGN cell density was lower in each turn in the non-ALD treatment, middle aged CBA/CaJ group compared to the same-age ALD treated group. * p<0.05,  p<0.01, *p<0.001, **** p<0.0001.

Spiral ganglion neuron (SGN) cell density was measured from 4 different topographical area, comparing ALD-treated middle-aged mice to age-matched controls. H&E staining showed that for the ALD treatment group, SGN density was higher in the upper apical, as seen in FIG. 9, lower apical, seen in FIG. 10, upper basal, seen in FIG. 1, and lower basal, seen in FIG. 12, regions than the untreated control mice throughout the cochlea. Further, this increase in SGN is correlated with ABR threshold shifts (shown below) in the same mice. The experimental group also showed an upregulation of mineralocorticoid receptors, in SGNs of the experimental mice relative to controls. Lastly, prepulse inhibition, indicate provocative increases in auditory temporal processing in our ALD-treated aging CBA mice (Halonen et al. 2014).

ALD appears to play a key role in preserving hearing and for modulating SGN degeneration stria vascularis degeneration in the aging cochlea. ALD supplementation shows use in preserving hearing, reducing SGN degeneration, and stimulating MCR upregulation in the aging cochlea.

Example 4

Initial investigations have implicated the mineralocorticoid, steroid hormone ALD synthesized in the glomerulosa of the adrenal gland, as a regulator of NKCC1. For instance, when adrenalectomized rats received a multiday treatment of ALD, there was a 63% increase in NKCC1 activity as measured by bumetanide-sensitive efflux of $^{86}Rb$ for vascular smooth aortic muscle (Jiang, et al., Aldosterone regulates the Na—K-2Cl cotransporter in vascular smooth muscle. *Hypertension* 41: 1131-1135, 2003). Interestingly, application of ALD did not elevate NKCC1 transcripts as determined by real-time polymerase chain reaction. Additionally, NKCC1-knockout mice have deficient or abnormal responses to ALD (Kim, et al., Salt sensitivity of blood pressure in NKCC1-deficient mice. *Am J Physiol Renal Physiol* 295: F1230-F1238, 2008., Wall, et al., Hypotension in NKCC1 null mice: role of the kidneys. *Am J Physiol Renal Physiol* 290: F409-F416, 2006). ALD can exert its action by binding to mineralocorticoid receptors (type I) to form a complex that interacts with nuclear DNA to exert gene transcription and protein synthesis (Phakdeekitcharoen, et al., Aldosterone increases Na$^+$—K$^+$ ATPase activity in skeletal muscle of patients with Conn's syndrome. *Clin Endocrinol (Oxf)* 74: 152-159, 2010, Tsuchiya, et al., Aldosterone-dependent regulation of Na—K-ATPase subunit mRNA in the rat CCD: competitive PCR analysis. *Am J Physiol Renal Fluid Electrolyte Physiol* 271: F7-F15, 1996). The present study tested the hypothesis that ALD can directly and precisely increase NKCC1 expression.

Cell culture and buffers. Human colon adenocarcinoma epithelial HT-29 cells (obtained from the laboratory of Dr. Edward Seto, Moffitt Cancer Res. Center, Tampa Fla.) were utilized in the present investigation, since they express NKCC1, which can be effectively detected in these cells using straightforward protein techniques (more complicated procedures involving manipulation of transfected constructs not necessary), and since previous reports have demonstrated HT-29 utility for being a representative epithelial cell line for investigations of cell signaling and transductional factors and pathways (Cox, et al., Effects of autonomic agonists and immunomodulatory cytokines on polymeric immunoglobulin receptor expression by cultured rat and human salivary and colonic cell lines. *Arch Oral Biol* 52: 411-416, 2007). These include, for example, studies of COMM domain-containing protein 1, which is involved in NKCC1 ubiquitination and transcriptional regulation of epithelial Na$^+$ channels (ENaC) located in the apical membrane of polarized epithelial cells, in particular, cells in the colon, kidney, and lung, by ALD (Cohen, et al., Induced differentiation in HT29, a human colon adenocarcinoma cell line. *J Cell Sci* 112: 2657-2566, 1999, Epple, et al., Early aldosterone effect in distal colon by transcriptional regulation of ENaC subunits. *Am J Physiol Gastrointest Liver Physiol* 278: G718-G724, 2000, Smith, et al., COMMD1 interacts with the COOH terminus of NKCC1 in Calu-3 airway epithelial cells to modulate NKCC1 ubiquitination. *Am J Physiol Cell Physiol* 305: C133-C146, 2013). HT-29 cells were grown in DMEM media (Invitrogen, Carlsbad Calif.) with 10% FBS and antibiotics. Cells were grown in a humidified 95%/5% $CO_2$ incubator at 37° C. Experiments were performed at 70-80% confluence.

$^{86}Rb$ uptake. Similar to previous studies of NKCC1 activity (Gagnon & Delpire, Molecular determinants of hyperosmotically activated NKCC1-mediated K_/K_exchange. *J Physiol* 588: 3385-3396, 2010), cells were plated on six-well dishes and incubated at 37° C./5% $CO_2$ until confluent. For the uptake, cells were first washed twice with 1 ml of isosmotic saline (140 mM NaCl, 5 mM KCl, 2 mM $CaCl_2$, 0.8 mM $MgSO_4$, 5 mM glucose, 5 mM HEPES buffered to pH 7.4, and 300.5 mosM). Cells were then preincubated for 15 min in 1 ml of the same isosmotic saline plus 1 mM ouabain (Sigma)±20 µM bumetanide (Sigma, St. Louis Mo.). The preincubation solution was then aspirated and replaced with an identical solution containing 1 µCi of $^{86}Rb$ and 1 mM ouabain±20 µM bumetanide. Four 5 µl aliquots of flux solution were sampled at the beginning of each $^{86}Rb$ uptake condition and used as standards. After a 20-min uptake, the radioactive solution was aspirated, and the cells were washed three times with 1 ml of ice-cold solution, lysed for 1 h with 500 µl of 0.25 N NaOH, and neutralized with 250 µl of glacial acetic acid. $^{86}Rb$ tracer activity was measured by using 150 µl of lysate for γ-scintillation counting. NKCC1 flux was expressed in millimoles of K$^+$ per micrograms of protein per minute.

Relative quantitative RT-PCR. Total RNA was extracted using the RNAeasy Mini Kit (Qiagen, Valencia Calif.). Quantitative reverse transcription-polymerase chain reaction (qRT-PCR) was performed using two methods: per manufacturer's suggestion using the Enhanced Avian HS RT-PCR-100 Kit (HSRT20; Sigma) and the Fast Real-Time PCR System with their SYBR Green PCR Master Mix (7900HT; Applied Biosystems, Carlsbad Calif.). Primers used for qRTPCR were as follows:

```
For β-actin,
                                    (SEQ ID No. 1)
5-CCTGGCACCCAGCACAAT
(sense)
and (SEQ ID No. 2)
5'-GGGCCGGACTCGTCATAC
(antisense);
and For NKCC1,
                                    (SEQ ID No. 3)
5'-ACCTTCGGCCACAACACCATGGA
(sense)
and (SEQ ID No. 4)
5'-ACCACAGCATCTCTGGTTGGA
(antisense).
```

The semiquantitative qRT-PCR reaction took place at 45° C. for 50 min. The competition between primer sets was excluded by adjusting the reaction condition.

Then, the primer products were PCR amplified directly. A first cycle of 10 min. at 95° C., 45 s at 65° C., and 1 min at 72° C. was followed by 45 s at 95° C., 45 s at 65° C., and 1 min at 72° C. for 25 cycles. The conditions were chosen so that the RNAs analyzed were in the exponential phase of amplification. Each set of reactions always included a no-sample negative control. We usually performed a negative control containing RNA instead of cDNA to rule out genomic DNA contamination.

The real-time RT-PCR reaction mixture was prepared using the SYBR-Green PCR Master Mix. Thermal cycling conditions were the same as in the semiquantitative method. Amplification specificity was checked using melting curves. Both negative and positive controls were included in each PCR reaction. All assays were carried out three times as independent PCR runs for each cDNA sample. Gene expression was referenced to the expression of β-actin as the housekeeping gene. Each gene expression level was normalized with respect to β-actin mRNA content. Calculations of expression were performed with the 2ΔΔCT method (Bustin, et al., Quantitative real-time RTPCR—a perspective. *J Mol Endocrinol* 34: 597-601, 2005).

Western blot. Cell lysates were prepared in RIPA buffer (Pierce 89901; Thermo Scientific, Waltham, Mass.) with protease inhibitor cocktail (78430; Thermo Scientific). Cell samples were homogenized in buffer, followed by centrifugation at 2,000 rpm for 10 min at 4° C. Supernatants were subjected to Western blot analysis by loading 200 μg of protein per lane, after the protein concentrations were determined by Bradford protein assay. Proteins were fractionated by SDS-PAGE gel electrophoresis and transferred to a PVDF blotting membrane (Whatman, Piscataway, N.J.). The blot was incubated with primary antibodies against β-actin and Na—K-2Cl cotransport protein (Cell Signaling, Danvers Mass.); primary antibodies for p-SGK1, SGK1, pNedd4-2, and Nedd4-2 were utilized (concentration 1:1,000). The secondary antibody was horseradish peroxidaseconjugated goat anti-rabbit IgG (1:2,000; Cell Signaling).

Tl-uptake in single cells for the detection of NKCC1 activity. To measure NKCC1 activity, we used a fluorescence assay to assess cotransporter activity in single isolated HT-29 cells (Delpire & Austin, Kinase regulation of $Na^+$—$K^+$-$2Cl^-$ cotransport in primary afferent neurons. *J Physiol* 588: 3365-3373, 2010, Geng, et al., The Ste20 kinases SPAK and OSR1 regulate NKCC1 function in sensory neurons. *J Biol Chem* 284: 14020-14028, 2009, Weaver, et al., A thallium-sensitive, fluorescence-based assay for detecting and characterizing potassium channel modulators in mammalian cells. *J Biomol Screen* 9: 671-677, 2004). HT-29 cells were incubated at 37° C./5% $CO_2$ for 24 h before use. For the uptake experiment, thallium was used as the tracer for the $K^+$ (FluxORTM Thallium Detection Kits; Invitrogen). Cells were first loaded with the thallium-sensitive FluxORTM dye (1×) in a hypotonic (275.5 mosM) low chloride solution (125 mM NaMeSO3, 2 mM KCl, 2 mM $CaCl_2$, 0.8 mM $MgSO_4$, 5 mM glucose, and 20 mM HEPES) plus 1× PowerLoad concentrate and 2.7 mM probenecid (supplied by the kit) for 90 min. The loading solution was then aspirated, and cells were washed three times with the same solution to remove excess dye. Cells were then preincubated for 10 min using 1 ml of the same saline containing 1 mM ouabain and 2.7 mM probenecid in the presence or absence of 20 μM bumetanide (Sigma). For the detection of fluorescence, the preincubation solution was removed, and the cells were treated with a 340.5 mosM hypertonic stimulus solution containing the following (in mM): (2.8 $TISO_4$, 140 NaCl, 2 KCl, 2 $CaCl_2$, 0.8 MgSO4, 5 glucose, 20 HEPES, 27 sucrose, 1 ouabain, and 2.7 probenecid) in the presence or absence of 20 μM bumetanide. Images were made using a x40× objective inverted florescent microscope at 488-nm excitation wavelength. HT-29 cells were loaded with the thallium-sensitive dye FluxOR (Invitrogen). FluxOR fluorescence (excitation/emission: 488/525 nm) was recorded after 90 s upon addition of 2.8 mM T1504 to the external medium. The difference between the two measurements, made with and without bumetanide treatment, represents the bumetanide-sensitive component of the $Tl^+$ uptake, mediated by NKCC1.

Immunoprecipitation (autoubiquitination assay) and western blot analysis. An autoubiquitination assay was followed (Garg, et al., Effect of the Na—K-2Cl cotransporter NKCC1 on systemic blood pressure and smooth muscle tone. *Am J Physiol Heart Circ Physiol* 292: H2100-H2105, 2007). Cell extracts were prepared in a modified radioimmunoprecipitation assay 1 (RIPA) buffer, containing the following (in mM): 50 Tris·HCl at pH 7.4, 150 NaCl, 1 EDTA, and 1 dithiothreitol with 1% Nonidet P-40, 0.1% SDS; in a 1:200-diluted protease inhibitor cocktail (Sigma), containing the following (in mM): 1 PMSF, 10 NEM, and 0.1 iodoacetamide Immunoprecipitations were accomplished using a rabbit polyclonal anti-NKCC1 antibody (Cell Signaling). Antibody was bound to lysate with endogenous NKCC1, and then beads were added. Bound proteins were eluted in 1× SDS sample buffer, fractionated on an SDS-polyacrylamide gel, transferred onto a PVDC membrane (GE Healthcare, Piscataway, N.J.), and immunoblotted with anti-ubiquitin antibody visualized using enhanced chemiluminescence detection reagents (Pears, Shelton Conn.) according to the manufacturer's instructions.

Immunoblotting with anti-ubiquitin antibody was performed as described above.

Sources. Chloroquine, an agent that impairs lysosomal acidification (lysosome inhibitor), MG-132 (proteasome inhibitor), cycloheximide (translation inhibitor), and GSK650394 (SGK inhibitor) were purchased from Sigma (St. Louis, Mo.). The polyclonal antibodies to NKCC1 and β-actin were purchased from Cell Signaling (Cambridge, Mass.); and the polyclonal antibodies to p-SGK (Thr256) and SGK from Santa Cruz (Dallas, Tex.). The polyclonal antibodies to p-Nedd4-2 (S328), Nedd4-2, and LAMP2 were purchased from Abcam (Cambridge, Mass.), and the polyclonal antibody to LC3 was purchased from Novus Biologicals (Littleton, Colo.).

Statistical analysis. Images from films were imported into Adobe Photoshop (v 5.0), and further processed using Adobe Photoshop CS and ImageJ (National Institutes of Health) for the densitometry analysis. Data are reported as means±SD. Statistical analyses were performed with PRISM 4.0 (GraphPad Software, San Diego Calif.). Differences were analyzed with a one- or a two-way repeated measures ANOVA as appropriate or a two-way ANOVA followed by Bonferroni post hoc analyses that were corrected for multiple comparisons. Values of $P < 0.05$ were considered significant.

Figure 13:
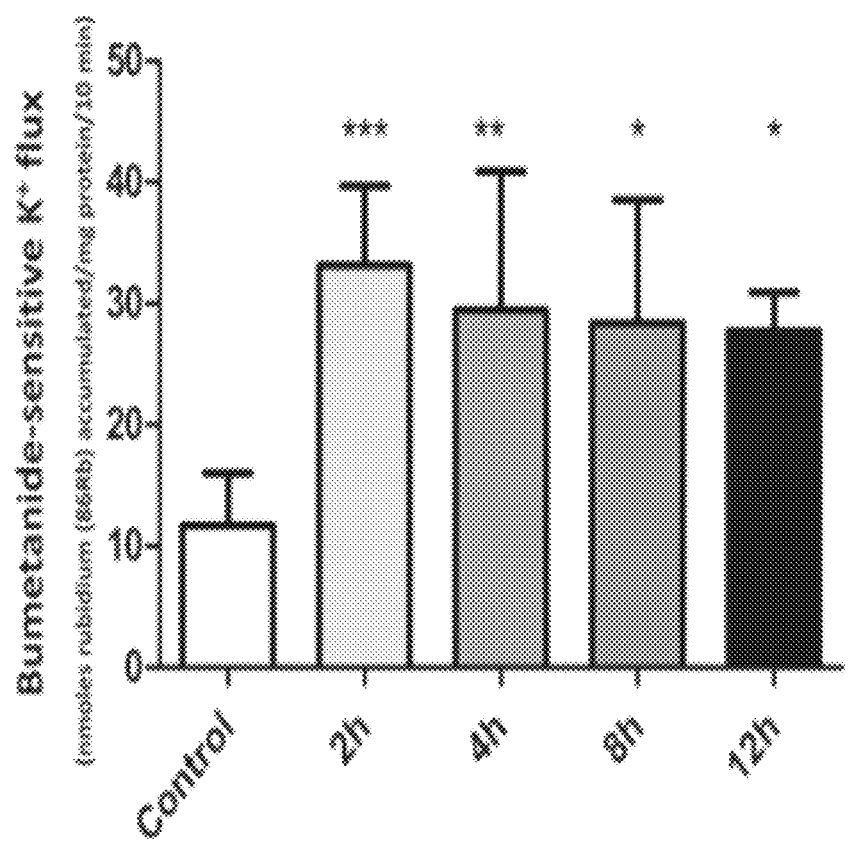
FIG. 13 is a graph showing that Aldosterone (ALD) increases activity levels and protein expression of $Na^+$—$K^+$-$2Cl^-$ cotransport protein (NKCC1). NKCC1 activity was determined through 86Rb uptake, which was measured in an isosmotic solution containing 1 mM ouabain, at 2, 4, 8, and 12 h after ALD administration. Bar graph results are means±SD from 3 independent experiments, the ordinate represents relative expression, defined as expression level relative to the time 0 or dosage point. Statistical significance: * p<0.05,  p<0.01, * p<0.001, **** p<0.0001.
Figure 14A:
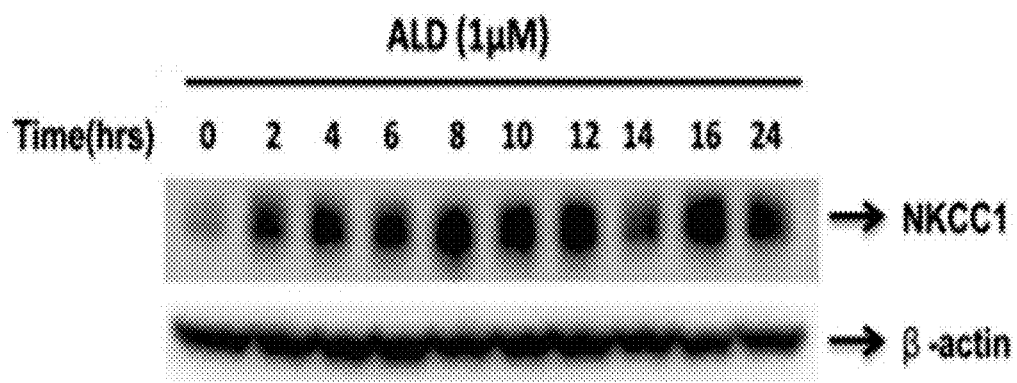
FIG. 14(A) is a blot showing aldosterone (ALD) increases activity levels and protein expression of $Na^+$—$K^+$-$2Cl^-$ cotransport protein (NKCC1). HT-29 cells were treated with ALD for the times and doses indicated and lysed by RIPA buffer with cocktail protein inhibitors; proteins were resolved by SDS-PAGE. Western blot was probed sequentially with antibodies to NKCC1 and β-actin as the control. ALD treatment increases NKCC1 protein expression. The time frame of upregulation is from 2 h up to 24 h after application of ALD (1 µM).
Figure 14B:
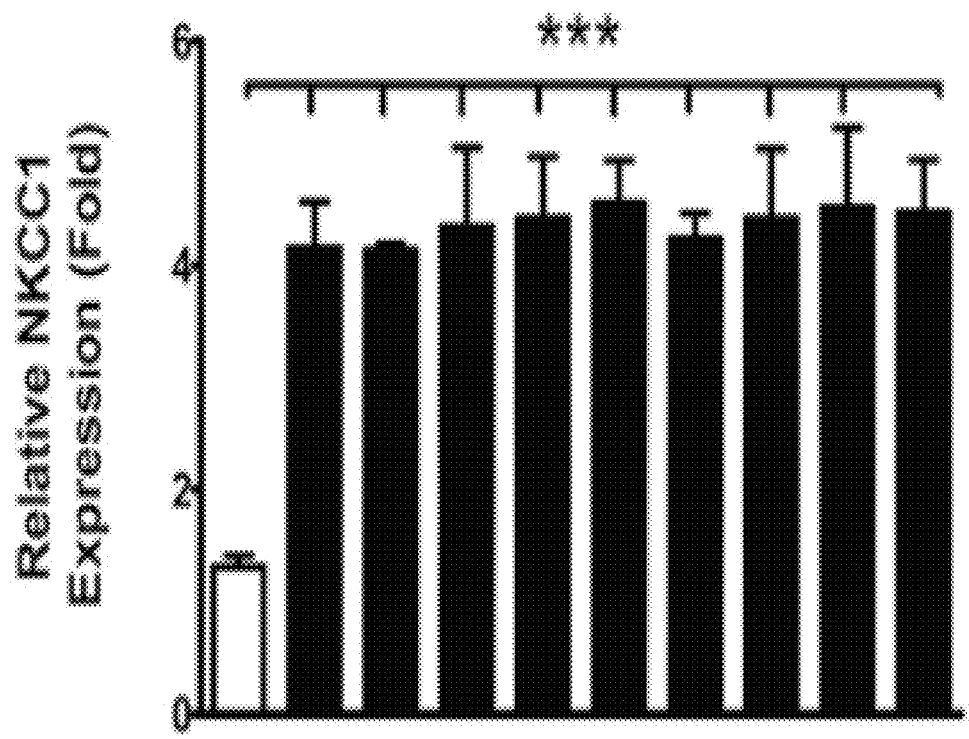
FIG. 14(B) is a graph showing aldosterone (ALD) increases activity levels and protein expression of $Na^+$—$K^+$-$2Cl^-$ cotransport protein (NKCC1) from FIG. 14(A). HT-29 cells were treated with ALD and proteins were resolved by SDS-PAGE. Densiometric results of the Western blot are shown in bar graph results as a means±SD from 3 independent experiments, the ordinate represents relative expression, defined as expression level relative to the time 0 or dosage point. Open bar: control, nontreated sample; the vehicle was 100% alcohol, in which the ALD and eplerenone were dissolved. Statistical significance: * p<0.05,  p<0.01, * p<0.001, **** p<0.0001.
Figure 15A:
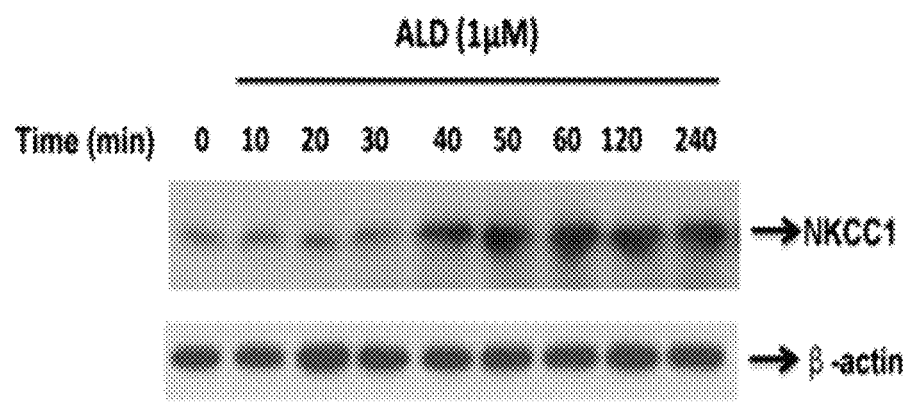
FIG. 15(A) is a blot showing aldosterone (ALD) increases activity levels and protein expression of $Na^+$—$K^+$-$2Cl^-$ cotransport protein (NKCC1). HT-29 cells were treated with ALD (1 nM) and tested for induction after administration. Cells were lysed by RIPA buffer with cocktail protein inhibitors; proteins were resolved by SDS-PAGE. Western blot was probed sequentially with antibodies to NKCC1 and β-actin as the control. Results show induction starts 30-40 min after treatment ALD treatment increases NKCC1 protein expression.
Figure 15B:
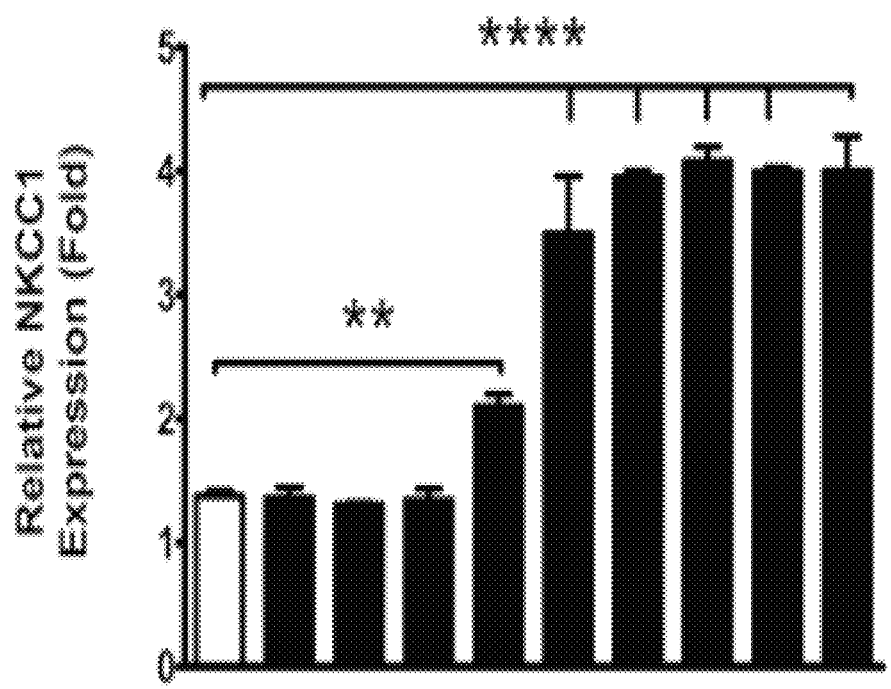
FIG. 15(B) are a blot and graphs showing aldosterone (ALD) increases activity levels and protein expression of $Na^+$—$K^+$-$2Cl^-$ cotransport protein (NKCC1). HT-29 cells were treated with ALD (1 µM) and tested for induction after administration as shown in FIG. 15(A). Densiometric results from the blot showing bar graph results as a means±SD from 3 independent experiments, the ordinate represents relative expression, defined as expression level relative to the time 0 or dosage point. Open bar: control, nontreated sample; the vehicle was 100% alcohol, in which the ALD and eplerenone were dissolved. Statistical significance: * p<0.05,  p<0.01, * p<0.001, **** p<0.0001.
Figure 16A:
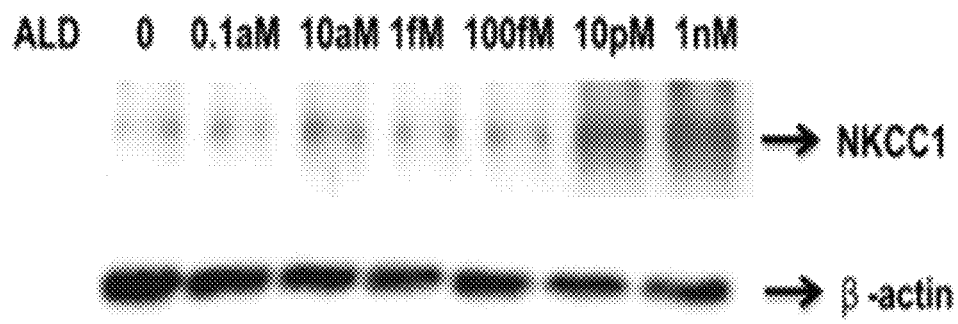
FIG. 16(A) is a blot showing aldosterone (ALD) increases activity levels and protein expression of $Na^+$—$K^+$-$2Cl^-$ cotransport protein (NKCC1). HT-29 cells were treated with ALD for the times and doses indicated and lysed by RIPA buffer with cocktail protein inhibitors; proteins were resolved by SDS-PAGE. (A) Western blot was probed sequentially with antibodies to NKCC1 and β-actin as the control. Increases in NKCC1 protein levels are mediated via the activation of mineralocorticoid receptors (MR). HT-29 cells were treated with or without a specific inhibitor of MR, eplerenone (20 µM), and then applied with 1 µM ALD for the indicated times. NKCC1 protein expression was detected in cell lysates by a Western blot, using antibodies to NKCC1, and β-actin as a loading control.
Figure 16B:
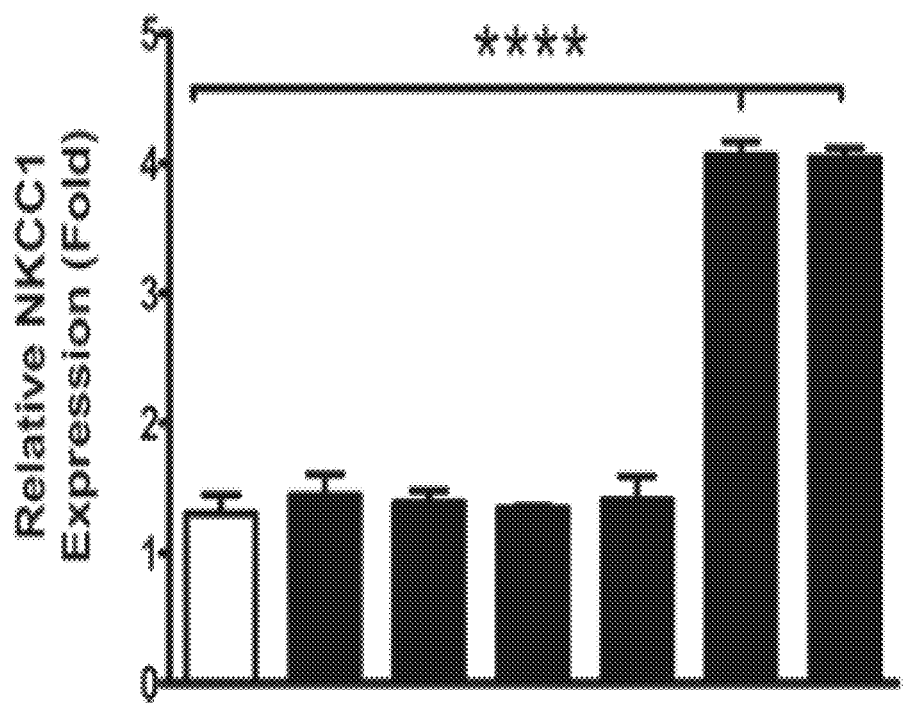
FIG. 16(B) is a graph showing aldosterone (ALD) increases activity levels and protein expression of $Na^+$—$K^+$-$2Cl^-$ cotransport protein (NKCC1). HT-29 cells were treated with ALD for the times and doses indicated, as shown in FIG. 16(A). Densiometric results from the blot showing bar graph results as a means±SD from 3 independent experiments, the ordinate represents relative expression, defined as expression level relative to the time 0 or dosage point. Open bar: control, nontreated sample; the vehicle was 100% alcohol, in which the ALD and eplerenone were dissolved. Statistical significance: * p<0.05,  p<0.01, * p<0.001, **** p<0.0001.
Figure 17A:
FIG. 17(A) is a blot showing aldosterone (ALD) increases activity levels and protein expression of $Na^+$—$K^+$-$2Cl^-$ cotransport protein (NKCC1). HT-29 cells were treated with ALD for the times and doses indicated and lysed by RIPA buffer with cocktail protein inhibitors; proteins were resolved by SDS-PAGE. Western blot was probed sequentially with antibodies to NKCC1 and β-actin as the control. Increases in NKCC1 protein levels are mediated via the activation of mineralocorticoid receptors (MR). HT-29 cells were treated with or without a specific inhibitor of MR, eplerenone (20 µM), and then applied with 1 µM ALD for the indicated times. NKCC1 protein expression was detected in cell lysates by a Western blot, using antibodies to NKCC1, and β-actin as a loading control.
Figure 17B:
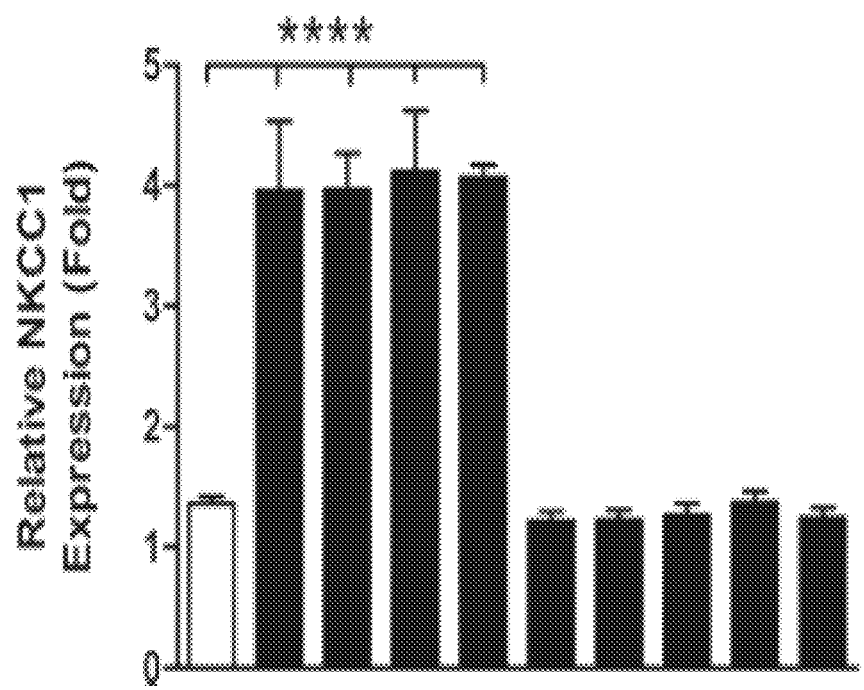
FIG. 17(B) is a graph showing aldosterone (ALD) increases activity levels and protein expression of $Na^+$—$K^+$-$2Cl^-$ cotransport protein (NKCC1). HT-29 cells were treated with ALD for the times and doses indicated as shown in FIG. 17(A). Densiometric results from the blot showing bar graph results as a means±SD from 3 independent experiments, the ordinate represents relative expression, defined as expression level relative to the time 0 or dosage point. Open bar: control, nontreated sample; the vehicle was 100% alcohol, in which the ALD and eplerenone were dissolved. Statistical significance: *p<0.05,  p<0.01, *p<0.001, ****p<0.0001.

ALD induced a sustained induction of NKCC1. ALD treatment upregulated NKCC1 protein activity and expression levels, which remained relatively stable for over 12-24 h of treatment, as seen in FIGS. 13 and 14(A) and (B). This up-regulation took effect within the first 2 h of ALD treatment (1 μM), as seen in FIGS. 15(A) and (B). The threshold of NKCC1 induction was quite sensitive, as there was a significant response at ~10 pM, seen in FIGS. 16(A) and (B). Further, simultaneous treatment with ALD (1 μM) and eplerenone (20 μM), a mineralocorticoid receptor antagonist, prevented the ALD upregulation of NKCC1 protein expression, as seen in FIGS. 17(A) and (B).

Figure 18A:
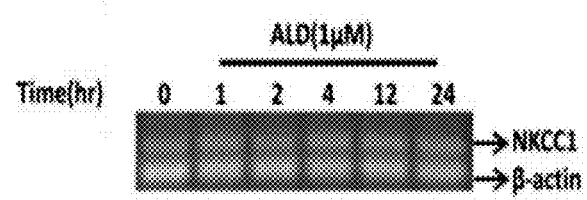
FIG. 18(A) is a blot showing NKCC1 mRNA is not induced by ALD treatment (1 µM). Total RNA was isolated from HT-29 cells treated with ALD (1 µM) at the indicated times and reverse transcribed. Semiquantitative RT-PCR analysis with primers representing the NKCC1 NH2 terminus was performed using 10 ng of the diluted RNA, analyzed on a 2% TAE agarose gel, and stained with GelRed Nucleic Acid Stain. Amplified products were resolved by agarose gel electrophoresis. β-actin was included as a loading control.
Figure 18B:
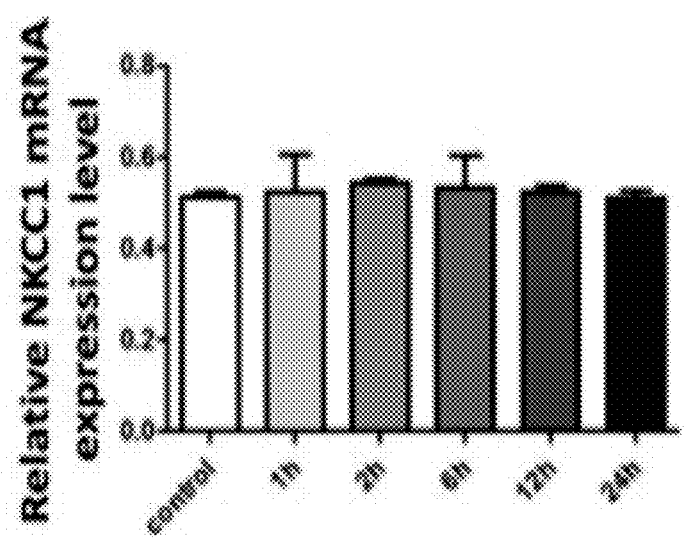
FIG. 18(B) is a graph showing NKCC1 mRNA is not induced by ALD treatment (1 µM). Total RNA was isolated from HT-29 cells treated with ALD (1 µM) at the indicated times and reverse transcribed. Densiometric results from the agarose gel electrophoresis seen in FIG. 18(a) are shown as bar graph results are means±SD from 3 independent experiments, the ordinate represents relative expression, defined as expression level relative to the control (β-actin expression). There were no statistically significant differences.
Figure 19:
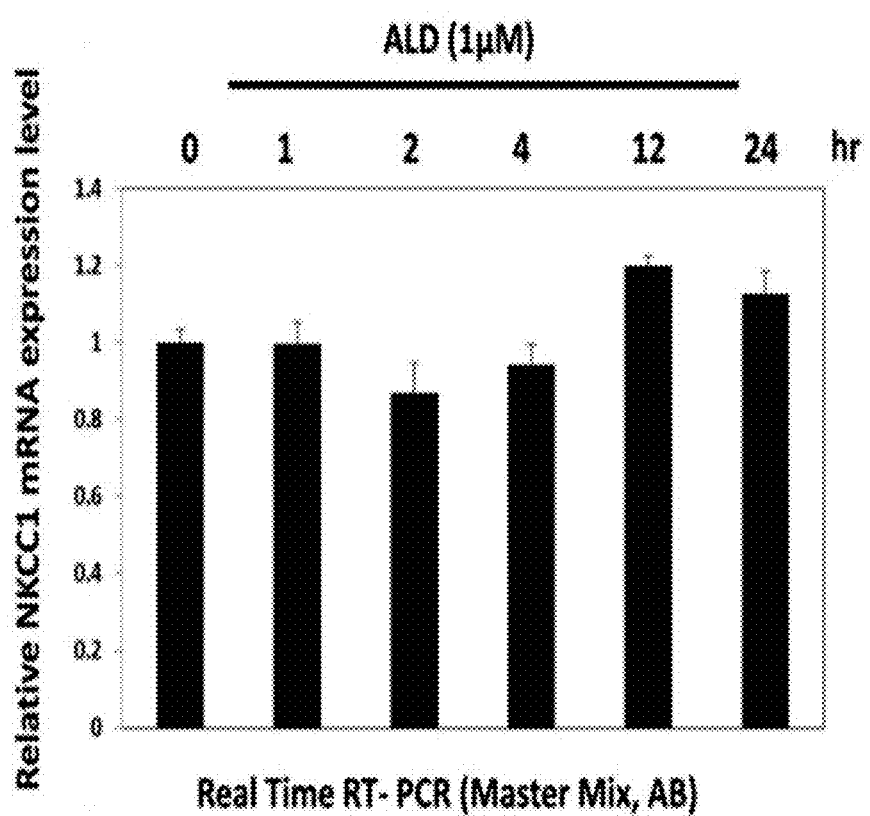
FIG. 19 is a graph showing NKCC1 mRNA is not induced by ALD treatment (1 µM). Total RNA was isolated from HT-29 cells treated with ALD (1 µM) at the indicated times and reverse transcribed using a semiquantitative RT-PCR analysis with primers representing the NKCC1 NH2 terminus was performed using 10 ng of the diluted RNA, analyzed on a 2% TAE agarose gel, and stained with GelRed Nucleic Acid Stain. Amplified products were resolved by agarose gel electrophoresis. β-actin was included as a loading control. 10 ng of RNA and primers were used for real-time quantitative (q)RT-PCR. Bar graph results are means±SD from 3 independent experiments. There were no statistically significant differences.

The increase of NKCC1 protein expression by ALD is not associated with mRNA induction but is mediated by mineralocorticoid receptors. We investigated whether the increased protein expression of NKCC1 was tied to elevated mRNA levels by using RT-PCR. Both methods utilized here resulted in similar findings: there was no mRNA change with ALD stimulation, seen in FIGS. 18(A), (B) and 19. These results indicate that the ALD-induced increase of NKCC1 protein expression is associated with the activation of mineralocorticoid receptors by ALD.

Figure 20A:
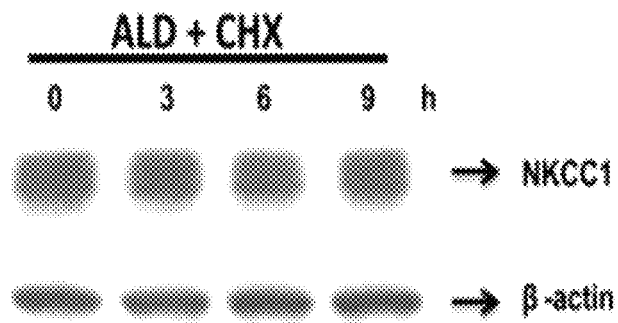
FIG. 20(A) is a blot showing the role of ALD in NKCC1 protein induction and stability. Cell lysates were analyzed by gel electrophoresis and Western blot analysis. Blots were probed with antibodies against NKCC1, and β-actin served as the control. HT-29 cells were stimulated with ALD (1 μM) and then either treated or not treated with the protein synthesis inhibitor cycloheximide (CHX; 20 μg/ml) for 3, 6, or 9 h. Western blots of (A) ALD and CHX showing NKCC1 protein expression in HT-29 cells treated with the above protocol.
Figure 20B:
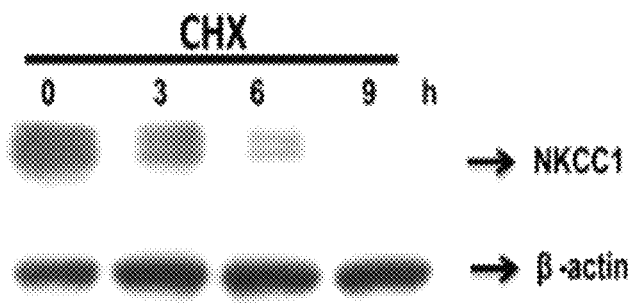
FIG. 20(B) is a blot showing the role of ALD in NKCC1 protein induction and stability. Cell lysates were analyzed by gel electrophoresis and Western blot analysis. Blots were probed with antibodies against NKCC1, and β-actin served as the control. HT-29 cells were stimulated with ALD (1 μM) and then either treated or not treated with the protein synthesis inhibitor cycloheximide (CHX; 20 μg/ml) for 3, 6, or 9 h. Western blots of CHX showing NKCC1 protein expression in HT-29 cells treated with the above protocol.
Figure 20C:
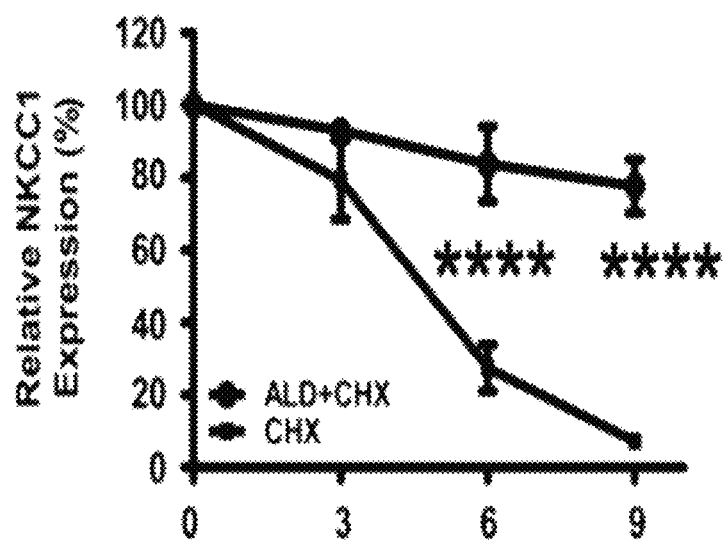
FIG. 20(C) is a graph showing the role of ALD in NKCC1 protein induction and stability. Cell lysates were treated or not treated with the protein synthesis inhibitor cycloheximide (CHX; 20 μg/ml) for 3, 6, or 9 h. and analyzed by gel electrophoresis and Western blot analysis. A graph showing the relative expression of NKCC1 as a function of time since the ALD treatment (x-axis) is summarized by a line graph from 3 independent experiments (bottom). Line graph expression levels are normalized to 100%, relative to the vehicle alone. Statistical significance: ****$p < 0.0001$.

ALD enhances the stability of NKCC1 protein. We discovered that ALD increases NKCC1 protein levels, whereas induction of NKCC1 mRNA synthesis is absent. The regulation of intracellular protein levels is highly dependent on two factors: ribosomal protein synthesis, which is associated with mRNA levels; and posttranslational modification, which is independent of transcriptional activation and translational regulation. To explore the possibility that posttranslational modification is the mechanism by which ALD exerts its effects, cells were treated with cycloheximide, a translation inhibitor, for 3, 6, or 9 h. The results show that in the presence of ALD (1 µM) the decline of NKCC1 protein levels was much slower in response to cycloheximide, relative to the nontreated cells, as seen in FIGS. 20(a), (B) and (C).

Figure 21A:
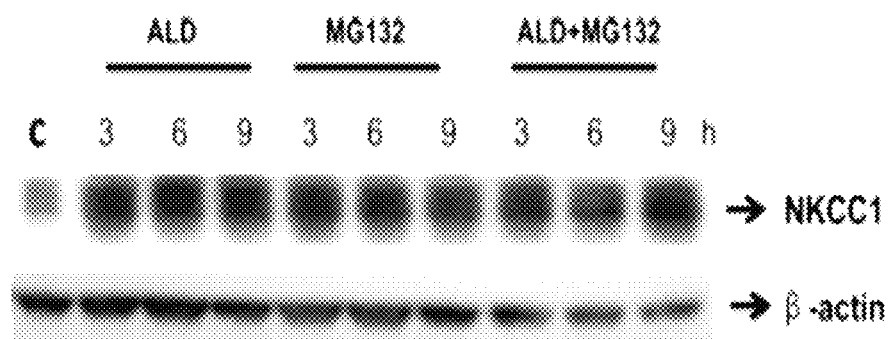
FIG. 21(A) is a blot showing net result of inhibition of NKCC1 ubiquitination is an increase in its protein expression. Cells were treated with 1 μM ALD or proteasome inhibitor MG132 (20 μg/ml), which prevents/reduces the degradation of proteins by ubiquitin-proteasome mechanisms, or the combination of ALD and MG132, for 3, 6, or 9 h. NKCC1 protein expression was detected by Western blot with β-actin as the control.
Figure 21B:
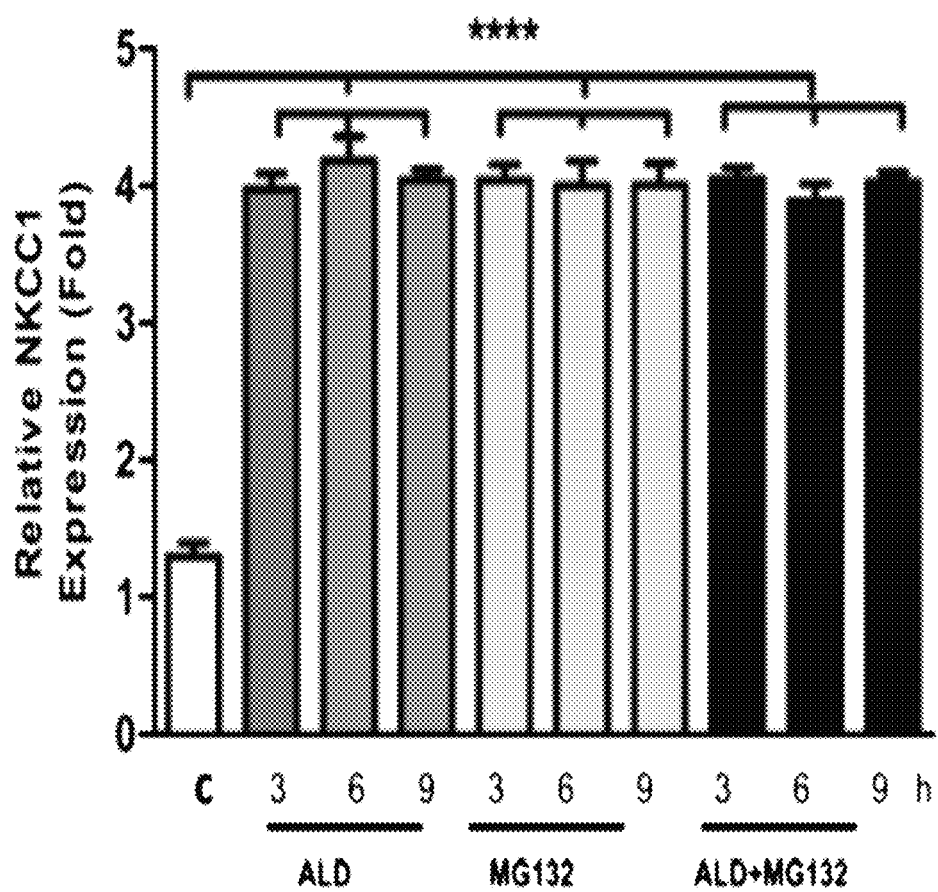
FIG. 21(B) is a graph showing net result of inhibition of NKCC1 ubiquitination is an increase in its protein expression. Cells were treated with 1 μM ALD or proteasome inhibitor MG132 (20 μg/ml), and NKCC1 protein expression was detected by Western blot as shown in FIG. 21(A). Densiometric analysis is shown in the graphs, with open bars are the control, medium-shaded are ALD alone, light shading indicates MG132, and the dark shading designates the ALD+MG132 combined condition. For each of these 4 conditions, the left bar represents 3 h, the middle bar represents 6 h, and the right bar designates 9 h. The relative expression of NKCC1 is plotted in the graphs for 3 independent experiments, with the same format as FIG. 1. Statistical significance: **$p < 0.0001$, *$p < 0.001$, indicating a significant difference between the control condition and the other conditions.
Figure 22A:
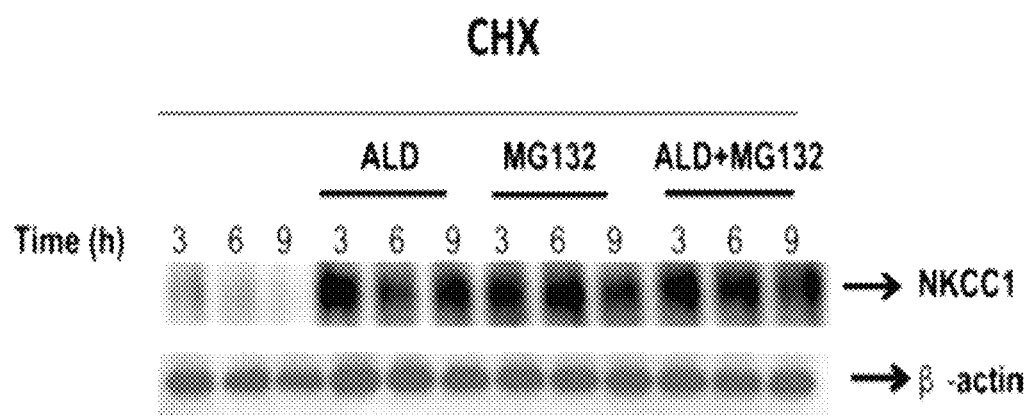
FIG. 22(A) a blot showing net result of inhibition of NKCC1 ubiquitination is an increase in its protein expression. Cells were first treated with CHX (protein synthesis inhibitor, 20 μg/ml) and then ALD (1 μM) or MG132 (50 μg/ml) or the combination of ALD/MG132 for 3, 6 or 9 h.
Figure 22B:
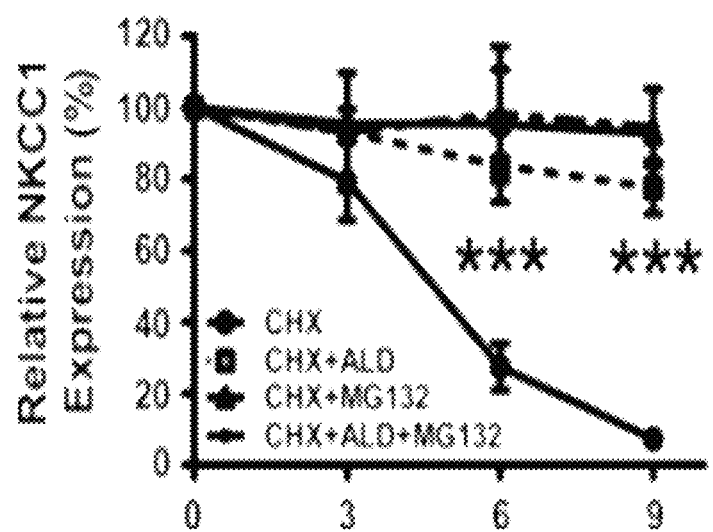
FIG. 22(B) is a graph showing net result of inhibition of NKCC1 ubiquitination is an increase in its protein expression. Cells were first treated with CHX, then ALD (1 μM) or MG132 (50 μg/ml) or the combination of ALD/MG132 for 3, 6 or 9 h as shown in FIG. 22(A). Densiometric analysis is shown in the graphs, with open bars are the control, medium-shaded are ALD alone, light shading indicates MG132, and the dark shading designates the ALD+MG132 combined condition. For each of these 4 conditions, the left bar represents 3 h, the middle bar represents 6 h, and the right bar designates 9 h. The relative expression of NKCC1 is plotted in the graphs for 3 independent experiments, with the same format as FIG. 1. Statistical significance: **$p < 0.0001$, *$p < 0.001$, indicating a significant difference between the control condition and the other conditions.

Cells were then treated with MG132 (20 µg/ml) to inhibit the ubiquitination of NKCC1 protein. Specifically, in the presence of MG132, proteins that are polyubiquitinated will accumulate intracellularly, often as aggregates. This accumulated pool is typically nonfunctional. The effect of ALD on NKCC1 expression was mimicked by MG132, suggesting that ALD reduces proteasomal degradation of NKCC1. Interestingly, when combining ALD with MG132 treatments, the increased level of NKCC1 protein expression was the same as the ALD or MG132 treatments alone, seen in FIGS. 21(A) and (B). Next, global protein translation was inhibited with cycloheximide, while simultaneously treating with MG132 and ALD. In the presence of cycloheximide, the joint effect of ALD and MG132 did not increase the NKCC1 stability relative to either ALD or MG132 treatments alone, as seen in FIGS. 22(A) and (B). Apparently, ALD promotes NKCC1 protein stability and subsequently enhances its accumulation in cells by preventing posttranslational modifications involving ubiquitination of NKCC1.

Figure 23A:
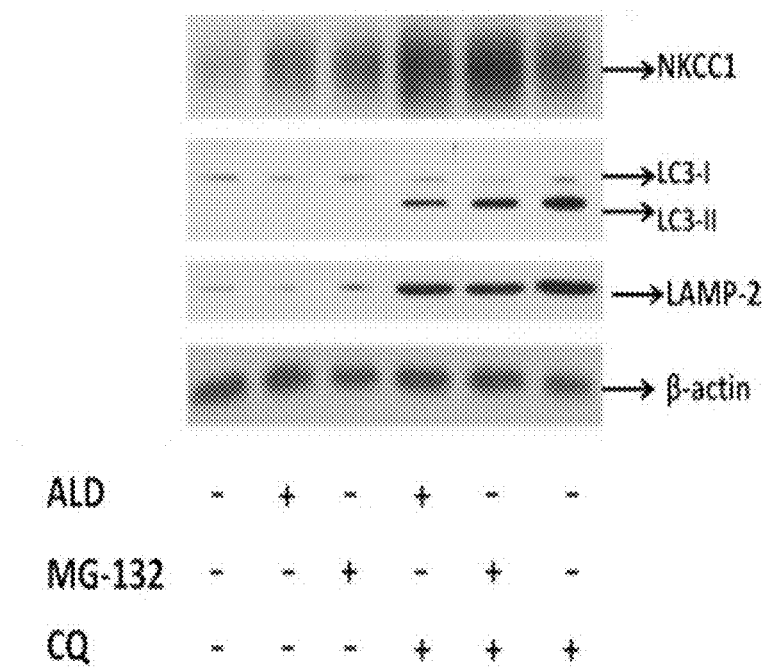
FIG. 23(A) is a blot and showing ubiquitination, but not the lysosome pathway, is involved in the regulation of NKCC1 by ALD. To exclude the possibility that depletion of free ubiquitin by the prolonged MG-132 treatment triggered nonspecific inhibition of lysosome degradation of NKCC1 and investigate whether ALD is involved in a lysosome pathway, a parallel experiment with chloroquine (CQ) was performed. Here, the positive marks (+) indicate application of ALD (1 μM), MG132 (20 μM), CQ (50 μM), ALD+CQ, and MG132+CQ for 9 h. An autophagosome marker, autophagy-related gene 8 named as light chain 3 (LC3), and the lysosome-associated membrane protein 2 (LAMP-2) were used was indicators of lysosome pathway activation (phagocytic activity) under treatment with CQ.
Figure 23B:
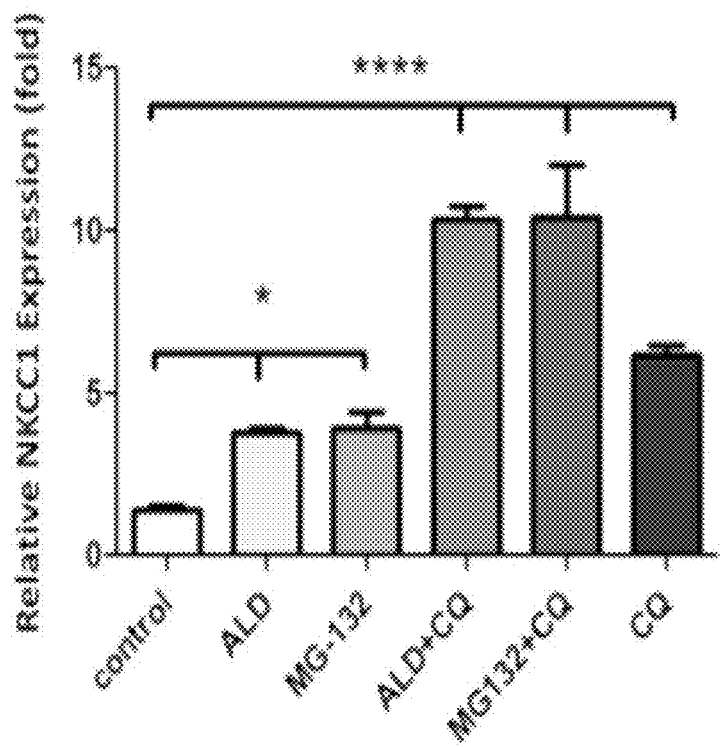
FIG. 23(B) is a graph showing ubiquitination, but not the lysosome pathway, is involved in the regulation of NKCC1 by ALD. Densiometric analysis of the blot in FIG. 23(a) shows activation of lysosome pathway proteins is indicated as the increased expression of lysosome markers, LC3-I, -II, and LAMP-2 vs. controls (1st bar). ALD and MG-132 treatments achieved some induction of NKCC1 protein expression [1st bar (Control) vs. 2nd and 3rd bars] without increasing lysosome pathway markers (rows 2 and 3). The induction of NKCC1 protein expression reached higher levels when ALD (1 μ_M) was combined with CQ (50 μM) treatment (4th bar). The effects of combined treatment with MG-132 (20 μM) and CQ, (5th bar) on the induction of NKCC1 equal the effects of ALD and CQ together (4th bar) but exceed those of ALD, CQ, or MG132 alone (2nd, 3rd, and 6 bars). Note that only when the lysosome pathway blocker CQ was used was there significant upregulation of LC3II and LAMP-2 expression levels. These data suggest that ALD specifically suppresses the proteasomal degradation of NKCC1 without affecting its degradation via the lysosomal pathway. Bottom: mean data±SD bars; ****$p < 0.0001$, indicates the significance of control vs. 4th, 5th, and 6$t^h$ bars; *$p < 0.05$, indicates the significance of control vs. the ALD and MG132 conditions alone.

Ubiquitination, but not the lysosome pathway, is involved in NKCC1 induction by ALD. A parallel experiment was performed with chloroquine (CQ), a lysosome inhibitor, to exclude the possibility that prolonged MG-132 treatment depleted free ubiquitin by nonspecific inhibition of lysosome degradation of NKCC1 and to confirm whether or not ALD is involved in a lysosome pathway. In FIGS. 23(A) and (B), the positive marks indicate application of ALD, MG-132, or CQ. Activation of lysosome pathway proteins is given in FIG. 23(A) (LC3-I and -II and LAMP-2). As shown in FIG. 23(B), ALD and MG-132 treatments induce NKCC1 protein expression similarly [1st bar (control) vs. 2nd and 3rd bars], whereas NKCC1 protein expression increased when ALD (1 µM) was combined with CQ (50 µM) treatment (4th bar). The combined treatment with MG-132 (20 µM) and CQ (5th bar) on the induction of NKCC1 equals the effects of ALD and CQ together (4th bar) but exceeds those of ALD, CQ, or MG132 alone (2nd, 3rd, and 6th bars). Note that only when the lysosome pathway blocker CQ was used was their significant upregulation of LC3II and LAMP-2 expression levels. Taken together, these data suggest that ALD specifically suppresses the proteasomal degradation of NKCC1 without affecting its degradation via the lysosomal pathway.

Figure 24A:
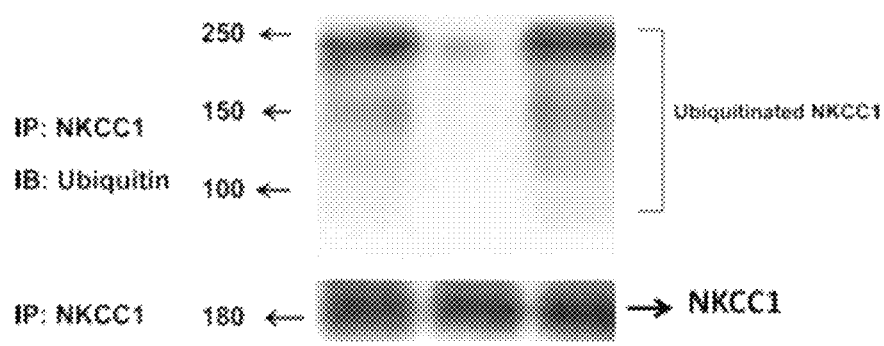
FIG. 24(A) is a blot showing ALD blocks the ubiquitination of NKCC1. HT-29 cells were treated with 20 μM MG132 for 2 h with or without ALD (1 μM) or GSK650394 to the media for 24 h. Cells were collected in RIPA buffer and used for 2 assays: Western blot for the detection of NKCC1 protein expression, and immunoprecipitation with anti-NKCC1 antibody followed by immunoblotting with antiubiquitin antibody. MG132 alone. Middle: MG132 plus ALD shows low levels of ubiquitinated NKCC1. MG132 plus ALD and GSK650394 shows increased levels of NKCC1 ubiquitination. IB, immunoblotting; IP, immunoprecipitation. Numbers indicate molecular mass in kDa.
Figure 24B:
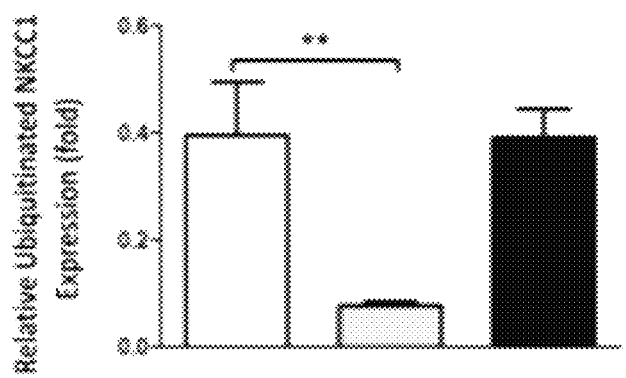
FIG. 24(B) is a graph showing ALD blocks the ubiquitination of NKCC1. HT-29 cells were treated with 20 μM MG132 for 2 h with or without ALD (1 μM) or GSK650394 to the media for 24 h. Cells were collected in RIPA buffer and used for 2 assays as per FIG. 24(A). Densiometric analysis as shown by a bar graph summary from 3 independent experiments like that at top. Statistical significance: **$p < 0.01$.

ALD decreases the endogenous ubiquitination of NKCC1 and inhibition of SGK1 activation blocks this downregulation. To confirm the role of ubiquitination of NKCC1 in the ALD mechanism, we blocked the endogenous ubiquitination of HT-29 cells by applying MG132 (20 µM). Two hours after the MG132 application, cells were treated with ALD (1 µM) or the SGK1 inhibitor GSK 650394 (50 µM) or ALD (1 µM) combined with SGK1 inhibitor GSK 650394 (50 µM) for 24 h. It was previously shown that SGK1 regulates $Na^+/Cl^-$ cotransporter (NCC) and NKCC1 has structural similarities to NCC (Arroyo, et al., Nedd4-2 modulates renal Na_-Cl__ cotransporter via the aldosterone-SGK1-Nedd4-2 pathway. *J Am Soc Nephrol* 22: 1707-1719, 2011). As predicted from the results of FIGS. 22(A) and (B), the NKCC1 expression in the three groups (with or without ALD treatment, or ALD+GSK 650394) was equal, as seen in FIGS. 24(A) and (B). Correspondingly, endogenous ubiquitinated NKCC1 was significantly reduced in the ALD-treated cells (middle bar), because fewer mono- and polyubiquitin bands were seen in the ALD treatment group relative to the cells in the non-ALD group, as seen in FIGS. 24(A) and (B) (compare left bar to middle bar). Next, blocking SGK1 reduces the ability of ALD to suppress NKCC1 ubiquitination, as seen in FIGS. 24(A) and (B) (compare middle bar to right bar). These results, utilizing a complete endogenous system (auto-ubiquitination assay), confirm that ALD is responsible for the inhibition of the NKCC1 ubiquitination, likely mediated by SGK1-Nedd4-2 activation.

Figure 25:
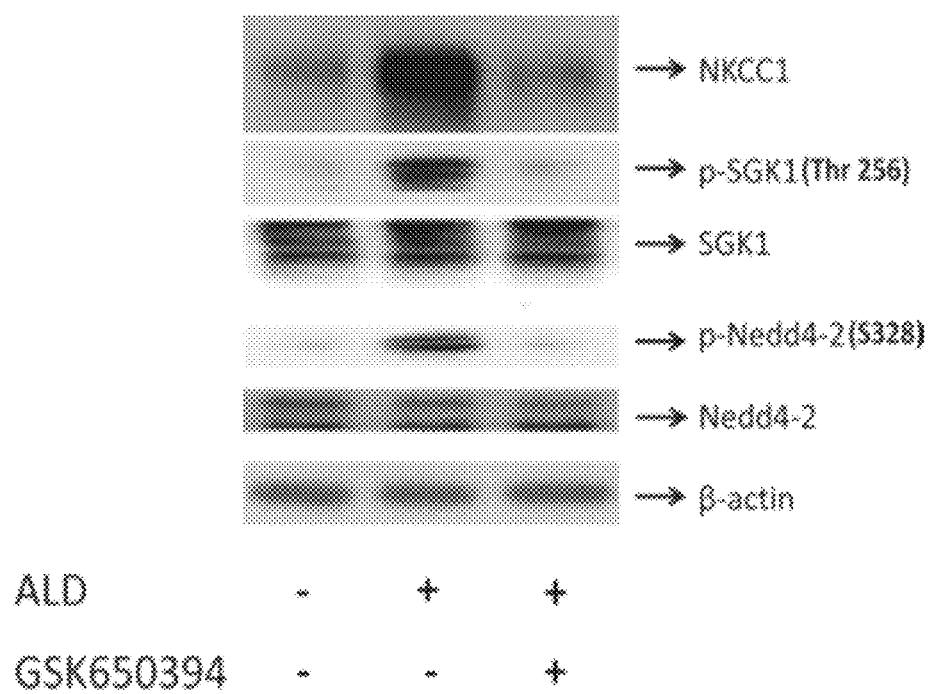
FIG. 25 is a blot showing ALD modulation of NKCC1 via the ALD-SGK1-Nedd4-2 pathway. HT-29 cells were treated with ALD (1 μM) or ALD (1 μM)+GSK650394 (50 μM) for 9 h. Cell lysates were analyzed by Western blot as indicated. Blots are representative of 3 independent experiments. Left: controls. Middle: ALD increases the phosphorylations of SGK1 and Nedd4-2, concomitantly there is an increased induction of NKCC1 protein expression (1st row). Right: SGK1 inhibitor GSK 650394 (50 µM) blocked phosphorylation of SGK1 and Nedd4-2 (2nd and 4th rows), but the total protein expressions of SGK1 and Nedd4-2 showed no differences, and ALD did not increase the protein expression of NKCC1.

ALD inhibits the degradation of NKCC1 through the SGK1-Nedd4-2 pathway. Interaction between ENaC (a $N^+$ channel) and Nedd4-2 is required for ENaC internalization and protein stability (Arroyo, et al., Nedd4-2 modulates renal Na_-Cl__ cotransporter via the aldosterone-SGK1-Nedd4-2 pathway. *J Am Soc Nephrol* 22: 1707-1719, 2011). Specifically, Nedd4-2 binds ENaC via a specific domain called the PY motif. Mutation of this domain induces a kidney disease called Liddle's syndrome. Since NKCC1 and NCCs belong to the cation $Cl^-$ cotransporters (CCCs), and the CCCs exhibit a common structure in their functional regulation domains, such as the membrane associated domain and the phosphoacceptor sites (Richardson & Alessi, The regulation of salt transport and blood pressure by the WNK-SPAK/OSR1 signalling pathway. *J Cell Sci* 121: 3293-3304, 2008, Simard, et al., Characterization of a novel interaction between the secretory $Na^+$—$K^+$-$2Cl^-$ cotransporter and the chaperone hsp90. *J Biol Chem* 279: 48449-48456, 2004), we hypothesize that there is a similarity in the regulation of NCC and NKCC1 inductions by ALD. To test this, we found that ALD increases the phosphorylation of SGK1 and Nedd4-2 and concomitantly there is an increased induction of NKCC1 protein expression, as seen in FIG. 25 (middle bar). It was also observed that the SGK1 inhibitor GSK 650394 (50 µM) blocked phosphorylation of SGK1 and Nedd4-2, as seen in FIG. 25, but the total protein expressions of SGK1 and Nedd4-2 showed no differences (compare middle bar to right bar). Lastly, ALD in the presence of GSK 650394 did not increase protein expression of NKCC1, as seen in FIG. 25 (compare middle bar to right bar). These data suggest that the most likely target of ALD in regulation of NKCC1 is the ALD-SGK1-Nedd4-2 pathway.

Figure 26:
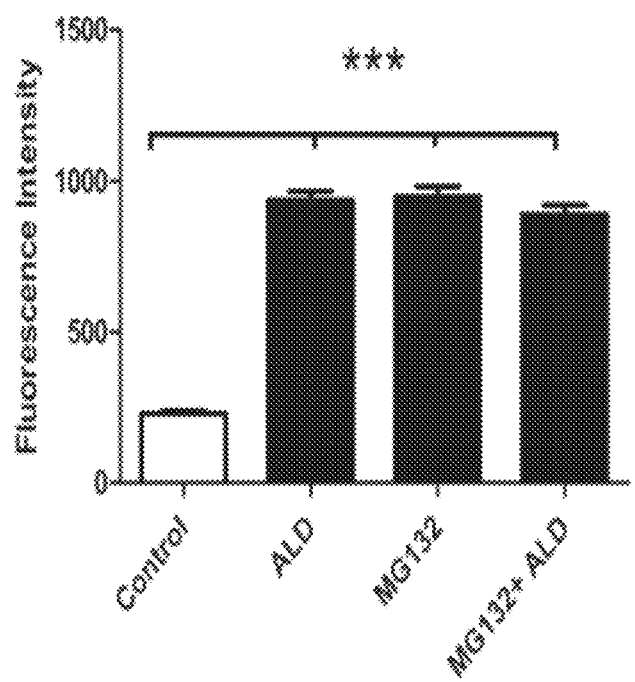
FIG. 26 is a graph showing ALD increases the $K^+$ efflux of NKCC1. The functionality of NKCC1 activity was analyzed in individual cells using bumetanide, an NKCC1 antagonist, combined with thallium ($Tl^+$) uptake, a physiological measure of NKCC1 activity. Cells were loaded with thallium-sensitive dye FluxOR. Fluorescence photos (fluorescence excitation and emission: 488/525 nm) were taken 90 s after addition of 2.8 mM $TlSO_4$ to the media. The graph represents the fluorescence signal average after application of bumetanide, for 1) control: with bumetanide; 2) ALD: aldosterone alone, with bumetanide; 3) MG132 alone (with bumetanide); and 4) MG132 combination with ALD (with bumetanide). Bar graph (bottom) represents the bumetanide-sensitive component of the $Tl^+$ uptake, as measured with densitometry, in 24 labeled cells for each condition. The intensity reported on the ordinate in the bar graph is normalized by subtracting the bumetanide fluorescence levels (bottom row) from the nonbumetanide conditions (top row). ***$p < 0.001$.

Influence of ALD on NKCC1 transporter activity. It is possible that increasing NKCC1 protein expression may not have a significant physiological functional role unless there is a parallel increase in potassium transport activity. We hypothesize that the overall activity levels of NKCC1 are associated with its expression levels in cells. To test this hypothesis, a more efficient and sensitive method, fluorescence Ion flux assays was adopted to measure NKCC1 transporter activity. The signal intensity was analyzed using $Tl^+$ as a surrogate of $K^+$ and a $Tl^+$-sensitive fluorescent dye (FlixOR™) to visualize Tl⁺ uptake through NKCC1 in single cells. The signal intensity corresponding to the relative K⁺ efflux was measured in a total of 24 cells. We found that when ALD was added to the culture medium, a marked increase in fluorescence was observed, reflecting upregulated Tr uptake, as seen in FIG. 26. Adding MG132 and the combination of ALD with MG132 had identical enhancements similar to the ALD treatment alone, as seen in FIG. 26 (3rd and 4th bars), since the fluorescence intensities were identical among them.

NKCC1 proteins play important roles in key physiological systems, including neural, cardiac, renal, and sensory systems. Correction of mis-regulation of the expression and functionality of NKCC1 that accompanies disease states and aging would have biotherapeutic and pharmaceutical implications. The present study demonstrates for the first time that this naturally occurring steroid hormone can precisely and sensitively regulate NKCC1 protein expression and accompanying functionality.

Additionally, the present investigation revealed that ALD exerts its regulatory effects on NKCC1 protein expression via mineralocorticoid receptors without altering mRNA levels. Prevailing evidence suggests that the mechanisms underlying rapid ALD effects, such as actions observed in the present study, can involve activation of protein kinases and secondary messenger signaling cascades and also modulation of the transcriptional action of ALD through mineralocorticoid receptors (Guo, et al., Axin and GSK3-b control Smad3 protein stability and modulate TGF-γ signaling. *Genes Dev* 22: 106-120, 2008). Additionally, rapid nongenomic effects of ALD have been recognized for some time, but whether or not mineralocorticoid receptors are involved remains controversial (Eisen et al., Novel membrane receptors for aldosterone in human lymphocytes: a 50 kDa protein on SDS-PAGE. *Cell Mol Biol* 40: 351-358, 1994, Marver, Influence of adrenalectomy and steroid replacement on heart citrate synthase levels. *Am J Physiol Endocrinol Metab* 246: E452-E457, 1984, Thomas, et al., Mechanisms underlying rapid aldosterone effects in the kidney. *Annu Rev Physiol* 73: 335-357, 2011). For example, spironolactone can have nongenomic actions in cases of diabetic retinopathy. Also, in the RCCD2 rat cell line, early increases in transepithelial sodium transport elicited by ALD are not associated with transcriptional events but operate through the PKCα signaling pathway. This is accompanied by serine and threonine phosphorylation of the endogenous mineralocorticoid receptors. Interestingly, activation of this PKCα signaling cascade appears as a key event in the development of the later genomic response; blockade of this initial pathway prevents the late response to ALD (Fuller & Young, Mechanisms of mineralocorticoid action. *Hypertension* 46: 1227-1235, 2005). Additionally, nongenomic effects of ALD can be inhibited by specific mineralocorticoid receptor antagonists, such as eplerenone and water soluble RU28318 (Le Moëllic, et al., Early nongenomic events in aldosterone action in renal collecting duct cells: PKC-alpha activation, mineralocorticoid receptor phosphorylation, and cross-talk with the genomic response. *J Am Soc Nephrol* 15: 1145-1160, 2004, Michea, et al., Eplerenone blocks nongenomic effects of aldosterone on the Na⁺/H⁺ exchanger, intracellular $Ca^{2+}$ levels, and vasoconstriction in mesenteric resistance vessels. *Endocrinology* 146: 973-980, 2005). Grossmann and colleagues (Grossman, et al., Human mineralocorticoid receptor expression renders cells responsive for nongenotropic aldosterone actions. *Mol Endocrinol* 19: 1697-1710, 2005, Mihallidou, Nongenomic actions of aldosterone: physiological or pathophysiological role? *Steroids* 71: 277-280, 2006) proposed three possible ALD signaling pathways: genomic (mineralocorticoid receptor dependent), nongenomic (mineralocorticoid receptor dependent), and nongenomic (mineralocorticoid receptor independent). Our study suggests that the NKCC1 protein induction resides on the rapid nongenomic, mineralocorticoid receptor-dependent ALD pathway, since the time to start the enhancement of NKCC1 protein expression in response to ALD treatments is relatively short, is blocked by eplerenone, and shows no changes in mRNA levels.

Previous studies implicate posttranslational phosphorylation associated with NKCC1 expression changes (Akar et al., Vasoconstrictors and nitrovasodilators reciprocally regulate the Na_—K_-2Cl_-cotransporter in rat aorta. *Am J Physiol Cell Physiol* 276: C1383-C1390, 1999, Delpire & Austin, Kinase regulation of Na⁺—K⁺-2Cl⁻ cotransport in primary afferent neurons. *J Physiol* 588: 3365-3373, 2010, Grossmann & Gekle, New aspects of rapid aldosterone signaling. *Mol Cell Endocrinol* 308: 53-62, 2009, Haas & Forbush, The Na—K—Cl cotransporter of secretory epithelia. *Annu Rev Physiol* 62: 515-534, 2000, Kenneth & Delpire, Molecular determinants of hyperosmotically activated NKCC1-mediated K_/K_ exchange. *J Physiol* 588: 3385-3396, 2006, Richardson, et al., Regulation of the NKCC2 ion cotransporter by SPAK-OSR1-dependent and -independent pathways. *J Cell Sci* 124:789-800, 2010, Simard, et al., Characterization of a novel interaction between the secretory Na⁺—K⁺-2Cl⁻ cotransporter and the chaperone hsp90. *J Biol Chem* 279: 48449-48456, 2004). In contrast, the present investigation is the first report that ALD exerts its effects on NKCC1 expression via prevention of posttranslational ubiquitination, e.g., reduces proteasome-dependent degradation of the NKCC1 protein.

Further, we explored the physiological action of NKCC1 in ALD induction. Stimulation of NKCC1 increases Na⁺, K⁺, and Cl⁻ fluxes, as previously noted (Flatman, Regulation of Na—K-2Cl cotransport by phosphorylation and protein-protein interactions. *Biochim Biophys Acta* 1566: 140-151, 2002, Forbush, Regulatory activation is accompanied by movement in the C terminus of the Na-K-Cl cotransporter (NKCC1). *J Biol Chem* 287: 2210-2220, 2012, Grossmann & Gekle, New aspects of rapid aldosterone signaling. *Mol Cell Endocrinol* 308: 53-62, 2009, Jiang, et al., Aldosterone regulates the Na—K-2Cl cotransporter in vascular smooth muscle. *Hypertension* 41: 1131-1135, 2003, Sid, et al., Stimulation of human and mouse erythrocyte Na(+)-K(+)-2Cl(−) cotransport by osmotic shrinkage does not involve AMP-activated protein kinase, but is associated with STE20/SPS1-related proline/alanine-rich kinase activation. *J Physiol* 588: 2315-28, 2010, Thastrup, et al., SPAK/OSR1 regulate NKCC1 and WNK activity: analysis of WNK isoform interactions and activation by T-loop transautophosphorylation. *Biochem J* 441: 325-337, 2012). Ion flux assays represent functional assays that measure efflux of ions through cotransporters such as NKCC1. Radioactive $^{86}Rb$ flux assays have been used effectively to study activity of a number of K⁺ channels and cotransporters and was employed in the present investigation. The cotransporter unidirectional efflux of Rb⁺ (as a tracer for K⁺) is an accepted method to measure cotransporter activity, despite it being bidirectional. Also, the net flux under physiological conditions is inward because of the inward gradients resulting from the equilibrium potentials for both Na⁺ and Cl⁻ (Jiang, et al., Aldosterone regulates the Na—K-2Cl cotransporter in vascular smooth muscle. *Hypertension* 41: 1131-1135, 2003). Recently, a fluorescent assay for the measurement of thallium ions through potassium channels was used to measure NKCC1 activity (Kim, et al., Salt sensitivity of blood pressure in NKCC1-deficient mice. *Am J Physiol Renal Physiol* 295: F1230-F1238, 2008). We utilized this methodology following the protocol of the Delpire group (Geng, et al., The Ste20 kinases SPAK and OSR1 regulate NKCC1 function in sensory neurons. *J Biol Chem* 284: 14020-14028, 2009), since they and other groups have shown similar results between $^{86}$Rb and FluxOR. This method uses Tr as a surrogate of K$^+$, and a Tl$^+$-sensitive fluorescent dye (Flix-ORTM) to visualize Tr uptake through NKCC1 in single cells (Hille, Potassium channels in myelinated nerve: selective permeability to small cations. *J Gen Physiol* 61: 669-686, 1973, Hille, Potassium channels in myelinated nerve: selective permeability to small cations. *J Gen Physiol* 61: 669-686, 1973, Niswender, et al., Novel assay of Gi/o-linked G protein-coupled receptor coupling to potassium channels provides new insights into the pharmacology of the group III metabotropic glutamate receptors. *Mol Pharmacol* 73: 1213-1224, 2008, Weaver, et al., A thallium-sensitive, fluorescence-based assay for detecting and characterizing potassium channel modulators in mammalian cells. *J Biomol Screen* 9: 671-677, 2004). We found that addition of ALD to the media resulted in a marked increase in fluorescence of NKCC1 with both the $^{86}$Rb and Tl$^+$ methodologies. MG132 and the combination ALD and MG132 treatments have identical enhancements to ALD treatment alone. Combining the data from the experiments with ALD and MG132 effects on NKCC1 protein expression and the $^{86}$Rb and Tl$^+$ uptake fluorescence studies, suggested that increasing NKCC1 protein expression involves increasing its functional activity levels.

Summary and conclusions. The present investigation demonstrated that NKCC1 protein expression can be sensitively regulated by application of the naturally occurring hormone ALD. Further experiments suggested that this expression regulation occurs via mineralocorticoid receptors and takes place utilizing mechanisms involving protein stabilization, i.e., reduction of NKCC1 ubiquitination. Since mis-regulation of Na and K$^+$, and/or declines in NKCC1 proteins are involved in many disease states and in aging, being able to precisely control NKCC1 expression levels and functionality has note-worthy biotherapeutic implications for improved clinical practice and drug development.

Example 5

Figure 27A:
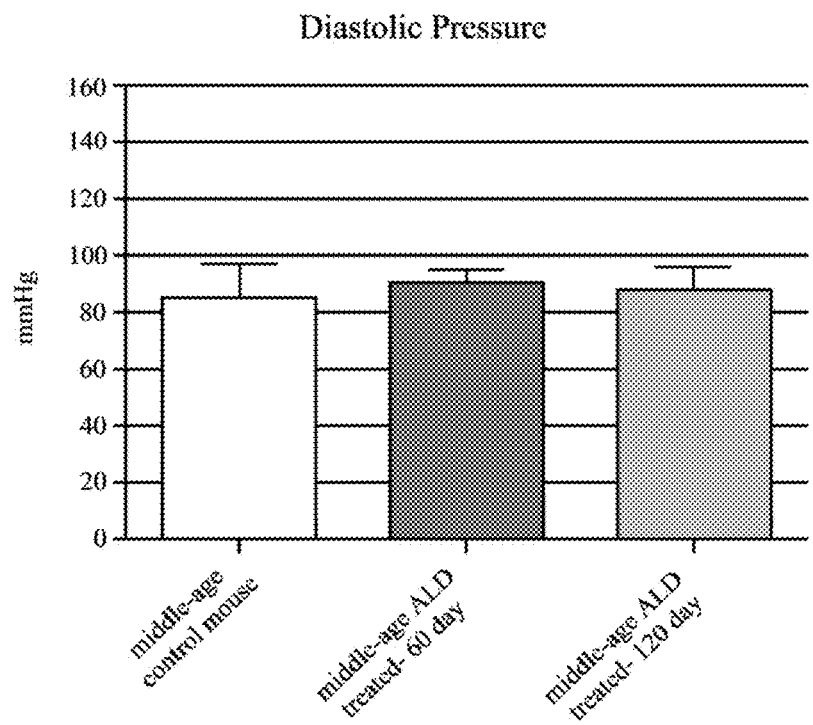
FIG. 27(A) is graph showing the tail-cuff plethysmography of blood pressure for ALD treatments of 60 days and 120 days, compared to middle-age control mice. Diastolic blood pressures were measured for middle-aged (20-21 mon) CBA/CaJ mice and middle-age ALD treated (0.0016 mg/day continuous release through 120 days, one pellet for 60 days and subsequently a second pellet for 60 days) mice, each group, n=5. Pressures were taken at 60 and 120 days and compared to the middle-age control animals. Mean±SD for each group.
Figure 27B:
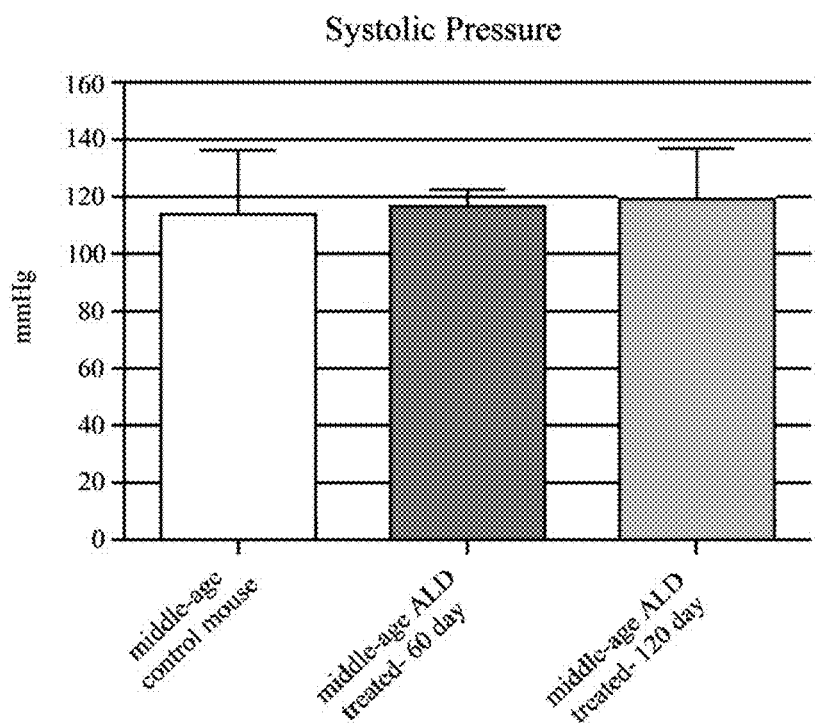
FIG. 27(B) is a graph showing the tail-cuff plethysmography of blood pressure for ALD treatments of 60 days and 120 days, compared to middle-age control mice. Systolic blood pressures were measured for middle-aged (20-21 mon) CBA/CaJ mice and middle-age ALD treated (0.0016 mg/day continuous release through 120 days, one pellet for 60 days and subsequently a second pellet for 60 days) mice, each group, n=5. Pressures were taken at 60 and 120 days and compared to the middle-age control animals. Mean±SD for each group.

CBA/CaJ mice (The Jackson Laboratory, Bar Harbor, Me.) were treated with aldosterone starting at 16-17 months of age. Treatment consisted of a subcutaneous implantation of a 120-day release pellet of D-aldosterone (0.0016 mg/day; Innovative Research of America, Sarasota, Fla.) behind the shoulder in ALD treatment mice (N=5), and same-age control mice (N=5) mice. The mice were kept in their home cages in the USF Vivarium room in the Global Center for Hearing & Speech Research, 12 hour light/dark cycle, 21 degrees C., in a relatively quiet environment with non-invasive auditory testing monthly. During treatment, blood pressures were measured for the mice at 2 and 4 months after start of treatment. As seen in FIGS. 27(A) and (B), neither aging nor the hormone treatment appeared to affect either diastolic or systolic blood pressure.

After the four month (120 day) course of treatment concluded, the mice were euthanized by injecting a commercial euthanasia solution, Euthasol®, (0.22 ml/kg) intraperitoneally. The depth of narcosis/anesthesia was assessed by using the interdigital pinch reflex. Death was confirmed by terminal phlebotomy/exsanguinations and perfusion.

Cell lysates were collected and subject to western blot and RT-PCT analysis. The cells were placed in RIPA buffer and sonicated. Protein concentration was measured using the Bradford method. Proteins were separated by SDS-PAGE. The antibodies used for western blot were: anti-iNOS, nNOS and caspase-3 antibodies (Cell Signaling, Cambridge, Mass.). Total cellular RNA was extracted using the RNeasy Plus Mini Kit (74134). For RT-PCR, 10 ng of total cellular RNA was reverse transcribed and complementary DNA was amplified, using the Enhanced Avian HS RT-PCR-100 Kit (Sigma, HSRT20).

Primers used for qRT-PCR were as follows:

```
For nNOS:
Sense
                                        (SEQ ID No. 5)
TTGGCGTTCGTGATTACTGT;
and Antisense
                                        (SEQ ID No. 6)
ATCAGGCTGGTACTCAA.

For iNOS:
Sense
                                        (SEQ ID No. 7)
CTGGGACAGCACAGAATGTT;
and Antisense
                                        (SEQ ID No. 8)
TAGGCTTGTCTCTGGGTCCT.
```

Figure 28A:
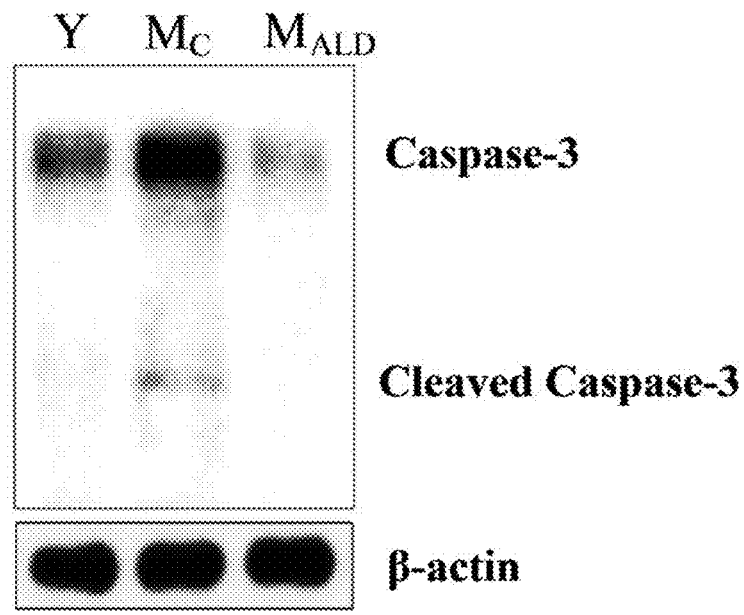
FIG. 28(A) is a blot showing caspase-3 gene expression in modiolar tissue samples from young adult (2-3 month), control middle-aged (20-21 month at end of treatment), and ALD-treated middle-aged (20-21 month) CBA/CaJ mice. Caspase-3 protein expression is elevated in controls, but reduced in ALD-treated older mice. Note: this antibody also recognizes the cleaved caspase-3.
Figure 28B:
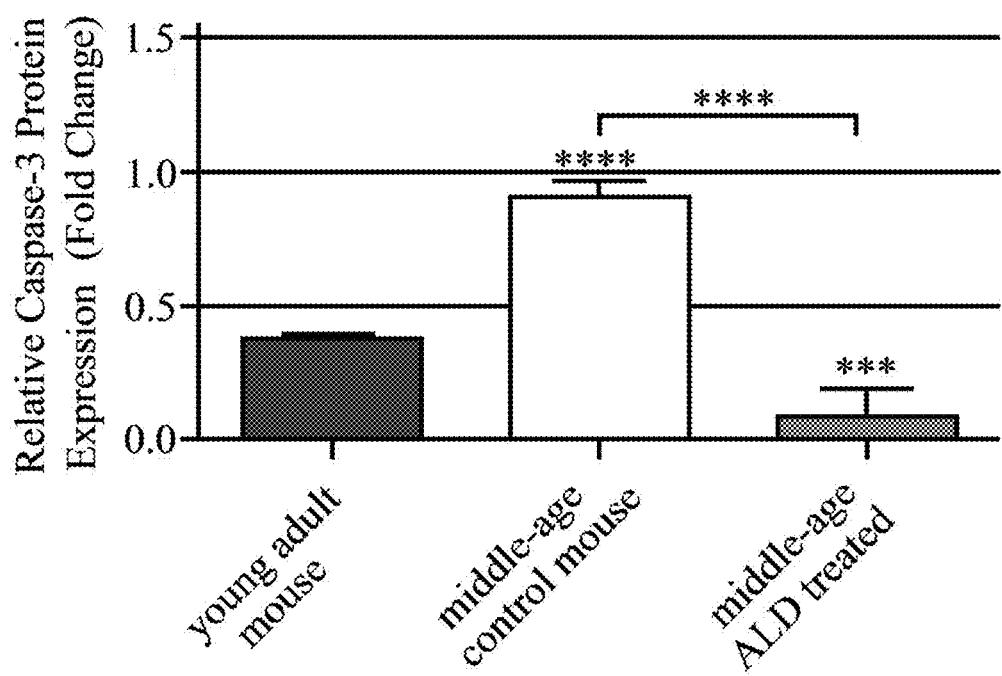
FIG. 28(B) is a blot and graph showing caspase-3 protein expression in modiolar tissue samples from young adult (2-3 month), control middle-aged (20-21 month at end of treatment), and ALD-treated middle-aged (20-21 month) CBA/CaJ mice. Caspase-3 protein expression is elevated in controls, but reduced in ALD-treated older mice. Note: this antibody also recognizes the cleaved caspase-3. Bar graph results are mean±SD from 3 independent experiments. *$p < 0.005$; ** $p < 0.001$.

SGN showed age-correlated levels of caspase-3, an apoptotic pathway marker, as seen in FIGS. 28(A) and (B). However, treatment of mice with ALD showed statistically significant downregulation of the apoptotic pathways, as seen in FIG. 28(A), which reduced caspase-3 to levels below even the young mice samples.

Figure 29A:
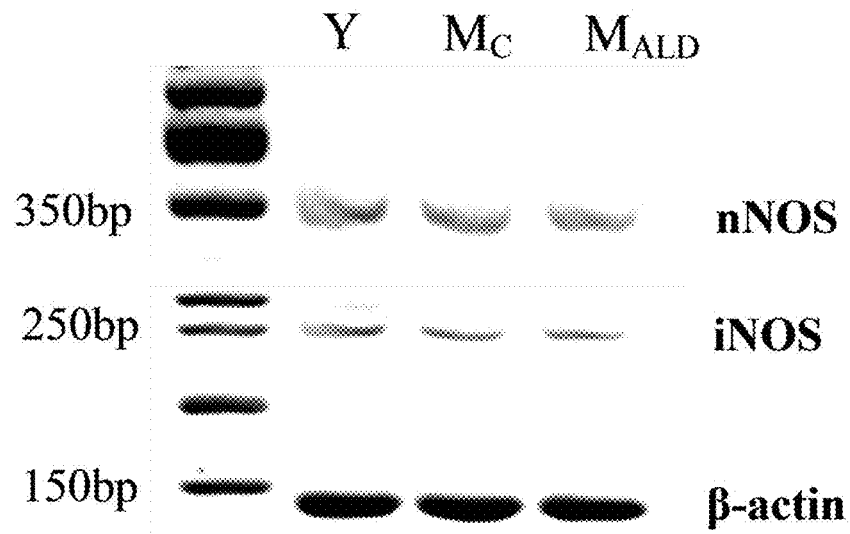
FIG. 29(A) is a blot and graph showing nNOS gene expression in modiolar tissue samples from young adult (2-3 month), control middle-aged (M, 20-21 month at end of treatment), and ALD-treated middle-aged (M, 20-21 month) CBA/CaJ mice. mRNA gene expression of nNOS in modiolar samples show little change across young adult and older mice with and without ALD treatment. nNOS protein expression from modiolus of young adult and older mice with and without ALD treatment.
Figure 29B:
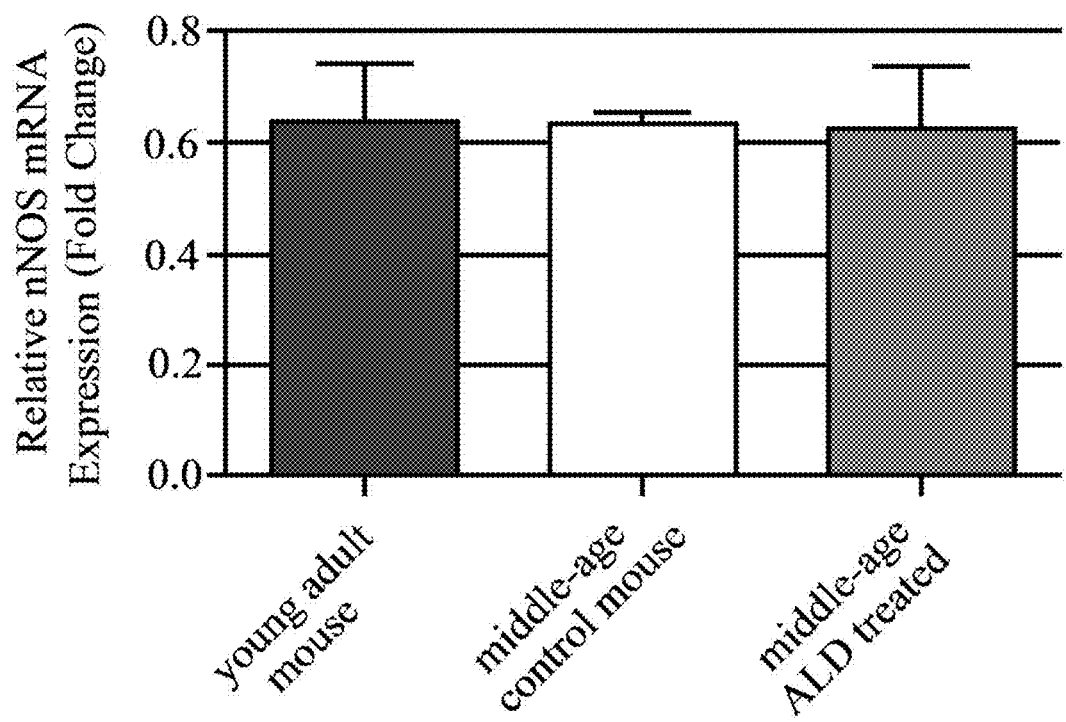
FIG. 29(B) is a graph showing nNOS protein expression in modiolar tissue samples from young adult (2-3 month), control middle-aged (M, 20-21 month at end of treatment), and ALD-treated middle-aged (M, 20-21 month) CBA/CaJ mice. mRNA gene expression of nNOS in modiolar samples show little change across young adult and older mice with and without ALD treatment. nNOS protein expression from modiolus of young adult and older mice with and without ALD treatment. Bar graph results are mean±SD from 3 independent experiments. *$p < 0.005$; ** $p < 0.001$.
Figure 30A:
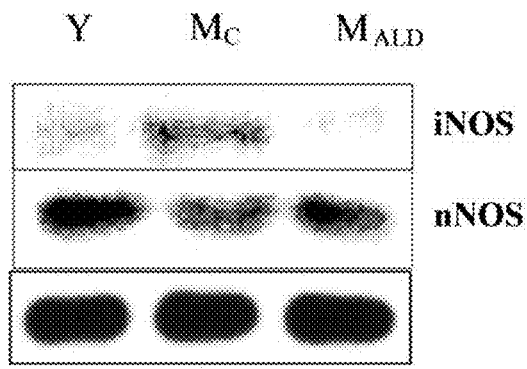
FIG. 30(A) is a blot and graph showing iNOS gene expression in modiolar tissue samples from young adult (2-3 month), control middle-aged (20-21 month at end of treatment), and ALD-treated middle-aged (M, 20-21 month) CBA/CaJ mice. mRNA gene expression of iNOS in modiolar samples show little change across young adult and middle-aged mice with and without ALD treatment. iNOS and nNOS protein expression from modiolus of young adult and older mice with and without ALD treatment.
Figure 30B:
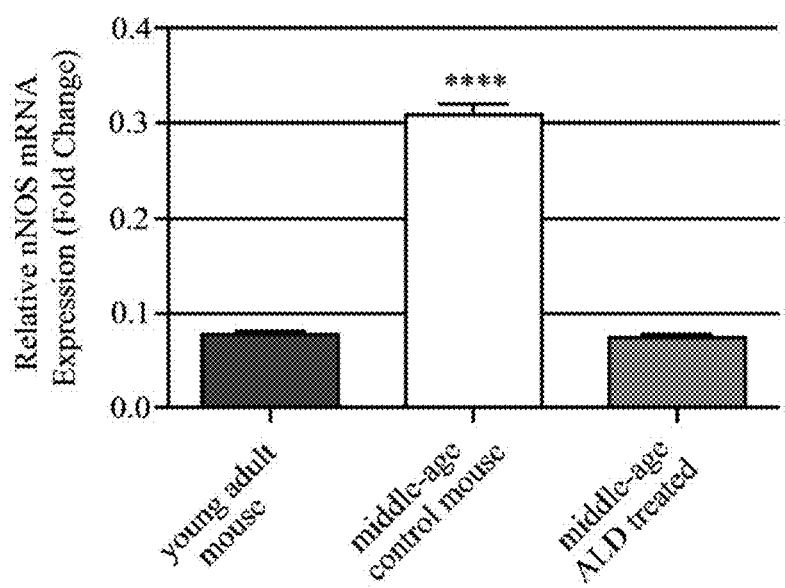
FIG. 30(B) is a graph showing nNOS protein expression in modiolar tissue samples from young adult (2-3 month), control middle-aged (20-21 month at end of treatment), and ALD-treated middle-aged (M, 20-21 month) CBA/CaJ mice. mRNA gene expression of nNOS in modiolar samples show little change across young adult and middle-aged mice with and without ALD treatment. nNOS protein expression from modiolus of young adult and older mice with and without ALD treatment. Bar graph results are mean±SD from 3 independent experiments. *$p < 0.005$; ** $p < 0.001$.
Figure 30C:
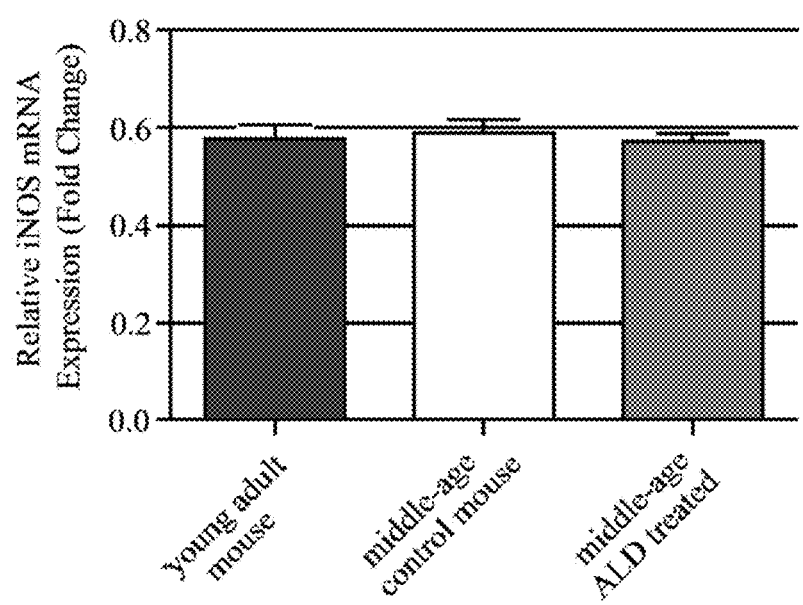
FIG. 30(C) is a blot and graph showing iNOS protein expression in modiolar tissue samples from young adult (2-3 month), control middle-aged (20-21 month at end of treatment), and ALD-treated middle-aged (M, 20-21 month) CBA/CaJ mice. mRNA gene expression of iNOS in modiolar samples show little change across young adult and middle-aged mice with and without ALD treatment. iNOS protein expression from modiolus of young adult and older mice with and without ALD treatment. Bar graph results are mean±SD from 3 independent experiments. *$p < 0.005$; ** $p < 0.001$.

Additionally, changes in inflammation related genes, iNOS and nNOS, gene expression in modiolar tissue samples from young adult (2-3 mon), control middle-aged (20-21 mon), and ALD-treated middle-aged (20-21 mon) CBA/CaJ mice show no alteration in NOS expression between the three treatment groups, as seen in FIGS. 29(A) and (B). However, while iNOS protein levels were approximately the same between the three treatment groups, as seen in FIGS. 30(A) and (B), nNOS protein levels were significantly elevated in middle age control mice, as seen in FIG. 30(C). As nNOS protein levels are altered, whereas mRNA levels are not, it is believed that the data point to likely stabilization of nNOS protein in the SGN.

The alterations in inflammation related genes indicate pharmacologic-based treatments of presbycusis will benefit from anti-inflammatory drug treatment.

Example 6

CBA/CaJ mice (The Jackson Laboratory, Bar Harbor, Me.) were measured for Auditory brainstem responses (ABRs) and then treated with aldosterone starting at 16-17 months of age. Treatment consisted of a subcutaneous implantation of a 120-day release pellet of D-aldosterone (0.0016 mg/day; Innovative Research of America, Sarasota, Fla.) behind the shoulder in ALD treatment mice (N=5), and same-age control mice (N=5) mice. The mice were kept in their home cages in the USF Vivarium room in the Global Center for Hearing & Speech Research, 12 hour light/dark cycle, 21 degrees C., in a relatively quiet environment with non-invasive auditory testing monthly. Auditory brainstem responses (ABRs) were measured again at 2 and 4 months after treatment started Auditory brainstem responses were obtained as follows. The mice were anesthetized with a mixture of ketamine/ xylazine (120 and 10 mg/kg body weight, respectively, intraperitoneal injection) prior to all experimental sessions. All recording sessions were completed in a soundproof acoustic chamber (IAC) with body temperature maintained with a heating pad. ABRs were measured using Biosig (TDT, Alachua, Fla.) data-acquisition system which recorded responses to 5 ms tone pips (0.5-m rise-fall times) with a $\cos^2$ onset envelope, presented at rate of 29/sec. Wave I threshold was defined as the lowest intensity which elicited a clearly replicable response. ABRs were measured pre-treatment and post-treatment at 2 and 4 mon. The pre-treatment ABR threshold was used as the baseline to calculate the thresholds shifts. The wave I peak-to-peak amplitudes were analyzed. Data was compared using Graph-Pad Prism 5.0 (GraphPad Software, Inc. La Jolla, Calif., USA.

Aged mice were compared to hormone-treated aged mice for auditory brainstem response (ABR). ABR thresholds elevated significantly in the control group at 4 month of treatment relative to the ALD group, with hormone-treated mice showed improvement in 12 kHz, seen in FIG. 32, 24 kHz, seen in FIG. 33, 32 kHz, seen in FIG. 34, and 36 kHz, seen in FIG. 35, frequency response at 2 months and 4 months. It is also noted that the data show more profound improvements seen in responses to higher frequencies, as seen in FIGS. 32 through 35.

Figure 31A:
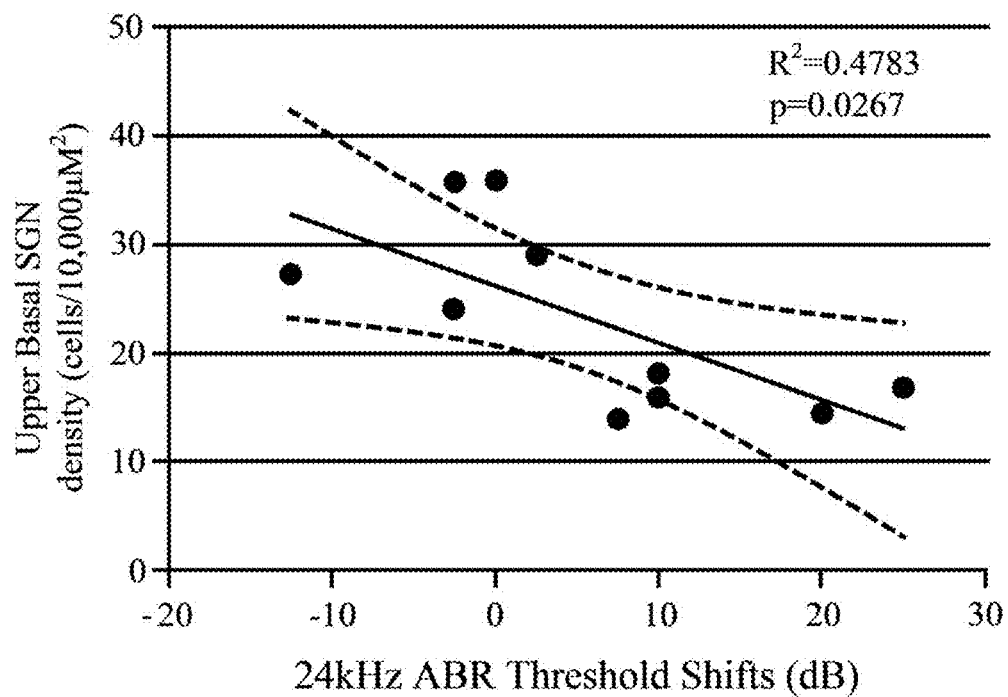
FIG. 31(A) is a graph showing SGN count was correlated with high frequency ABR threshold. Correlations between SGN cells density and ABR threshold shifts at the 120 day treatment point. Significant relations were revealed for the upper basal SGN density vs. 24 kHz according to the physiological place-frequency map of the mouse cochlea (Muller, et al., A physiological place—frequency map of the cochlea in the CBA/J mouse. Hearing Research. 2005; 202:1-2 63~73).
Figure 31B:
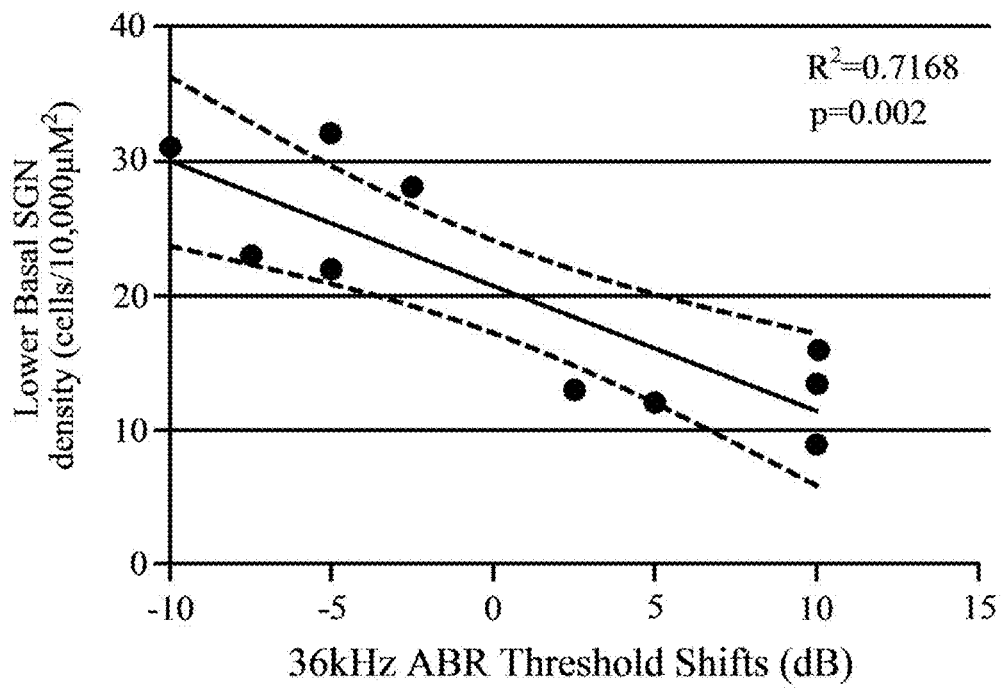
FIG. 31(B) is a graph showing SGN count was correlated with high frequency ABR threshold. Correlations between SGN cells density and ABR threshold shifts at the 120 day treatment point. Significant relations were revealed for the lower basal SGN density vs. 36 kHz; according to the physiological place-frequency map of the mouse cochlea (Muller, et al., A physiological place—frequency map of the cochlea in the CBA/J mouse. Hearing Research. 2005; 202:1-2 63~73).
Figure 32:
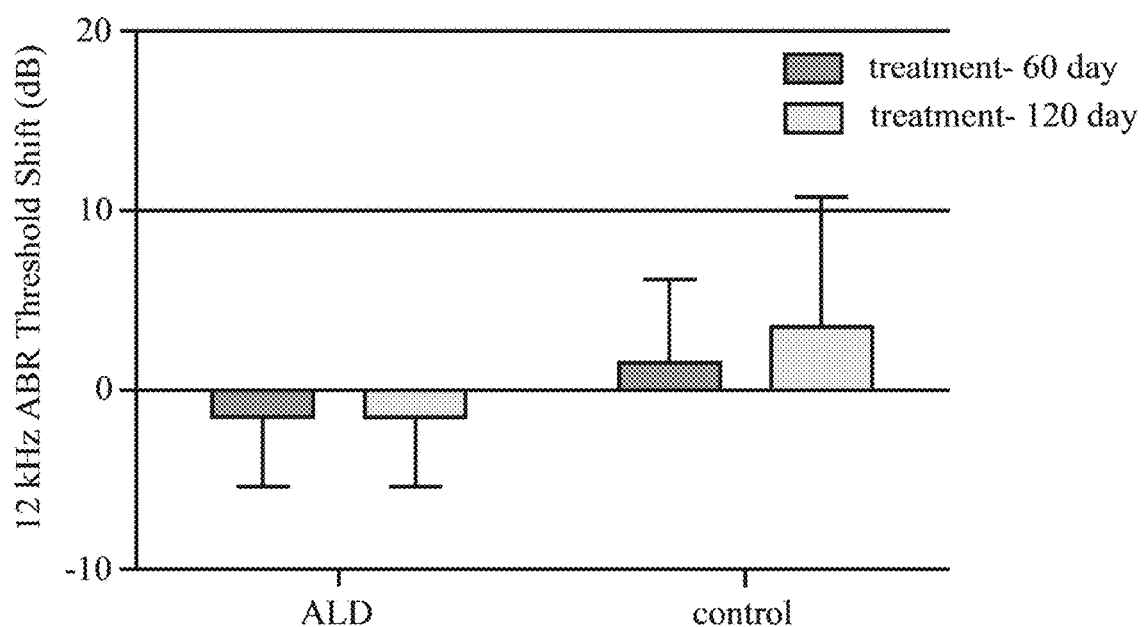
FIG. 32 is a graph showing ABR threshold shifts (dB) for ALD and non-ALD (control) groups. Mean (±SD) frequency-specific at 12 kHz ABR threshold shifts (dB) in the ALD-treatment group (n=5) on days 60 and 120 compared to the control group (n=5) values. Negative shifts represent improvements in hearing with age in the ALD treatment group; the positive shifts indicate age-related ABR threshold elevations in the control group.
Figure 33:
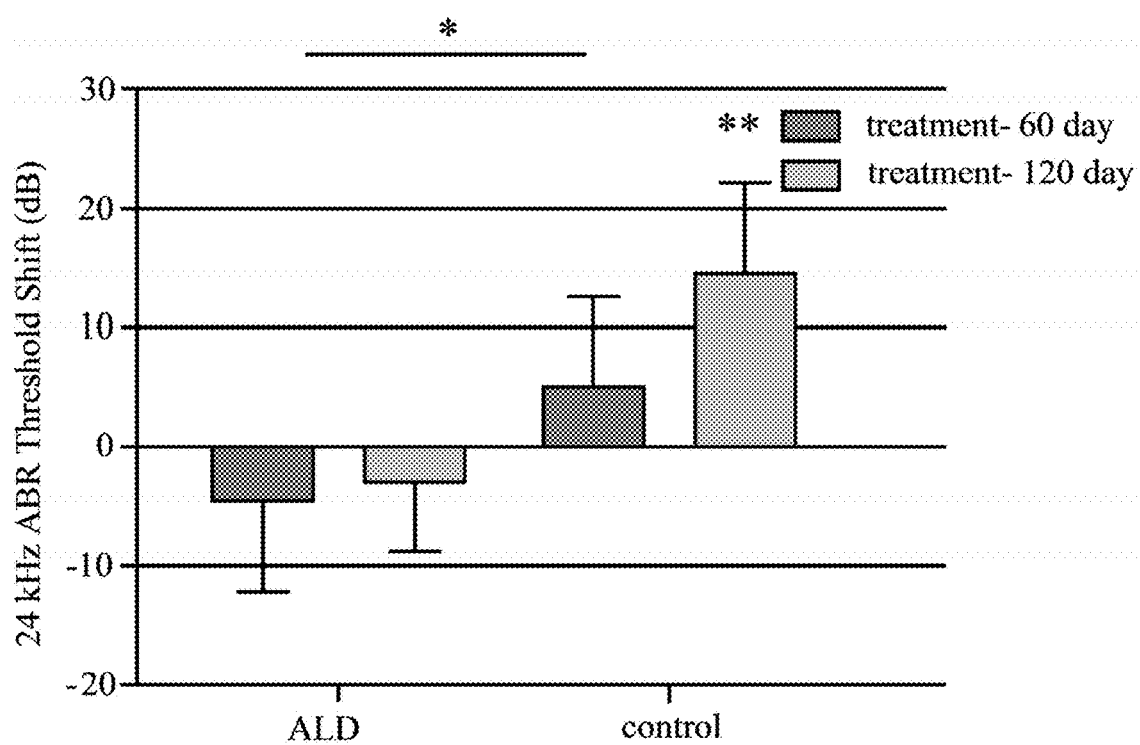
FIG. 33 is a graph showing ABR threshold shifts (dB) for ALD and non-ALD (control) groups. Mean (±SD) frequency-specific 24 kHz ABR threshold shifts (dB) in the ALD-treatment group (n=5) on days 60 and 120 compared to the control group (n=5) values. Negative shifts represent improvements in hearing with age in the ALD treatment group; the positive shifts indicate age-related ABR threshold elevations in the control group.
Figure 34:
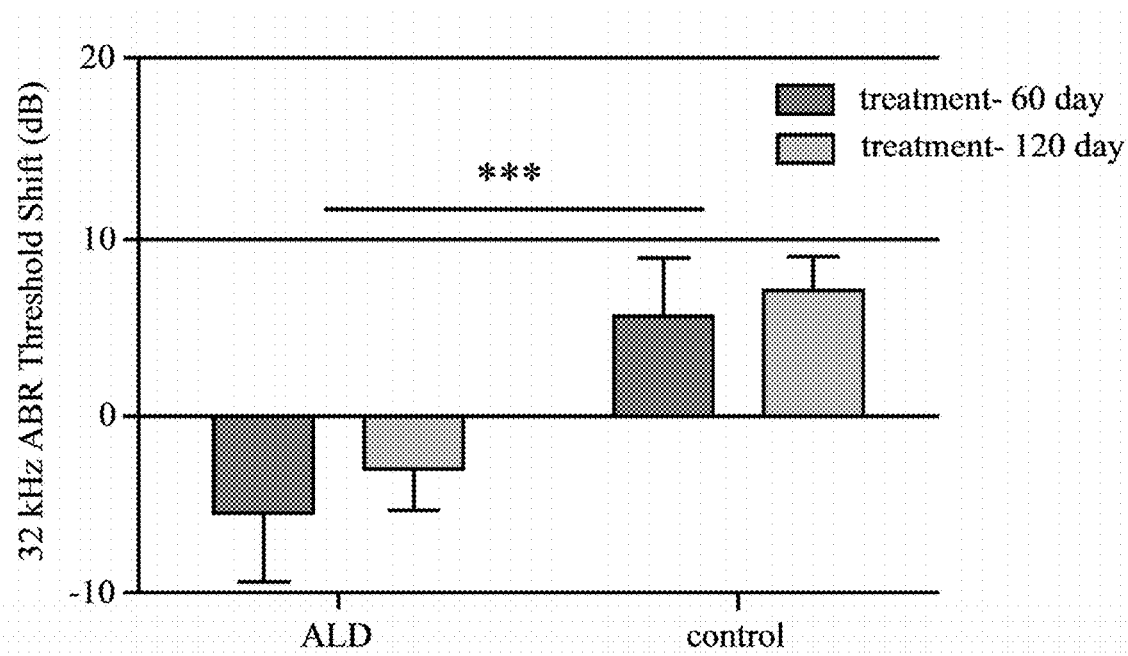
FIG. 34 is a graph showing ABR threshold shifts (dB) for ALD and non-ALD (control) groups. Mean (±SD) frequency-specific 32 kHz ABR threshold shifts (dB) in the ALD-treatment group (n=5) on days 60 and 120 compared to the control group (n=5) values. Negative shifts represent improvements in hearing with age in the ALD treatment group; the positive shifts indicate age-related ABR threshold elevations in the control group.
Figure 35:
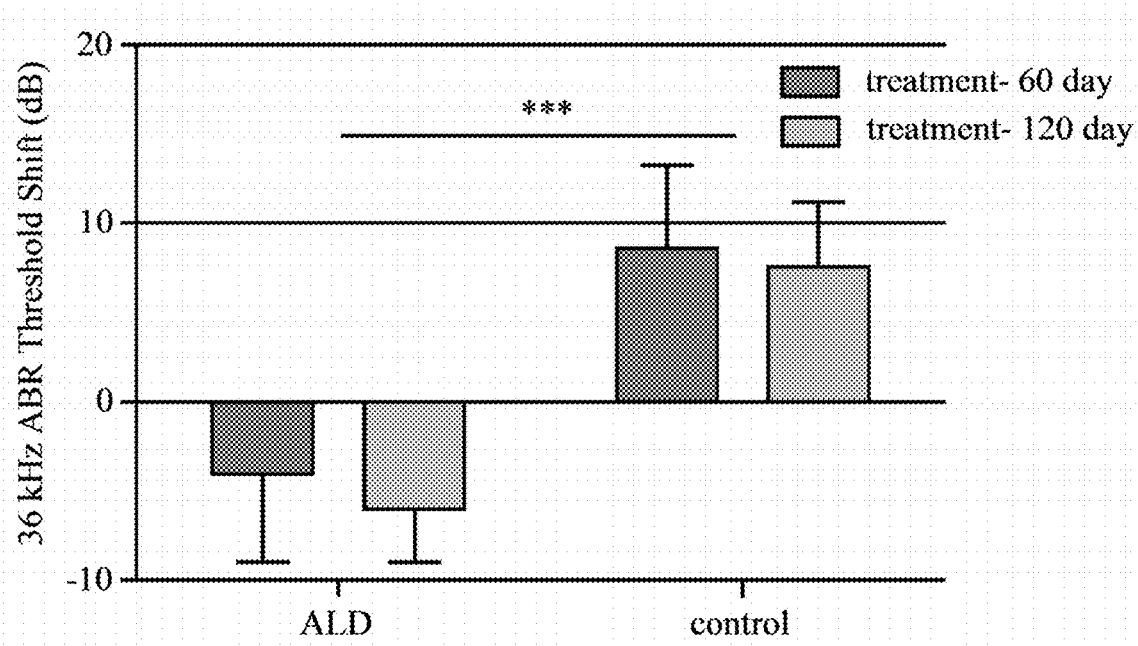
FIG. 35 is a graph showing ABR threshold shifts (dB) for ALD and non-ALD (control) groups. Mean (±SD) frequency-specific 36 kHz ABR threshold shifts (dB) in the ALD-treatment group (n=5) on days 60 and 120 compared to the control group (n=5) values. Negative shifts represent improvements in hearing with age in the ALD treatment group; the positive shifts indicate age-related ABR threshold elevations in the control group.

A comparison of the SGN density to ABR showed that as the mice lost SGN density in the upper basal region, seen in FIG. 31(A), and lower basal region, seen in FIG. 31(B), the correlations between SGN density and 24 and 36 kHz ABR threshold shifts indicate that fewer SGNs are associated with poorer hearing (higher ABR thresholds). Physiological place-frequency mapping of the mouse cochlea (Muller et al. Hearing Res., 2005, 63-73), state that 24 and 36 kHz are located at upper and lower basal turns of the cochlea, which match to the segments with the most cell density loss with age in CBA/CaJ mice. The ABR thresholds elevated significantly in the control group at 60 and 120 days of treatment relative to the ALD group at 24, 32, 36 kHz, at 120 days, indicating ALD may play a key role in preserving hearing and for modulating SGN degeneration in the aging cochlea. It could be a component in developing treatments to prevent or slow down the progression of age-related hearing loss—presbycusis.

ABR thresholds were significantly elevated in the control, non-treated, group relative to the ALD treated group at 24, 32 and 36 kHz, at 120 days. ABR peak 1 amplitude increased as a function of increasing stimulus intensity. The peak 1 amplitude increased significantly at high sound levels in ALD treated mice, relative to the control group.

Example 7

Declines in hormone levels play a role in age-linked diseases, including neurodegenerative conditions such as ARHL. Over-active or accumulating inflammatory responses or markers are another of the key etiologies implicated in aging, particularly in neurodegenerative disorders, including Alzheimer's Disease and age-related macular degeneration (Seddon et al. 2005; Nash et al. 2013). In particular, there is evidence that increased inflammatory activity and accumulation of inflammatory biomarkers in the auditory system may play a significant role in ARHL in humans (Verschuur et al. 2012). Indeed, several inflammatory markers in the cochlea are associated with hearing threshold changes in older adults, such as TNF-α, IL-6 and c-reactive protein (Verschuur et al. 2012; Tokarz et al. 2013). Since aspirin in low doses is very widely used in the primary and secondary prevention of coronary atherosclerosis in aged persons, optimal doses and durations are quite well understood clinically (Beers 2006). Therefore, inclusion of a safe anti-inflammatory drug in combination with ALD, would likely be a potent, safe inhibitor of the progression of ARHL.

CBA/CaJ mice (The Jackson Laboratory, Bar Harbor, Me.) were treated with aldosterone starting at 16-17 months of age. Treatment consisted of a subcutaneous implantation of a 120-day time-release pellet of D-aldosterone (0.0016 mg/day; Innovative Research of America, Sarasota, Fla.), a pellet containing ALD (0.0016 mg/day) and aspirin (0.125 mg/day, 0.083 mg/day or 0.042 mg/day), or a placebo, embedded subcutaneously behind the shoulder. As male mice weigh on average 28.0 g at week 9 and female mice 23.1 g, doses of the anti-inflammatory were designed to bracket a dose of 5 mg/kg/day. A total five groups (n=8, half male and half female) were tested. Treatment continued for 120 days or until the mouse was euthanized. The mice were kept in their home cages in the USF Vivarium room in the Global Center for Hearing & Speech Research, 12 hour light/dark cycle, 21 degrees C., in a relatively quiet environment with non-invasive auditory testing monthly. After the four month (120 day) course of treatment concluded, the mice were euthanized by injecting a commercial euthanasia solution, Euthasol®, (0.22 ml/kg) intraperitoneally. The depth of narcosis/anesthesia was assessed by using the interdigital pinch reflex. Death was confirmed by terminal phlebotomy/exsanguinations and perfusion.

After the mice were sacrificed, the brachial vessels are exposed after removing the skin over the axilla and the vessels ware cut. Blood was allowed to free-flow from the puncture site and collected with a sterile Pasteur pipette, then transferred to an Eppendorf tube in a 37° C. water bath for 30 min, centrifuged 2000 rpm for 25 min, and then the serum was taken off and stored at −80° C. Also a thoracotomy may performed to gain access to the heart was punctured by an 18G sterile hypodermic needle. Blood collection was done quickly to avoid clotting. Blood was collected in sample containers without any preservatives. The blood was permitted to clot and centrifuged at room temperature at 3000×g. Samples were stored at −20° C. until use. The mice were, and tested for ALD protein levels using rabbit anti-Aldosterone IgG-based ELISA kit (Cat. No 1875, Alpha Diagnostic Int., San Antonio Tex.) that uses a competitive solid phase.

The dose-response curve was designed to bracket 5 mg/kg daily for 120 days using subcutaneous, time-release pellets (slow-release, Innovative Research of America-IRA, Sarasota, Fla.), similar to the time-release pellets described in previous examples. Optimal aspirin dosages permit analysis of varying dosages of ALD, based on the results above, to determine synergism of ALD with aspirin, such as allowing reduction in the effective ALD dosage, for reducing ARHL.

Auditory sensitivity is assessed with pre-pulse inhibition of the acoustic startle response, where the frequency and intensity of the pre-pulse is varied to obtain threshold sensitivity across the mouse hearing range, as described above. Temporal Processing in Background Noise is assessed by a temporal-gap-in-noise acoustic startle paradigm, as described in rodent aging auditory system (e.g., Barsz et al. 2002). From extensive studies of the aging rodent auditory system by us and other groups, it is important to make the following ARHL biomarker measurements (particularly sensitive to detecting middle age signs of presbycusis in humans and rodents) prior to drug administration (baseline) and at longitudinal time points during drug administration: Auditory Sensitivity will be assessed using ABR thresholds with frequencies that cover the mouse/rat hearing range.

Figure 36A:
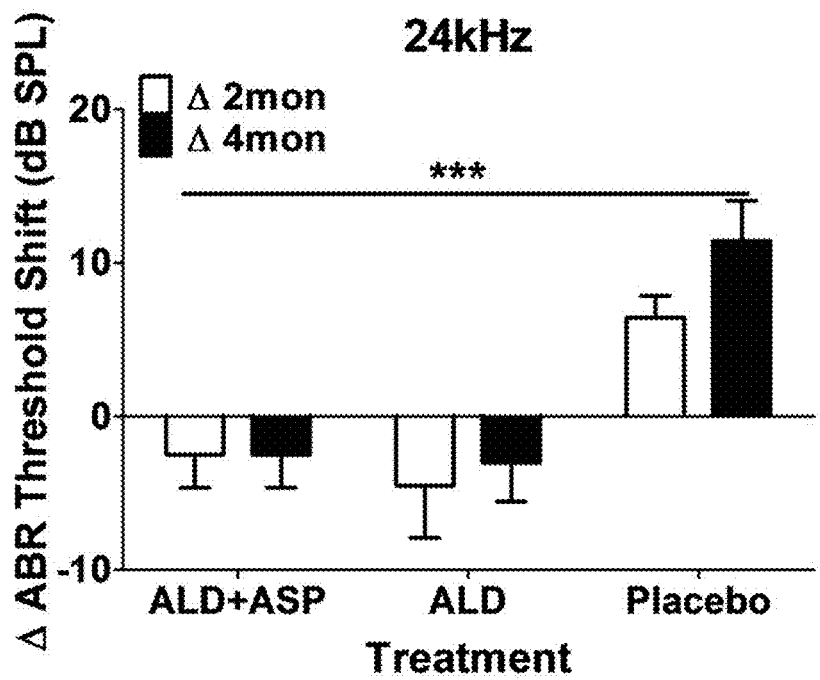
FIG. 36(A) is a graph showing ABR threshold shifts (dB) for ALD, ALD and aspirin (ALD+ASP) and non-ALD (control) groups. Mean (±SD) frequency-specific at (A) 24 kHz ABR threshold shifts (dB) in the ALD-treatment group (n=5) on days 60 and 120 compared to the control group (n=5) values. Negative shifts represent improvements in hearing with age in the ALD treatment group; the positive shifts indicate age-related ABR threshold elevations in the control group. *$p<0.005$; ** $p<0.001$.
Figure 36B:
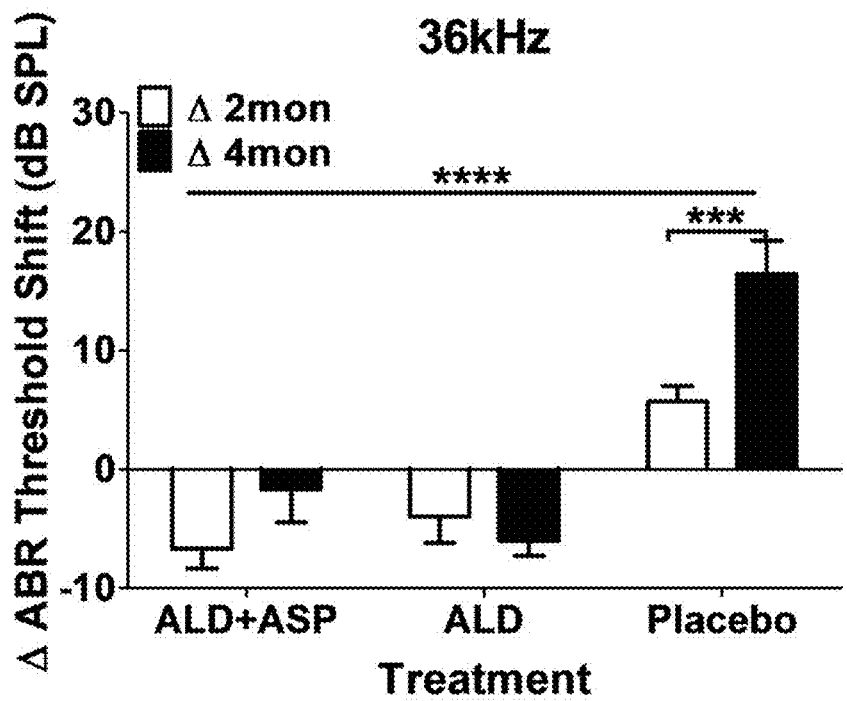
FIG. 36(B) is a graph showing ABR threshold shifts (dB) for ALD, ALD and aspirin (ALD+ASP) and non-ALD (control) groups. Mean (±SD) frequency-specific at 36 kHz ABR threshold shifts (dB) in the ALD-treatment group (n=5) on days 60 and 120 compared to the control group (n=5) values. Negative shifts represent improvements in hearing with age in the ALD treatment group; the positive shifts indicate age-related ABR threshold elevations in the control group. *$p<0.005$; ** $p<0.001$.

Mice were treated at middle age, as above, using 0.0016 mg/day of D-aldosterone, a combination of 0.0016 mg/day of D-aldosterone and 0.042 mg/day of Aspirin; and a control placebo (saline). Placebo showed an increase in ABR shift at both the 24 kHz and 36 kHz tests, as seen in FIGS. 36(A) and (B). Treatment with aldosterone only resulted in reduced ABR shifts, as seen previously and shown in FIGS. 36(A) and (B). By comparison, the combination treatment of aldosterone and Aspirin showed significantly decreased ABR thresholds compared to the control group at both 2 and 4 month of treatment, which did not change significantly over time. These results were similar to the ALD group, with hormone-treated mice showed improvement in 24 kHz, seen in FIG. 36(A). In testing at 36 kHz, seen in FIG. 36(B), frequency response at 2 months was increased significantly, which was slightly reduced at 4 months.

Example 8

ALD will be administered in combination with ibuprofen as described in Example 7, to test the efficacy of combining ALD with this FDA-approved anti-inflammatory agent, which has very few side effects, when administered chronically in moderate dosages. Specifically, the dose-response curve brackets 2.5 mg/kg daily for 120 days using subcutaneous, time-release pellets (slow-release, Innovative Research of America-IRA, Sarasota, Fla.).

Upon determination of the optimal ibuprofen dosage, analysis of varying dosages of ALD, based on the results above, determine synergism of ALD with ibuprofen, such as allowing reduction in the effective ALD dosage, for reducing ARHL.

Spiral ganglion neuron (SGN) degeneration with age is an important biomarker of presbycusis—age-related hearing loss (ARHL). ARHL represents the top communication deficit and neurodegenerative disorder of our aged population. Our previous study indicates a relationship between aldosterone (ALD) serum levels and the severity of ARHL in old human subjects, suggesting that ALD may be involved in the etiology of ARHL (Tadros, et al., High Serum Aldosterone Levels Correlate with Lower Hearing Thresholds in Aged Humans: A Possible Protective Hormone against Presbycusis. Hearing Research. 2005; 209:10-18). Also serum aldosterone (ALD) levels declined between young adult and middle-aged in CBA/CaJ (CBA) mice. But with 120 day ALD (0.0016 mg/day) treatments in middle-aged CBAs, these treated mice showed the highest serum ALD levels, but still within the normal ALD physiological range for mice. (Zhu, et al., Aldosterone reduces spiral ganglion neuron loss in middle-aged CBA/CaJ mice. ARO Abstract. 2014; 008).

Example 9

Figure 37:
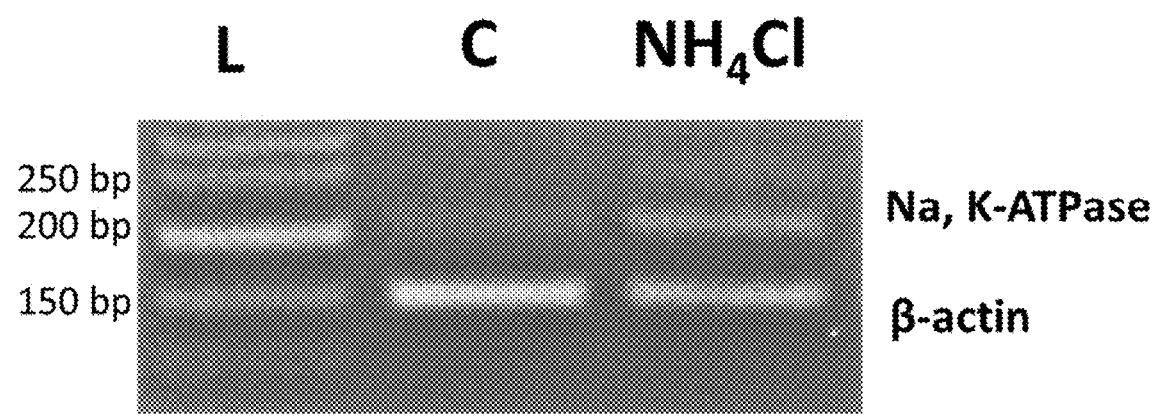
FIG. 37 is a blot showing the up-regulation of Na, K-ATPase with $NH_4Cl$. L is the DNA ladder, C is the control (vehicle treatment), $NH_4CL$ is treatment with 5 mM $NH_4Cl$ for 24 hours.

Ammonium chloride ($NH_4Cl$) as part of a proposed treatment of presbycusis is based on the fact that $NH_4Cl$ has been used with FDA approval as a diuretic; $NH_4Cl$ increases NKCC1 protein expression and activity in several studies in other physiological systems (Jayakumar et al. 2008; Ikebe et al. 2001); c) $NH_4Cl$ can also increase Na, K-ATPase activity (Masui et al. 2002; Garcon et al. 2007). For large doses, $NH_4Cl$ can induce metabolic acidosis, but in lower doses taken orally, there are no significant side effects in the short term. Our preliminary data, as shown in FIG. 37, demonstrates that $NH_4Cl$ (5 mM, 24 hr) treatment in vitro (HT-29 human cell line) enhances the mRNA expression of Na,K-ATPase compared to vehicle treatment (Control). These data suggest that $NH_4Cl$ could be used as part of a treatment to prevent age-related Na, K-ATPase down-regulation, and therefore part of a treatment for ARHL in combination with ALD, for the advantage of decreasing both effective dosages and reducing possible side effects.

Combining ALD with ammonium chloride will increase the efficacy of ALD through use of an FDA-approved drug, with very few side effects when administered in moderate dosages. The effective ALD dosage will be combined with several levels of ammonium chloride (dose-response curve), as determined from previous studies of the use of ammonium chloride in mice (Reisinger et al. 2009; Hafner 2008; Sato et al. 2011; Nowik et al. 2010; Lina et al. 1999; Sinawat et al. 2003). Specifically, mice will be fed a custom manufactured chow with 1-2% $NH_4Cl$ added to their normal diet (3028C, Harlan Teklad, Indianapolis, Ind.).

Once the optimal ammonium chloride dosage is determined, an additional experiment will be conducted for two dosages of ALD, to determine any synergism between ALD and ammonium chloride, i.e. if the effective amount of ALD is reduced when administered in a combination with ammonium chloride, for reducing ARHL.

For the ALD combinations that are effective, a combination using ibuprofen will be tested and the effects of a combination of ALD with aspirin, ibuprofen or $NH_4Cl$ treatments will compare the activity of NKCC1, KC, Cl- and Na,K-ATPase channels in the SV-K1 stria vascularis cell line, using bumetanide sensitive efflux $^{86}Rb$ uptake, HPLC determination of ADP derived from an ATP assay, and the FluxOR potassium ion channel assay (Life Technologies) will be used to detect the activities of these channels, in addition to protein synthesis (translation) and mRNA (transcription) levels.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of compounds and methods of treating age-related hearing disorders, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of treating an age-related hearing disorder, comprising:
    administering a therapeutically effective amount of a composition to a patient suffering from the age-related hearing disorder;
    wherein the composition comprises aldosterone, ammonium chloride, and an anti-inflammatory drug;
    wherein the aldosterone is administered at 0.004 mg/kg/day to 0.04 mg/kg/day;
    wherein the ammonium chloride administered at 8 g/day to about 12 g/day, and
    wherein the anti-inflammatory drug is administered at 2.5 mg/kg/day to 10 mg/kg/day.

2. The method of claim 1, wherein the age-related hearing disorder is presbycusis.

3. The method of claim 1, wherein the anti-inflammatory drug is non-steroidal.

4. The method of claim 3, wherein the non-steroidal anti-inflammatory drug is naproxen, salicylic acid, ibuprofen, diflurophenyl salicylate derivatives, salicylsalicylic acid, sodium salicylate, salicyclamide, sodium thiosalicylate, choline salicylate, magnesium salicylate, and cholinemagnesium salicylate, phenylbutazone, oxyphenylbutazone, antipyrine, aminopyrine, apazone, indomethacin, sulindac, phenacetin, acetaminophen, mefenamic, meclofenamic, flufenamic, mefenomic, ectofenamic, tolmectin, flurbioprofen, fenoprofen, ketoprofen, fenbufen, pirprofen, oxaprozin, or indoprofen.

5. A composition for treating chronic age-related hearing loss comprising:
    a therapeutically effective amount of the composition to give to a patient suffering from age-related hearing loss comprising aldosterone, ammonium chloride and a non-steroidal anti-inflammatory drug;
    wherein the aldosterone is at a dose of 0.004 mg/kg/day to 0.04 mg/kg/day;
    wherein the ammonium chloride is at a dose of 8 g/day to 12 g/day;
    wherein the non-steroidal anti-inflammatory drug is at a dose of 2.5 mg/kg/day to 10 mg/kg/day.

6. The composition of claim 5, wherein the non-steroidal anti-inflammatory drug is naproxen, salicylic acid, ibuprofen, diflurophenyl salicylate derivatives, salicylsalicylic acid, sodium salicylate, salicyclamide, sodium thiosalicylate, choline salicylate, magnesium salicylate, and cholinemagnesium salicylate, phenylbutazone, oxyphenylbutazone, antipyrine, aminopyrine, apazone, indomethacin, sulindac, phenacetin, acetaminophen, mefenamic, meclofenamic, flufenamic, mefenomic, ectofenamic, tolmectin, flurbioprofen, fenoprofen, ketoprofen, fenbufen, pirprofen, oxaprozin, or indoprofen.

7. The composition of claim 6, wherein the non-steroidal anti-inflammatory drug is aspirin.

8. The composition of claim 7, wherein the aspirin is at a dose of about 5 to about 10 mg/kg/day, 30 to 60 mg/day, 60 to about 100 mg/day, or 75 mg/day.

9. The composition of claim 6, wherein the non-steroidal anti-inflammatory drug is ibuprofen.

10. The composition of claim 9, wherein the ibuprofen is at a dose of about 2.5 mg/kg/day, about 0.4 g/day to about 1.2 g/day, or 100 mg/day.

11. The composition of claim 6, wherein the non-steroidal anti-inflammatory drug is naproxen.

12. The composition of claim 11, wherein the naproxen is at a dose of 5 to 10 mg/kg/day.

* * * * *